US012729210B2

(12) United States Patent
Wang et al.

(10) Patent No.: US 12,729,210 B2
(45) Date of Patent: Sep. 8, 2026

(54) CRYSTAL FORMS OF PYRIDOPYRAZOLE COMPOUNDS AND PREPARATION METHOD THEREFOR

(71) Applicant: GUANGZHOU BAIYUNSHAN PHARMACEUTICAL HOLDINGS CO., LTD. BAIYUNSHAN PHARMACEUTICAL GENERAL FACTORY, Guangzhou (CN)

(72) Inventors: Jiansong Wang, Guangzhou (CN); Zhifei Fu, Shanghai (CN); Zhibo Luo, Guangzhou (CN); Miaorong Luo, Shanghai (CN); Yang Zhang, Shanghai (CN); Jian Li, Shanghai (CN); Shuhui Chen, Shanghai (CN); Yingxia Bao, Guangzhou (CN); Wei Wang, Guangzhou (CN); Zhoufan Xie, Guangzhou (CN)

(73) Assignee: GUANGZHOU BAIYUNSHAN PHARMACEUTICAL HOLDINGS CO., LTD. BAIYUNSHAN PHARMACEUTICAL GENERAL FACTORY, Guangzhou (CN)

( * ) Notice: Subject to any disclaimer, the term of this patent is extended or adjusted under 35 U.S.C. 154(b) by 725 days.

(21) Appl. No.: 18/246,893

(22) PCT Filed: Sep. 26, 2021

(86) PCT No.: PCT/CN2021/120750

§ 371 (c)(1),
(2) Date: Mar. 28, 2023

(87) PCT Pub. No.: WO2022/068739

PCT Pub. Date: Apr. 7, 2022

(65) Prior Publication Data

US 2023/0365596 A1 Nov. 16, 2023

(30) Foreign Application Priority Data

Sep. 29, 2020 (CN) ........................ 202011051252.9
Oct. 19, 2020 (CN) ........................ 202011118921.X
Jan. 13, 2021 (CN) ........................ 202110051653.2

(51) Int. Cl.
*C07D 519/00* (2006.01)
*A61P 35/00* (2006.01)

(52) U.S. Cl.
CPC ............ *C07D 519/00* (2013.01); *A61P 35/00* (2018.01); *C07B 2200/13* (2013.01)

(58) Field of Classification Search
None
See application file for complete search history.

(56) References Cited

U.S. PATENT DOCUMENTS 10,023,570 B2 7/2018 Andrews et al.
10,138,243 B2 11/2018 Andrews et al.
(Continued)

FOREIGN PATENT DOCUMENTS

CN 108349969 A 7/2018
CN 109563097 A 4/2019
(Continued)

OTHER PUBLICATIONS

STN CAS Registry record for 2493156-27-5 (entry date Oct. 21, 2020). (Year: 2020).*

(Continued)

*Primary Examiner* — Jeffrey S Lundgren
*Assistant Examiner* — Sara Elizabeth Townsley
(74) *Attorney, Agent, or Firm* — Hoffmann & Baron, LLP

(57) ABSTRACT

Provided are crystal forms of compounds represented by formula(II)-formula (VIII) and formula (I)-formula (VIII-1),
(Continued)

a preparation method therefor and an application of the compounds and crystal forms in the preparation of a drug for treating a related disease.

(I)

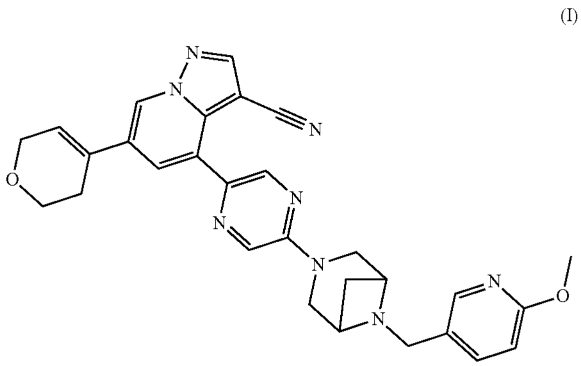

12 Claims, 20 Drawing Sheets

(56) References Cited

U.S. PATENT DOCUMENTS

| | | | |
|---|---|---|---|
| 10,174,027 | B2 | 1/2019 | Andrews et al. |
| 10,174,028 | B2 | 1/2019 | Andrews et al. |
| 10,844,038 | B2 | 11/2020 | Mansour et al. |
| 12,297,197 | B2 * | 5/2025 | Wang ...................... A61P 35/00 |
| 2017/0096425 | A1 | 4/2017 | Andrews et al. |
| 2018/0179203 | A1 | 6/2018 | Andrews et al. |
| 2018/0186790 | A1 | 7/2018 | Andrews et al. |
| 2018/0186791 | A1 | 7/2018 | Andrews et al. |
| 2019/0127373 | A1 | 5/2019 | Andrews et al. |
| 2019/0127374 | A1 | 5/2019 | Andrews et al. |
| 2019/0127375 | A1 | 5/2019 | Andrews et al. |
| 2020/0010442 | A1 | 1/2020 | Mansour et al. |
| 2020/0157107 | A1 | 5/2020 | Jordan et al. |

FOREIGN PATENT DOCUMENTS

| | | | | |
|---|---|---|---|---|
| CN | 110506043 | A | 11/2019 | |
| CN | 111527073 | A | 8/2020 | |
| CN | 111683949 | A | 9/2020 | |
| EP | 3845531 | A1 | 7/2021 | |
| EP | 3878852 | A1 | 9/2021 | |
| JP | 2018532690 | A | 11/2018 | |
| JP | 2019534857 | A | 12/2019 | |
| JP | 2020516636 | A | 6/2020 | |
| WO | 2018/049127 | A1 | 3/2018 | |
| WO | 2020064009 | A1 | 4/2020 | |
| WO | 2020094084 | A1 | 5/2020 | |
| WO | 2020114388 | A1 | 6/2020 | |
| WO | WO-2020200316 | A1 * | 10/2020 | ........... C07D 519/00 |

OTHER PUBLICATIONS

International Search Report for PCT/CN2021/120750, mailed Dec. 30, 2021.

Written Opinion of the International Searching Authority in PCT/CN2021/120750, mailed Dec. 30, 2021.

First Office Action for CN Application No. 202180049587.3 and English translation, dated May 27, 2024, pp. 1-7. The China National Intellectual Property Administration.

First search for CN Application No. 202180049587.3 and English translation, mailed May 27, 2024, pp. 1-5. The China National Intellectual Property Administration.

Rule 71(3) EPC Communication for European Application No. 21874399.5 dated Dec. 18, 2025, pp. 1-5. European Patent Office.

European search opinion for EP Application No. 21874399.5, pp. 1-4, Mar. 5, 2024.

Supplementary European search report for EP Application No. 21874399, pp. 1-2, Feb. 19, 2024.

Decision to Grant a Patent for JP Application No. 2023-514032 and English translation, pp. 1-5, Oct. 21, 2024.

Notice of Reasons for Refusal for JP Application No. 2023-514032 and English translation, pp. 1-8, Feb. 26, 2024.

* cited by examiner

CRYSTAL FORMS OF PYRIDOPYRAZOLE COMPOUNDS AND PREPARATION METHOD THEREFOR

CROSS-REFERENCE TO RELATED APPLICATIONS

The present application is a national phase entry under 35 USC 8 371 of International Application PCT/CN2021/120750, filed Sep. 26, 2021, which claims the benefit of and priority to Chinese Patent Application No. 202011051252.9, filed Sep. 29, 2020, Chinese Patent Application No. 202011118921.X, filed Oct. 19, 2020, and Chinese Patent Application No. 202110051653.2, filed Jan. 13, 2021. The entire disclosures of the above applications are incorporated herein by reference.

TECHNICAL FIELD

The present invention relates to compounds of formula (II) to formula (VIII), crystal forms of compounds of formula (I) to formula (VIII-1), preparation method thereof, and the application of the crystal forms in the preparation of a drug for treating related diseases.

BACKGROUND

RET protein is a receptor tyrosine kinase (RTK) and is also a transmembrane glycoprotein, expressed by the proto-oncogene RET (REarranged during Transection) located on chromosome 10. It plays an important role in the development of the kidney and enteric nervous systems in the embryonic stage, and is also crucial for homeostasis in various tissues, such as neurons, neuroendocrine, hematopoietic tissues and male germ cells, etc. Unlike other RTKs, RET does not directly bind to ligand molecules, such as artemin, glial cell line-derived neurotrophic factor (GDNF), neurturin and persephin, all of which belong to GNDF family ligands (GFLs). These ligands GFLs usually bind to GDNF receptor α (GFRα), and the formed GFL-GFRα complex mediates the self-dimerization of RET protein, leading to trans-autophosphorylation of tyrosine in the intracellular domain, recruitment of related linker proteins, activation of cell proliferation and other signaling cascade reactions. The related signaling pathways include MAPK, PI3K, JAK-STAT, PKA, PKC, etc.

There are two main carcinogenic activation mechanisms of RET, one of which is chromosome rearrangement to produce a new fusion protein usually by the fusion of RET kinase domain to a protein containing self-dimerization domain, and the other one of which is RET mutation that directly or indirectly activates the kinase activity of RET. Changes in the levels of these somatic or germ cells are involved in the pathogenesis of various cancers. 5-10% of patients with papillary thyroid cancer have RET chromosome rearrangement; point mutations in RET were found in 60% of those with medullary thyroid cancer; and there are 10-20% of patients with RET fusion among all patients with thyroid cancer, in which CCDC6 and NCOA4 are the most common fusions. Among all NSCLC patients, roughly 1-2% of them have RET fusion proteins, among which KIF5B-RET is the most common.

In summary, abnormal RET expression or activation has been found in many tumors and gastrointestinal disorders such as irritable bowel syndrome. Therefore, RET inhibitors have potential clinical value in tumors or intestinal disorders.

SUMMARY

The present invention provides compounds represented by Formulas (II) to (VIII), (II)

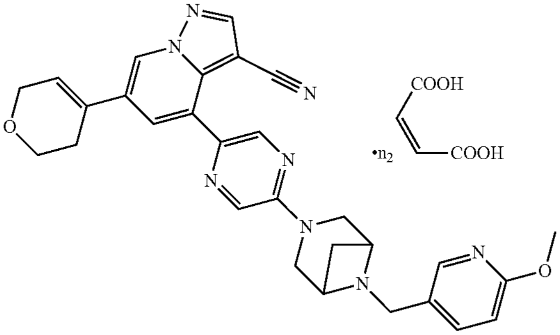

(III)

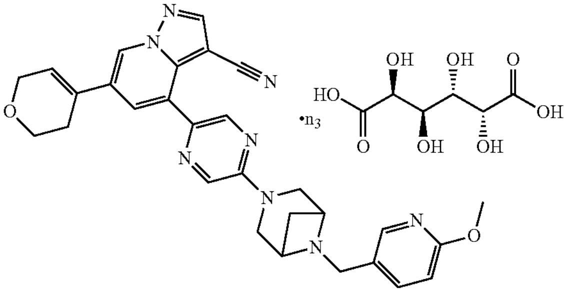

(IV)

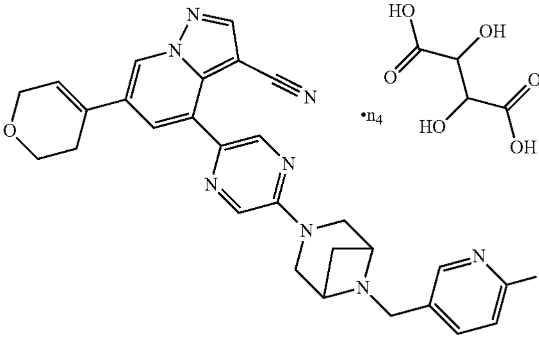

(V)

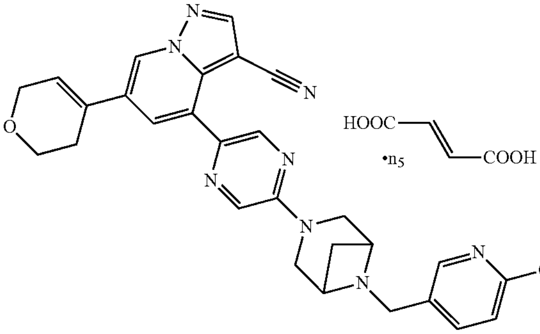

-continued
(VI)
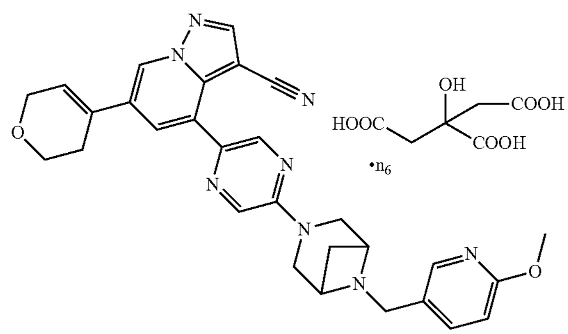
(VII)
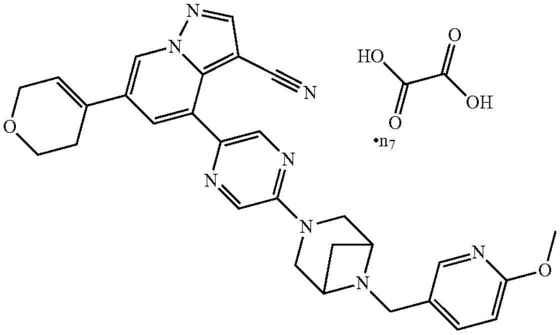
(VIII)
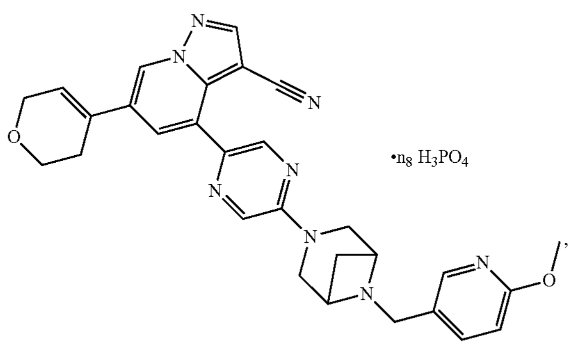
wherein $n_2$, $n_3$, $n_4$, $n_5$, $n_6$, $n_7$ and $n_8$ are selected from 0.8-1.5.
In some embodiments of the present invention, the above-mentioned $n_2$, $n_3$, $n_4$, $n_5$, $n_6$, $n_7$ and $n_8$ are each independently selected from 0.8, 0.9, 1.0, 1.1, 1.2, 1.3, 1.4 and 1.5.
In some embodiments of the present invention, the above-mentioned compound is selected from
(II-1)
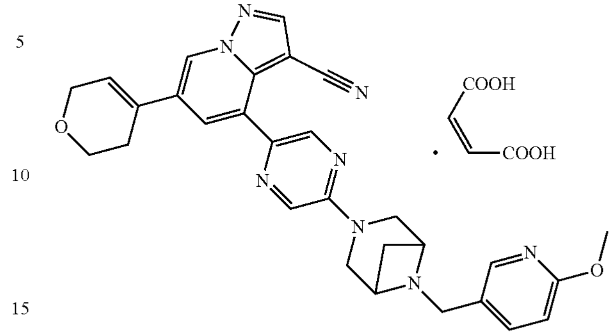
(III-1)
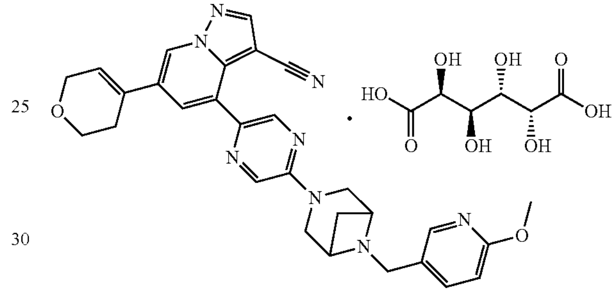
(IV-1)
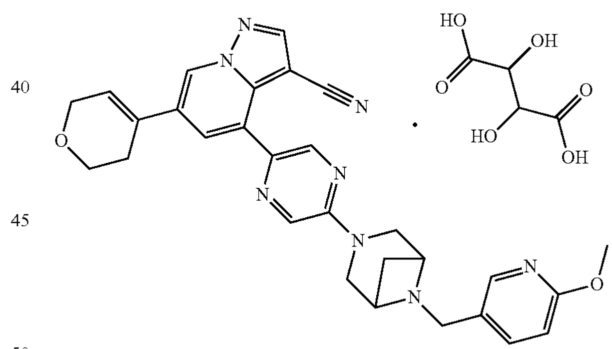
(V-1)
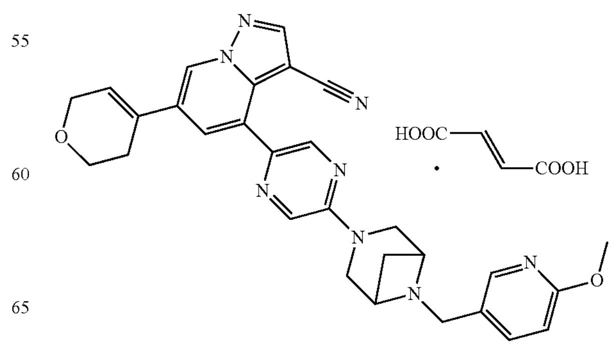

-continued (VI-1)

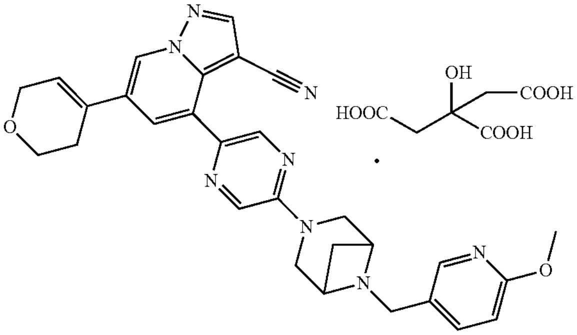

(VII-1)

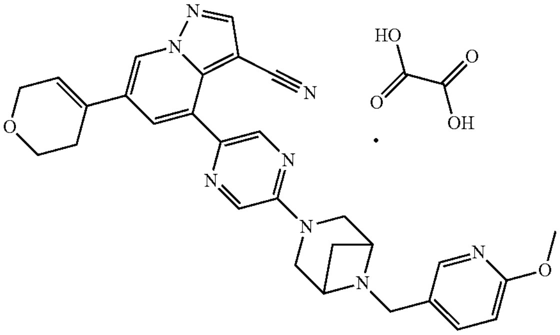

(VIII-1)

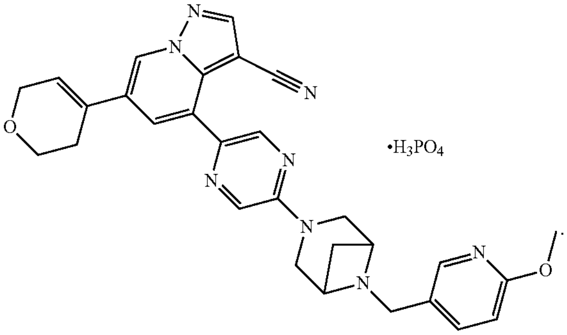

The present invention provides crystal form A of the compound of Formula (I), characterized in that an X-ray powder diffraction pattern of the crystal form A has characteristic diffraction peaks at the following 2θ angles: 16.30±0.20°, 21.69±0.20° and 24.63±0.20°.

(I)

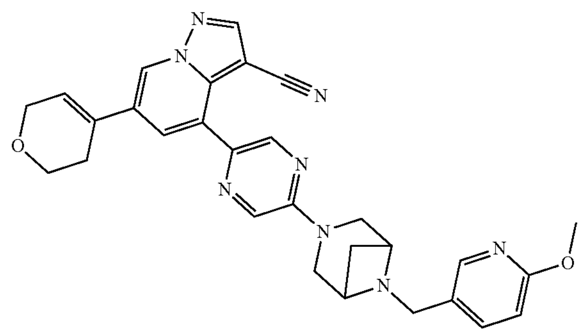

In some embodiments of the present invention, the X-ray powder diffraction pattern of the above-mentioned crystal form A has characteristic diffraction peaks at the following 2θ angles: 14.88±0.20°, 15.51±0.20°, 16.30±0.20°, 18.49±0.20°, 19.16±0.20°, 19.70±0.20°, 21.69±0.20° and 24.63±0.20°.

In some embodiments of the present invention, the X-ray powder diffraction pattern of the above-mentioned crystal form A has characteristic diffraction peaks at the following 2θ angles: 7.79±0.20°, 9.58±0.20°, 12.61±0.20°, 14.88±0.20°, 15.51±0.20°, 16.30±0.20°, 18.49±0.20°, 19.16±0.20°, 19.70±0.20°, 21.69±0.20° and 24.63±0.20°.

In some embodiments of the present invention, the X-ray powder diffraction pattern of the above-mentioned crystal form A has characteristic diffraction peaks at the following 2θ angles: 6.19±0.20°, 7.79±0.20°, 9.58±0.20°, 12.61±0.20°, 14.88±0.20°, 15.51±0.20°, 16.30±0.20°, 17.65±0.20°, 18.49±0.20°, 19.16±0.20°, 19.70±0.20°, 20.45±0.20°, 21.69±0.20°, 23.38±0.20°, 24.63±0.20° and 25.29±0.20°.

In some embodiments of the present invention, the X-ray powder diffraction pattern of the above-mentioned crystal form A has characteristic diffraction peaks at the following 2θ angles: 6.19°, 7.79°, 9.21°, 9.58°, 10.32°, 12.61°, 14.88°, 15.10°, 15.51° 16.30°, 16.60°, 17.65°, 18.49°, 19.16°, 19.70° 20.03°, 20.45°, 21.69°, 22.24°, 22.83°, 23.38°, 24.63°, 25.29°, 25.76°, 27.70°, 28.34° and 29.06°.

In some embodiments of the present invention, the X-ray powder diffraction pattern of the above-mentioned crystal form A has characteristic diffraction peaks at the following 2θ angles: 16.30±0.20° and 21.69±0.20°, and may also have characteristic diffraction peaks at 24.63±0.20° and/or 6.19±0.20° and/or 7.79±0.20° and/or 9.21±0.20° and/or 9.58±0.20° and/or 10.32±0.20° and/or 12.61±0.20° and/or 14.88±0.20° and/or 15.1±0.20° and/or 15.51±0.20° and/or 16.6±0.20° and/or 17.65±0.20° and/or 18.49±0.20° and/or 19.16±0.20° and/or 19.7±0.20° and/or 20.03±0.20° and/or 20.45±0.20° and/or 22.24±0.20° and/or 22.83±0.20° and/or 23.38±0.20° and/or 25.29±0.20° and/or 25.76±0.20° and/or 27.7±0.20° and/or 28.34±0.20° and/or 29.06±0.20°.

In some embodiments of the present invention, an XRPD pattern of the above-mentioned crystal form A is as shown in FIG. 1.

In some embodiments of the present invention, the XRPD pattern of the above-mentioned crystal form A is as shown in FIG. 39.

In some embodiments of the present invention, the XRPD pattern analysis data of the above-mentioned crystal form A are as shown in Table 1-1:

TABLE 1-1

XRPD pattern analysis data of crystal form A of compound of Formula (I)

| No. | 2θ angle (°) | Interplanar spacing (Å) | Relative intensity (%) |
|---|---|---|---|
| 1 | 3.29 | 26.82 | 15.88 |
| 2 | 6.19 | 14.27 | 17.90 |
| 3 | 7.79 | 11.34 | 24.52 |
| 4 | 9.21 | 9.61 | 14.65 |
| 5 | 9.58 | 9.23 | 33.41 |
| 6 | 10.32 | 8.57 | 10.66 |
| 7 | 12.61 | 7.02 | 17.66 |
| 8 | 14.88 | 5.95 | 40.48 |
| 9 | 15.10 | 5.87 | 19.56 |
| 10 | 15.51 | 5.71 | 59.73 |

TABLE 1-1-continued

| XRPD pattern analysis data of crystal form A of compound of Formula (I) | | | |
|---|---|---|---|
| No. | 2θ angle (°) | Interplanar spacing (Å) | Relative intensity (%) |
| 11 | 16.30 | 5.44 | 100.00 |
| 12 | 16.60 | 5.34 | 28.62 |
| 13 | 17.65 | 5.02 | 18.70 |
| 14 | 18.49 | 4.80 | 36.32 |
| 15 | 19.16 | 4.63 | 63.30 |
| 16 | 19.70 | 4.51 | 47.66 |
| 17 | 20.03 | 4.43 | 31.92 |
| 18 | 20.45 | 4.34 | 14.43 |
| 19 | 21.69 | 4.10 | 74.09 |
| 20 | 22.24 | 4.00 | 11.18 |
| 21 | 22.83 | 3.90 | 12.54 |
| 22 | 23.38 | 3.81 | 15.94 |
| 23 | 24.63 | 3.61 | 78.38 |
| 24 | 25.29 | 3.52 | 18.04 |
| 25 | 25.76 | 3.46 | 13.74 |
| 26 | 26.58 | 3.35 | 6.88 |
| 27 | 27.70 | 3.22 | 11.92 |
| 28 | 28.34 | 3.15 | 12.47 |
| 29 | 29.06 | 3.07 | 10.36 |
| 30 | 31.71 | 2.82 | 9.67 |
| 31 | 32.97 | 2.72 | 3.06 |
| 32 | 33.49 | 2.68 | 2.38 |

In some embodiments of the present invention, the XRPD pattern analysis data of the above-mentioned crystal form A are as shown in Table 1-2:

TABLE 1-2

| XRPD pattern analysis data of crystal form A of compound of Formula (I) | | | | |
|---|---|---|---|---|
| No. | 2θ angle (°) | Interplanar spacing (Å) | Intensity | Relative intensity (%) |
| 1 | 6.080 | 14.5243 | 167 | 6.8 |
| 2 | 7.683 | 11.4979 | 264 | 10.8 |
| 3 | 9.475 | 9.3266 | 553 | 22.6 |
| 4 | 10.234 | 8.6363 | 109 | 4.5 |
| 5 | 12.518 | 7.0657 | 287 | 11.7 |
| 6 | 14.742 | 6.0040 | 874 | 35.7 |
| 7 | 14.997 | 5.9028 | 267 | 10.9 |
| 8 | 15.440 | 5.7344 | 461 | 18.8 |
| 9 | 16.182 | 5.4728 | 2448 | 100.0 |
| 10 | 17.540 | 5.0520 | 88 | 3.6 |
| 11 | 18.343 | 4.8326 | 212 | 8.7 |
| 12 | 19.022 | 4.6617 | 1771 | 72.4 |
| 13 | 19.601 | 4.5253 | 303 | 12.4 |
| 14 | 19.924 | 4.4528 | 725 | 29.6 |
| 15 | 20.337 | 4.3632 | 102 | 4.2 |
| 16 | 21.082 | 4.2106 | 109 | 4.4 |
| 17 | 21.601 | 4.1107 | 1305 | 53.3 |
| 18 | 22.374 | 3.9703 | 126 | 5.1 |
| 19 | 22.687 | 3.9164 | 93 | 3.8 |
| 20 | 23.299 | 3.8148 | 365 | 14.9 |
| 21 | 24.140 | 3.6838 | 395 | 16.1 |
| 22 | 24.522 | 3.6272 | 850 | 34.7 |
| 23 | 25.201 | 3.5309 | 449 | 18.4 |
| 24 | 25.645 | 3.4709 | 168 | 6.9 |
| 25 | 26.499 | 3.3609 | 75 | 3.0 |
| 26 | 27.719 | 3.2157 | 193 | 7.9 |
| 27 | 28.261 | 3.1552 | 156 | 6.4 |
| 28 | 28.958 | 3.0809 | 301 | 12.3 |
| 29 | 30.234 | 2.9537 | 38 | 1.6 |
| 30 | 30.980 | 2.8843 | 65 | 2.6 |
| 31 | 31.659 | 2.8239 | 156 | 6.4 |
| 32 | 32.801 | 2.7282 | 117 | 4.8 |
| 33 | 33.423 | 2.6788 | 49 | 2.0 |
| 34 | 34.557 | 2.5934 | 89 | 3.6 |
| 35 | 34.902 | 2.5686 | 68 | 2.8 |

TABLE 1-2-continued

| XRPD pattern analysis data of crystal form A of compound of Formula (I) | | | | |
|---|---|---|---|---|
| No. | 2θ angle (°) | Interplanar spacing (Å) | Intensity | Relative intensity (%) |
| 36 | 35.678 | 2.5145 | 57 | 2.3 |
| 37 | 36.382 | 2.4674 | 39 | 1.6 |
| 38 | 38.218 | 2.3530 | 43 | 1.8 |

In some embodiments of the present invention, a differential scanning calorimetry curve of the above-mentioned crystal form A has a starting point of an endothermic peak at 188.7±2° C.

In some embodiments of the present invention, a DSC thermogram of the above-mentioned crystal form A is as shown in FIG. 2.

In some embodiments of the present invention, a thermogravimetric analysis curve of the above-mentioned crystal form A shows a weight loss of 1.20% at 180.0±3° C.

In some embodiments of the present invention, a TGA spectrum of the above-mentioned crystal form A is as shown in FIG. 3.

The present invention provides crystal form B of the compound of Formula (I), characterized in that the X-ray powder diffraction pattern of the crystal form B has characteristic diffraction peaks at the following 2θ angles: 6.66±0.20°, 17.97±0.20° and 22.63±0.20°.

In some embodiments of the present invention, the X-ray powder diffraction pattern of the above-mentioned crystal form B has characteristic diffraction peaks at the following 2θ angles: 6.66±0.20°, 8.50±0.20°, 13.30±0.20°, 16.14±0.20°, 16.70±0.20°, 17.97±0.20°, 19.66±0.20° and 22.63±0.20°.

In some embodiments of the present invention, the XRPD pattern of the above-mentioned crystal form B is as shown in FIG. 4.

In some embodiments of the present invention, the XRPD pattern analysis data of the above-mentioned crystal form B are as shown in Table 2:

TABLE 2

| XRPD pattern analysis data of crystal form B of compound of Formula (I) | | | |
|---|---|---|---|
| No. | 2θ angle (°) | Interplanar spacing (Å) | Relative intensity (%) |
| 1 | 4.67 | 18.94 | 2.83 |
| 2 | 6.00 | 14.73 | 27.73 |
| 3 | 6.66 | 13.27 | 71.73 |
| 4 | 8.50 | 10.40 | 39.67 |
| 5 | 9.85 | 8.98 | 7.78 |
| 6 | 12.40 | 7.14 | 22.18 |
| 7 | 13.30 | 6.66 | 30.38 |
| 8 | 16.14 | 5.49 | 49.29 |
| 9 | 16.70 | 5.31 | 35.76 |
| 10 | 17.97 | 4.94 | 100.00 |
| 11 | 18.89 | 4.70 | 18.94 |
| 12 | 19.66 | 4.52 | 32.07 |
| 13 | 20.78 | 4.28 | 15.91 |
| 14 | 21.25 | 4.18 | 15.78 |
| 15 | 22.63 | 3.93 | 61.52 |
| 16 | 23.63 | 3.76 | 16.41 |
| 17 | 24.89 | 3.58 | 6.81 |
| 18 | 25.88 | 3.44 | 10.44 |
| 19 | 28.02 | 3.18 | 2.56 |
| 20 | 29.34 | 3.04 | 3.67 |

TABLE 2-continued

XRPD pattern analysis data of crystal form B of compound of Formula (I)

| No. | 2θ angle (°) | Interplanar spacing (Å) | Relative intensity (%) |
|---|---|---|---|
| 21 | 32.55 | 2.75 | 5.66 |
| 22 | 33.46 | 2.68 | 2.77 |

The present invention provides crystal form C of the compound of Formula (I), characterized in that the X-ray powder diffraction pattern of the crystal form C has characteristic diffraction peaks at the following 2θangles: 16.66±0.20°, 19.22±0.20° and 20.99±0.20°.

In some embodiments of the present invention, the X-ray powder diffraction pattern of the above-mentioned crystal form C has characteristic diffraction peaks at the following 2θangles: 9.08±0.20°, 12.06±0.20°, 16.15±0.20°, 16.66±0.20°, 17.13±0.20°, 19.22±0.20°, 20.99±0.20° and 24.52±0.20°.

In some embodiments of the present invention, the XRPD pattern of the above-mentioned crystal form C is as shown in FIG. 5.

In some embodiments of the present invention, the XRPD pattern analysis data of the above-mentioned crystal form C are as shown in Table 3:

TABLE 3

XRPD pattern analysis data of crystal form C of compound of Formula (I)

| No. | 2θ angle (°) | Interplanar spacing (Å) | Relative intensity (%) |
|---|---|---|---|
| 1 | 9.08 | 9.74 | 11.96 |
| 2 | 12.06 | 7.34 | 37.76 |
| 3 | 16.15 | 5.49 | 30.91 |
| 4 | 16.66 | 5.32 | 42.91 |
| 5 | 17.13 | 5.18 | 34.34 |
| 6 | 19.22 | 4.62 | 49.17 |
| 7 | 20.99 | 4.23 | 100.00 |
| 8 | 24.52 | 3.63 | 6.82 |
| 9 | 27.95 | 3.19 | 5.34 |

In some embodiments of the present invention, the differential scanning calorimetry curve of the above-mentioned crystal form C has a starting point of an endothermic peak at 171.7±2° C.

In some embodiments of the present invention, the DSC thermogram of the above-mentioned crystal form C is as shown in FIG. 6.

In some embodiments of the present invention, the thermogravimetric analysis curve of the above-mentioned crystal form C shows a weight loss of 10.08% at 140.0±3° C.

In some embodiments of the present invention, the TGA spectrum of the above-mentioned crystal form C is as shown in FIG. 7.

The present invention provides crystal form D of the compound of Formula (I), characterized in that the X-ray powder diffraction pattern of the crystal form D has characteristic diffraction peaks at the following 2θangles: 4.79±0.20°, 14.89±0.20° and 16.70±0.20°.

In some embodiments of the present invention, the X-ray powder diffraction pattern of the above-mentioned crystal form D has characteristic diffraction peaks at the following 2θangles: 4.79±0.20°, 6.61±0.20°, 7.16±0.20°, 14.89±0.20°, 16.09±0.20°, 16.70±0.20°, 19.40±0.20° and 20.73±0.20°.

In some embodiments of the present invention, the XRPD pattern of the above-mentioned crystal form D is as shown in FIG. 8.

In some embodiments of the present invention, the XRPD pattern analysis data of the above-mentioned crystal form D are as shown in Table 4:

TABLE 4

XRPD pattern analysis data of crystal form D of compound of Formula (I)

| No. | 2θ angle (°) | Interplanar spacing (Å) | Relative intensity (%) |
|---|---|---|---|
| 1 | 4.79 | 18.43 | 100.00 |
| 2 | 6.61 | 13.38 | 45.87 |
| 3 | 7.16 | 12.35 | 42.59 |
| 4 | 9.28 | 9.53 | 29.29 |
| 5 | 11.87 | 7.46 | 19.25 |
| 6 | 14.89 | 5.95 | 53.30 |
| 7 | 16.09 | 5.51 | 36.74 |
| 8 | 16.70 | 5.31 | 47.38 |
| 9 | 17.98 | 4.93 | 31.64 |
| 10 | 18.73 | 4.74 | 35.18 |
| 11 | 19.40 | 4.58 | 41.79 |
| 12 | 20.73 | 4.29 | 42.06 |
| 13 | 21.71 | 4.09 | 27.25 |
| 14 | 23.76 | 3.74 | 27.95 |
| 15 | 24.94 | 3.57 | 18.23 |
| 16 | 27.98 | 3.19 | 7.18 |

The present invention provides crystal form E of the compound of Formula (I), characterized in that the X-ray powder diffraction pattern of the crystal form E has characteristic diffraction peaks at the following 2θangles: 8.01±0.20°, 17.80±0.20° and 19.14±0.20°.

In some embodiments of the present invention, the X-ray powder diffraction pattern of the above-mentioned crystal form E has characteristic diffraction peaks at the following 2θangles: 8.01±0.20°, 14.15±0.20°, 14.84±0.20°, 16.29±0.20°, 17.23±0.20°, 17.80±0.20°, 18.28±0.20° and 19.14±0.20°.

In some embodiments of the present invention, the X-ray powder diffraction pattern of the above-mentioned crystal form E has characteristic diffraction peaks at the following 2θangles: 5.98±0.20°, 8.01±0.20°, 9.21±0.20°, 12.9±0.20°, 14.15±0.20°, 14.84±0.20°, 16.29±0.20°, 17.23±0.20°, 17.8±0.20°, 18.28±0.20°, 19.14±0.20° and 20.7±0.20°.

In some embodiments of the present invention, the XRPD pattern of the above-mentioned crystal form E is as shown in FIG. 9.

In some embodiments of the present invention, the XRPD pattern analysis data of the above-mentioned crystal form E are as shown in Table 5:

TABLE 5

XRPD pattern analysis data of crystal form E of compound of Formula (I)

| No. | 2θ angle (°) | Interplanar spacing (Å) | Relative intensity (%) |
|---|---|---|---|
| 1 | 5.98 | 14.78 | 25.62 |
| 2 | 8.01 | 11.04 | 72.40 |
| 3 | 9.21 | 9.60 | 26.77 |
| 4 | 11.75 | 7.53 | 12.78 |
| 5 | 12.90 | 6.86 | 26.69 |
| 6 | 14.15 | 6.26 | 51.73 |
| 7 | 14.84 | 5.97 | 35.86 |

TABLE 5-continued

| XRPD pattern analysis data of crystal form E of compound of Formula (I) | | | |
|---|---|---|---|
| No. | 2θ angle (°) | Interplanar spacing (Å) | Relative intensity (%) |
| 8 | 16.29 | 5.44 | 48.64 |
| 9 | 17.23 | 5.15 | 43.93 |
| 10 | 17.80 | 4.98 | 100.00 |
| 11 | 18.28 | 4.85 | 38.87 |
| 12 | 19.14 | 4.64 | 77.89 |
| 13 | 20.70 | 4.29 | 35.09 |
| 14 | 21.69 | 4.10 | 22.89 |
| 15 | 24.19 | 3.68 | 7.93 |
| 16 | 25.94 | 3.44 | 10.07 |

In some embodiments of the present invention, the differential scanning calorimetry curve of the above-mentioned crystal form E has a starting point of an endothermic peak at 170.6±2° C. and a starting point of another endothermic peak at 189.1±2° C.

In some embodiments of the present invention, the DSC thermogram of the above-mentioned crystal form E is as shown in FIG. 10.

In some embodiments of the present invention, the thermogravimetric analysis curve of the above-mentioned crystal form E shows a weight loss of 5.59% at 150.0±3° C.

In some embodiments of the present invention, the TGA spectrum of the above-mentioned crystal form E is as shown in FIG. 11.

The present invention provides crystal form F of the compound of Formula (I), characterized in that the X-ray powder diffraction pattern of the above-mentioned crystal form F has characteristic diffraction peaks at the following 2θangles: 4.95±0.20°, 7.13±0.20° and 16.55±0.20°.

In some embodiments of the present invention, the X-ray powder diffraction pattern of the above-mentioned crystal form F has characteristic diffraction peaks at the following 2θangles: 4.95±0.20°, 7.13±0.20°, 14.75±0.20°, 16.55±0.20°, 23.62±0.20° and 24.96±0.20°.

In some embodiments of the present invention, the XRPD pattern of the above-mentioned crystal form F is as shown in FIG. 12.

In some embodiments of the present invention, the XRPD pattern analysis data of the above-mentioned crystal form F are as shown in Table 6:

TABLE 6

| XRPD pattern analysis data of crystal form F of compound of Formula (I) | | | |
|---|---|---|---|
| No. | 2θ angle (°) | Interplanar spacing (Å) | Relative intensity (%) |
| 1 | 4.95 | 17.86 | 100.00 |
| 2 | 7.13 | 12.40 | 69.85 |
| 3 | 14.75 | 6.01 | 17.58 |
| 4 | 16.55 | 5.36 | 35.39 |
| 5 | 23.62 | 3.77 | 9.08 |
| 6 | 24.96 | 3.57 | 17.43 |

The present invention provides crystal form G of the compound of Formula (II-1), characterized in that the X-ray powder diffraction pattern of the crystal form G has characteristic diffraction peaks at the following 2θangles: 11.98±0.20°, 17.90±0.20° and 21.56±0.20°.

(II-1)

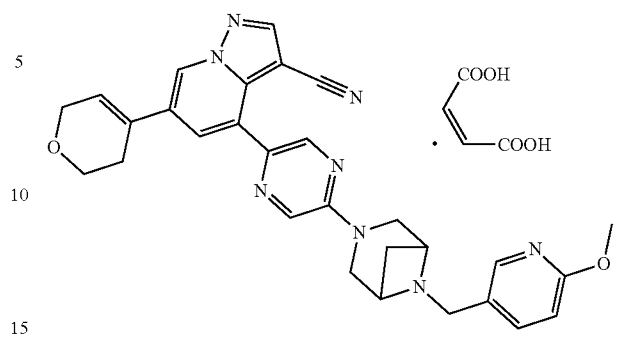

In some embodiments of the present invention, the X-ray powder diffraction pattern of the above-mentioned crystal form G has characteristic diffraction peaks at the following 2θangles: 11.98±0.20°, 12.39±0.20°, 16.53±0.20°, 17.90±0.20°, 21.56±0.20°, 23.36±0.20°, 24.05±0.20° and 28.04±0.20°.

In some embodiments of the present invention, the X-ray powder diffraction pattern of the above-mentioned crystal form G has characteristic diffraction peaks at the following 2θangles: 11.98±0.20°, 12.39±0.20°, 14.79±0.20°, 16.53±0.20°, 17.90±0.20°, 21.56±0.20°, 23.36±0.20°, 24.05±0.20°, 24.58±0.20°, 25.27±0.20°, 26.81±0.20° and 28.04±0.20°.

In some embodiments of the present invention, the XRPD pattern of the above-mentioned crystal form G is as shown in FIG. 13.

In some embodiments of the present invention, the XRPD pattern analysis data of the above-mentioned crystal form G are as shown in Table 7:

TABLE 7

| XRPD pattern analysis data of crystal form G of compound of Formula (II-1) | | | |
|---|---|---|---|
| No. | 2θ angle (°) | Interplanar spacing (Å) | Relative intensity (%) |
| 1 | 8.39 | 10.53 | 13.81 |
| 2 | 9.69 | 9.12 | 31.81 |
| 3 | 10.00 | 8.84 | 21.65 |
| 4 | 10.75 | 8.23 | 3.05 |
| 5 | 11.98 | 7.39 | 98.03 |
| 6 | 12.39 | 7.14 | 65.46 |
| 7 | 14.79 | 5.99 | 43.33 |
| 8 | 15.38 | 5.76 | 35.09 |
| 9 | 16.53 | 5.36 | 53.85 |
| 10 | 16.79 | 5.28 | 36.37 |
| 11 | 17.03 | 5.21 | 34.60 |
| 12 | 17.32 | 5.12 | 24.98 |
| 13 | 17.90 | 4.96 | 89.06 |
| 14 | 18.36 | 4.83 | 33.70 |
| 15 | 19.26 | 4.61 | 16.90 |
| 16 | 20.05 | 4.43 | 28.88 |
| 17 | 21.17 | 4.20 | 81.64 |
| 18 | 21.56 | 4.12 | 100.00 |
| 19 | 23.36 | 3.81 | 67.01 |
| 20 | 24.05 | 3.70 | 72.75 |
| 21 | 24.58 | 3.62 | 48.17 |
| 22 | 25.27 | 3.52 | 38.18 |
| 23 | 25.61 | 3.48 | 33.34 |
| 24 | 26.55 | 3.36 | 33.85 |
| 25 | 26.81 | 3.33 | 50.28 |
| 26 | 27.29 | 3.27 | 18.62 |
| 27 | 28.04 | 3.18 | 51.05 |
| 28 | 29.34 | 3.04 | 11.54 |

TABLE 7-continued

| XRPD pattern analysis data of crystal form G of compound of Formula (II-1) | | | |
|---|---|---|---|
| No. | 2θ angle (°) | Interplanar spacing (Å) | Relative intensity (%) |
| 29 | 30.28 | 2.95 | 21.47 |
| 30 | 31.39 | 2.85 | 16.47 |
| 31 | 32.96 | 2.72 | 6.35 |
| 32 | 33.86 | 2.65 | 7.56 |
| 33 | 35.21 | 2.55 | 2.27 |
| 34 | 35.85 | 2.51 | 3.93 |
| 35 | 38.85 | 2.32 | 4.07 |

In some embodiments of the present invention, the thermogravimetric analysis curve of the above-mentioned crystal form G shows a weight loss of 4.11% at 110.0±3° C.

In some embodiments of the present invention, the TGA spectrum of the above-mentioned crystal form G is as shown in FIG. 14.

The present invention provides crystal form H of the compound of Formula (II-1), characterized in that the X-ray powder diffraction pattern of the crystal form H has characteristic diffraction peaks at the following 2θangles: 4.90±0.20°, 12.05±0.20° and 18.24±0.20°.

In some embodiments of the present invention, the X-ray powder diffraction pattern of the above-mentioned crystal form H has characteristic diffraction peaks at the following 2θangles: 4.90±0.20°, 6.49±0.20°, 12.05±0.20°, 16.75±0.20°, 18.24±0.20°, 19.55±0.20°, 20.22±0.20° and 22.06±0.20°.

In some embodiments of the present invention, the XRPD pattern of the above-mentioned crystal form H is as shown in FIG. 15.

In some embodiments of the present invention, the XRPD pattern analysis data of the above-mentioned crystal form H are as shown in Table 8:

TABLE 8

| XRPD pattern analysis data of crystal form H of compound of Formula (II-1) | | | |
|---|---|---|---|
| No. | 2θ angle (°) | Interplanar spacing (Å) | Relative intensity (%) |
| 1 | 4.90 | 18.03 | 100.00 |
| 2 | 6.49 | 13.61 | 28.50 |
| 3 | 9.75 | 9.07 | 11.01 |
| 4 | 12.05 | 7.34 | 82.05 |
| 5 | 13.52 | 6.55 | 13.22 |
| 6 | 14.61 | 6.06 | 5.90 |
| 7 | 15.72 | 5.64 | 9.58 |
| 8 | 16.75 | 5.29 | 33.92 |
| 9 | 18.24 | 4.86 | 76.06 |
| 10 | 19.55 | 4.54 | 68.17 |
| 11 | 20.22 | 4.39 | 21.47 |
| 12 | 22.06 | 4.03 | 32.29 |
| 13 | 22.74 | 3.91 | 12.94 |
| 14 | 24.06 | 3.70 | 15.57 |
| 15 | 24.57 | 3.62 | 18.35 |
| 16 | 26.28 | 3.39 | 4.71 |
| 17 | 27.47 | 3.25 | 7.06 |

In some embodiments of the present invention, the thermogravimetric analysis curve of the above-mentioned crystal form H shows a weight loss of 2.47% at 160.0±3° C.

In some embodiments of the present invention, the TGA spectrum of the above-mentioned crystal form H is as shown in FIG. 16.

The present invention provides crystal form I of the compound of Formula (III-1), characterized in that the X-ray powder diffraction pattern of the crystal form I has characteristic diffraction peaks at the following 2θangles: 4.84±0.20°, 19.22±0.20° and 19.72±0.20°.

(III-1)

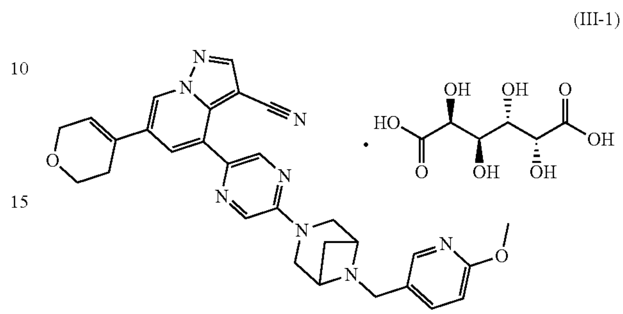

In some embodiments of the present invention, the X-ray powder diffraction pattern of the above-mentioned crystal form I has characteristic diffraction peaks at the following 2θangles: 4.84±0.20°, 12.84±0.20°, 13.42±0.20°, 14.40±0.20°, 19.22±0.20°, 19.72±0.20°, 22.46±0.20° and 30.87±0.20°.

In some embodiments of the present invention, the X-ray powder diffraction pattern of the above-mentioned crystal form I has characteristic diffraction peaks at the following 2θangles: 4.84±0.20°, 12.84±0.20°, 13.42±0.20°, 14.40±0.20°, 15.80±0.20°, 16.89±0.20°, 18.21±0.20°, 19.22±0.20°, 19.72±0.20°, 22.46±0.20°, 24.94±0.20° and 30.87±0.20°.

In some embodiments of the present invention, the XRPD pattern of the above-mentioned crystal form I is as shown in FIG. 17.

In some embodiments of the present invention, the XRPD pattern analysis data of the above-mentioned crystal form I are as shown in Table 9:

TABLE 9

| XRPD pattern analysis data of crystal form I of compound of Formula (III-1) | | | |
|---|---|---|---|
| No. | 2θ angle (°) | Interplanar spacing (Å) | Relative intensity (%) |
| 1 | 4.84 | 18.25 | 100.00 |
| 2 | 6.90 | 12.81 | 4.48 |
| 3 | 7.52 | 11.75 | 2.08 |
| 4 | 9.54 | 9.27 | 4.85 |
| 5 | 12.84 | 6.89 | 14.70 |
| 6 | 13.42 | 6.60 | 19.58 |
| 7 | 14.40 | 6.15 | 43.70 |
| 8 | 15.80 | 5.61 | 7.31 |
| 9 | 16.89 | 5.25 | 8.80 |
| 10 | 18.21 | 4.87 | 7.95 |
| 11 | 19.22 | 4.62 | 73.74 |
| 12 | 19.72 | 4.50 | 51.07 |
| 13 | 20.72 | 4.29 | 6.40 |
| 14 | 21.61 | 4.11 | 4.74 |
| 15 | 22.46 | 3.96 | 19.68 |
| 16 | 23.08 | 3.85 | 5.13 |
| 17 | 24.94 | 3.57 | 8.98 |
| 18 | 26.16 | 3.41 | 1.59 |
| 19 | 26.95 | 3.31 | 5.19 |
| 20 | 28.67 | 3.11 | 2.96 |
| 21 | 29.82 | 3.00 | 2.01 |
| 22 | 30.87 | 2.90 | 11.24 |
| 23 | 33.91 | 2.64 | 3.08 |

TABLE 9-continued

| XRPD pattern analysis data of crystal form I of compound of Formula (III-1) | | | |
|---|---|---|---|
| No. | 2θ angle (°) | Interplanar spacing (Å) | Relative intensity (%) |
| 24 | 34.60 | 2.59 | 3.02 |
| 25 | 36.84 | 2.44 | 1.94 |
| 26 | 37.76 | 2.38 | 2.98 |

In some embodiments of the present invention, the differential scanning calorimetry curve of the above-mentioned crystal form I has a starting point of an endothermic peak at 203.6±2° C.

In some embodiments of the present invention, the DSC thermogram of the above-mentioned crystal form I is as shown in FIG. 18.

In some embodiments of the present invention, the thermogravimetric analysis curve of the above-mentioned crystal form I shows a weight loss of 2.04% at 180.0±3° C.

In some embodiments of the present invention, the TGA spectrum of the above-mentioned crystal form I is as shown in FIG. 19.

The present invention provides crystal form J of the compound of Formula (IV-1), characterized in that the X-ray powder diffraction pattern of the crystal form J has characteristic diffraction peaks at the following 2θangles: 8.62±0.20°, 11.12±0.20° and 17.11±0.20°.

(IV-1)

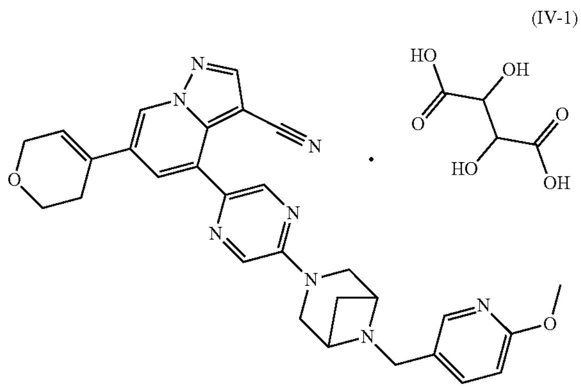 [SMILES: COc1ccc(CN2C3CC2CN(c2cnc(-c4cc(C5=CCOCC5)cn5ncc(C#N)c45)cn2)C3)cn1 ; O=C(O)C(O)C(O)C(=O)O]

In some embodiments of the present invention, the X-ray powder diffraction pattern of the above-mentioned crystal form J has characteristic diffraction peaks at the following 2θangles: 6.53±0.20°, 8.62±0.20°, 11.12±0.20°, 12.26±0.20°, 17.11±0.20°, 19.71±0.20° and 21.77±0.20°.

In some embodiments of the present invention, the XRPD pattern of the above-mentioned crystal form J is as shown in FIG. 20.

In some embodiments of the present invention, the XRPD pattern analysis data of the above-mentioned crystal form J are as shown in Table 10:

TABLE 10

| XRPD pattern analysis data of crystal form J of compound of Formula (IV-1) | | | |
|---|---|---|---|
| No. | 2θ angle (°) | Interplanar spacing (Å) | Relative intensity (%) |
| 1 | 6.53 | 13.53 | 41.15 |
| 2 | 8.62 | 10.25 | 73.88 |

TABLE 10-continued

| XRPD pattern analysis data of crystal form J of compound of Formula (IV-1) | | | |
|---|---|---|---|
| No. | 2θ angle (°) | Interplanar spacing (Å) | Relative intensity (%) |
| 3 | 11.12 | 7.95 | 62.65 |
| 4 | 12.26 | 7.22 | 26.72 |
| 5 | 17.11 | 5.18 | 100.00 |
| 6 | 19.71 | 4.50 | 58.00 |
| 7 | 21.77 | 4.08 | 16.94 |

In some embodiments of the present invention, the thermogravimetric analysis curve of the above-mentioned crystal form J shows a weight loss of 4.67% at 130.0±3° C.

In some embodiments of the present invention, the TGA spectrum of the above-mentioned crystal form J is as shown in FIG. 21.

The present invention provides crystal form K of the compound of Formula (V-1), characterized in that the X-ray powder diffraction pattern of the crystal form K has characteristic diffraction peaks at the following 2θangles: 12.63±0.20°, 17.95±0.20° and 21.66±0.20°.

(V-1)

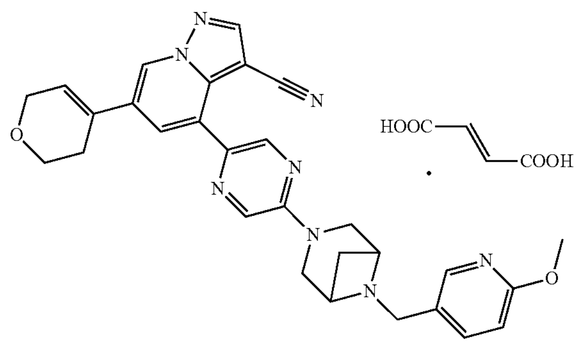

In some embodiments of the present invention, the X-ray powder diffraction pattern of the above-mentioned crystal form K has characteristic diffraction peaks at the following 2θangles: 12.63±0.20°, 15.47±0.20°, 16.27±0.20°, 17.49±0.20°, 17.95±0.20°, 19.13±0.20°, 21.66±0.20° and 24.99±0.20°.

In some embodiments of the present invention, the X-ray powder diffraction pattern of the above-mentioned crystal form K has characteristic diffraction peaks at the following 2θangles: 10.21±0.20°, 12.63±0.20°, 15.47±0.20°, 16.27±0.20°, 17.95±0.20°, 19.13±0.20°, 20.00±0.20°, 21.66±0.20°, 22.51±0.20°, 23.97±0.20°, 24.99±0.20° and 28.39±0.20°.

In some embodiments of the present invention, the XRPD pattern of the above-mentioned crystal form K is as shown in FIG. 22.

In some embodiments of the present invention, the XRPD pattern analysis data of the above-mentioned crystal form K are as shown in Table 11:

TABLE 11

| XRPD pattern analysis data of crystal form K of compound of Formula (V-1) | | | |
|---|---|---|---|
| No. | 2θ angle (°) | Interplanar spacing (Å) | Relative intensity (%) |
| 1 | 3.41 | 25.95 | 24.24 |
| 2 | 7.75 | 11.41 | 12.28 |
| 3 | 8.94 | 9.89 | 18.38 |
| 4 | 9.55 | 9.26 | 14.67 |
| 5 | 10.21 | 8.67 | 33.23 |
| 6 | 12.63 | 7.01 | 100 |
| 7 | 14.86 | 5.96 | 25.29 |
| 8 | 15.47 | 5.73 | 64.05 |
| 9 | 16.27 | 5.45 | 71.82 |
| 10 | 17.49 | 5.07 | 46.89 |
| 11 | 17.95 | 4.94 | 95.39 |
| 12 | 18.33 | 4.84 | 76.37 |
| 13 | 19.13 | 4.64 | 38.03 |
| 14 | 20 | 4.44 | 27.28 |
| 15 | 20.73 | 4.29 | 15.77 |
| 16 | 21.66 | 4.1 | 95.2 |
| 17 | 22.51 | 3.95 | 27.09 |
| 18 | 23.97 | 3.71 | 28.46 |
| 19 | 24.61 | 3.62 | 34.86 |
| 20 | 24.99 | 3.56 | 83.49 |
| 21 | 26.61 | 3.35 | 23.27 |
| 22 | 27.73 | 3.22 | 15.32 |
| 23 | 28.39 | 3.14 | 25.95 |
| 24 | 29.47 | 3.03 | 13.12 |
| 25 | 31.69 | 2.82 | 8 |
| 26 | 32.59 | 2.75 | 6.95 |
| 27 | 34.37 | 2.61 | 3.25 |
| — | — | — | — |

In some embodiments of the present invention, the thermogravimetric analysis curve of the above-mentioned crystal form K shows a weight loss of 5.03% at 140.0±3° C.

In some embodiments of the present invention, the TGA spectrum of the above-mentioned crystal form K is as shown in FIG. 23.

The present invention provides crystal form L of the compound of Formula (V-1), characterized in that the X-ray powder diffraction pattern of the crystal form L has characteristic diffraction peaks at the following 2θangles: 5.93±0.20°, 13.45±0.20° and 20.70±0.20°.

In some embodiments of the present invention, the X-ray powder diffraction pattern of the above-mentioned crystal form L has characteristic diffraction peaks at the following 2θangles: 5.93±0.20°, 13.45±0.20°, 15.22±0.20°, 17.75±0.20°, 20.70±0.20°, 22.91±0.20°, 26.34±0.20° and 27.80±0.20°.

In some embodiments of the present invention, the X-ray powder diffraction pattern of the above-mentioned crystal form L has characteristic diffraction peaks at the following 2θangles: 5.93±0.20°, 10.37±0.20°, 13.45±0.20°, 15.22±0.20°, 16.70±0.20°, 17.75±0.20°, 18.56±0.20°, 20.70±0.20°, 22.91±0.20°, 25.35±0.20°, 26.34±0.20° and 27.80±0.20°.

In some embodiments of the present invention, the XRPD pattern of the above-mentioned crystal form L is as shown in FIG. 24.

In some embodiments of the present invention, the XRPD pattern analysis data of the above-mentioned crystal form L are as shown in Table 12:

TABLE 12

| XRPD pattern analysis data of crystal form L of compound of Formula (V-1) | | | |
|---|---|---|---|
| No. | 2θ angle (°) | Interplanar spacing (Å) | Relative intensity (%) |
| 1 | 5.93 | 14.91 | 100.00 |
| 2 | 6.95 | 12.71 | 8.59 |
| 3 | 10.37 | 8.53 | 22.76 |
| 4 | 12.57 | 7.04 | 5.80 |
| 5 | 13.45 | 6.58 | 51.75 |
| 6 | 14.23 | 6.22 | 10.66 |
| 7 | 15.22 | 5.82 | 37.71 |
| 8 | 16.70 | 5.31 | 26.66 |
| 9 | 17.14 | 5.17 | 21.13 |
| 10 | 17.75 | 5.00 | 33.68 |
| 11 | 18.56 | 4.78 | 30.09 |
| 12 | 19.34 | 4.59 | 10.14 |
| 13 | 20.07 | 4.42 | 18.38 |
| 14 | 20.70 | 4.29 | 77.37 |
| 15 | 22.55 | 3.94 | 33.77 |
| 16 | 22.91 | 3.88 | 38.52 |
| 17 | 23.22 | 3.83 | 29.82 |
| 18 | 24.46 | 3.64 | 11.96 |
| 19 | 25.35 | 3.51 | 25.79 |
| 20 | 26.34 | 3.38 | 51.84 |
| 21 | 27.80 | 3.21 | 31.35 |
| 22 | 30.46 | 2.93 | 8.29 |
| 23 | 32.12 | 2.79 | 10.12 |
| 24 | 33.31 | 2.69 | 5.83 |
| 25 | 34.81 | 2.58 | 2.38 |
| — | — | — | — |

In some embodiments of the present invention, the thermogravimetric analysis curve of the above-mentioned crystal form L shows a weight loss of 5.24% at 110.0±3° C.

In some embodiments of the present invention, the TGA spectrum of the above-mentioned crystal form L is as shown in FIG. 25.

The present invention provides crystal form M of the compound of Formula (VI-1), characterized in that the X-ray powder diffraction pattern of the crystal form M has characteristic diffraction peaks at the following 2θangles: 8.52±0.20°, 16.75±0.20°, 18.07±0.20° and 21.72±0.20°.

(VI-1)

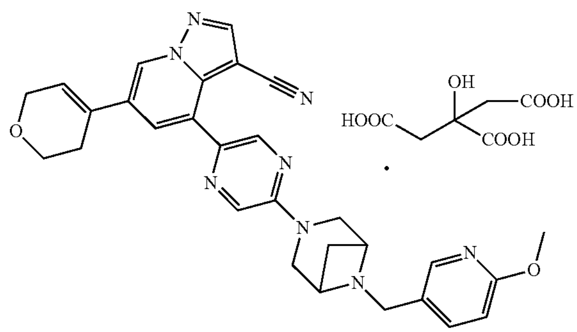

In some embodiments of the present invention, the XRPD pattern of the above-mentioned crystal form M is as shown in FIG. 26.

In some embodiments of the present invention, the XRPD pattern analysis data of the above-mentioned crystal form M are as shown in Table 13:

TABLE 13

| XRPD pattern analysis data of crystal form M of compound of Formula (VI-1) | | | |
|---|---|---|---|
| No. | 2θ angle (°) | Interplanar spacing (Å) | Relative intensity (%) |
| 1 | 8.52 | 10.38 | 100.00 |
| 2 | 16.75 | 5.29 | 27.19 |
| 3 | 18.07 | 4.91 | 49.64 |
| 4 | 21.72 | 4.09 | 53.70 |

In some embodiments of the present invention, the thermogravimetric analysis curve of the above-mentioned crystal form M shows a weight loss of 5.19% at 120.0±3° C.

In some embodiments of the present invention, the TGA spectrum of the above-mentioned crystal form M is as shown in FIG. 27.

The present invention provides crystal form N of the compound of Formula (VII-1), characterized in that the X-ray powder diffraction pattern of the crystal form N has characteristic diffraction peaks at the following 2θangles: 18.53±0.20°, 19.05±0.20° and 19.98±0.20°.

(VII-1)

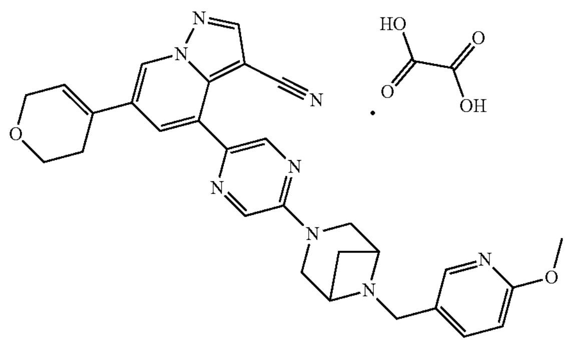

In some embodiments of the present invention, the X-ray powder diffraction pattern of the above-mentioned crystal form N has characteristic diffraction peaks at the following 2θ angles: 9.98±0.20°, 11.71±0.20°, 12.25±0.20°, 13.24±0.20°, 16.19±0.20°, 18.53±0.20°, 19.05±0.20° and 19.98±0.20°.

In some embodiments of the present invention, the X-ray powder diffraction pattern of the above-mentioned crystal form N has characteristic diffraction peaks at the following 2θangles: 5.05±0.20°, 9.98±0.20°, 11.71±0.20°, 12.25±0.20°, 13.24±0.20°, 14.35±0.20°, 16.19±0.20°, 18.53±0.20°, 19.05±0.20°, 19.98±0.20°, 20.91±0.20° and 24.56±0.20°.

In some embodiments of the present invention, the XRPD pattern of the above-mentioned crystal form N is as shown in FIG. 28.

In some embodiments of the present invention, the XRPD pattern analysis data of the above-mentioned crystal form N are as shown in Table 14:

TABLE 14

| XRPD pattern analysis data of crystal form N of compound of Formula (VII-1) | | | |
|---|---|---|---|
| No. | 2θ angle (°) | Interplanar spacing (Å) | Relative intensity (%) |
| 1 | 5.05 | 17.52 | 14.14 |
| 2 | 6.60 | 13.40 | 3.32 |
| 3 | 9.98 | 8.86 | 41.68 |
| 4 | 11.71 | 7.56 | 18.78 |
| 5 | 12.25 | 7.22 | 42.01 |
| 6 | 13.24 | 6.69 | 24.39 |
| 7 | 14.35 | 6.17 | 11.16 |
| 8 | 16.19 | 5.48 | 18.72 |
| 9 | 17.45 | 5.08 | 3.80 |
| 10 | 18.53 | 4.79 | 58.89 |
| 11 | 19.05 | 4.66 | 100.00 |
| 12 | 19.98 | 4.44 | 59.47 |
| 13 | 20.91 | 4.25 | 14.92 |
| 14 | 23.33 | 3.81 | 9.91 |
| 15 | 24.56 | 3.62 | 11.38 |
| 16 | 25.43 | 3.50 | 8.95 |
| 17 | 30.19 | 2.96 | 8.25 |
| 18 | 32.57 | 2.75 | 3.48 |

In some embodiments of the present invention, the thermogravimetric analysis curve of the above-mentioned crystal form N shows a weight loss of 3.19% at 160.0±3° C.

In some embodiments of the present invention, the TGA spectrum of the above-mentioned crystal form N is as shown in FIG. 29.

The present invention provides crystal form O of the compound of Formula (VII-1), characterized in that the X-ray powder diffraction pattern of the crystal form 0 has characteristic diffraction peaks at the following 2θangles: 10.39±0.20°, 12.98±0.20° and 18.17±0.20°.

In some embodiments of the present invention, the X-ray powder diffraction pattern of the above-mentioned crystal form 0 has characteristic diffraction peaks at the following 2θangles: 10.39±0.20°, 11.33±0.20°, 12.98±0.20°, 15.62±0.20°, 18.17±0.20°, 19.96±0.20°, 21.54±0.20° and 22.91±0.20°.

In some embodiments of the present invention, the X-ray powder diffraction pattern of the above-mentioned crystal form 0 has characteristic diffraction peaks at the following 2θangles: 7.75±0.20°, 10.39±0.20°, 11.33±0.20°, 12.98±0.20°, 15.62±0.20°, 16.65±0.20°, 18.17±0.20°, 19.04±0.20°, 19.96±0.20°, 21.54±0.20°, 22.91±0.20° and 24.05±0.20°.

In some embodiments of the present invention, the XRPD pattern of the above-mentioned crystal form 0 is as shown in FIG. 30.

In some embodiments of the present invention, the XRPD pattern analysis data of the above-mentioned crystal form 0 are as shown in Table 15:

TABLE 15

| XRPD pattern analysis data of crystal form O of compound of Formula (VII-1) | | | |
|---|---|---|---|
| No. | 2θ angle (°) | Interplanar spacing (Å) | Relative intensity (%) |
| 1 | 7.75 | 11.41 | 13.69 |
| 2 | 10.39 | 8.52 | 67.78 |
| 3 | 10.75 | 8.23 | 45.49 |
| 4 | 11.33 | 7.81 | 22.20 |
| 5 | 12.98 | 6.82 | 35.83 |

TABLE 15-continued

| XRPD pattern analysis data of crystal form O of compound of Formula (VII-1) | | | |
|---|---|---|---|
| No. | 2θ angle (°) | Interplanar spacing (Å) | Relative intensity (%) |
| 6 | 15.62 | 5.67 | 28.66 |
| 7 | 16.65 | 5.32 | 17.13 |
| 8 | 18.17 | 4.88 | 100.00 |
| 9 | 19.04 | 4.66 | 18.03 |
| 10 | 19.96 | 4.45 | 25.11 |
| 11 | 21.54 | 4.13 | 28.93 |
| 12 | 22.91 | 3.88 | 27.79 |
| 13 | 24.05 | 3.70 | 20.71 |
| 14 | 24.39 | 3.65 | 20.59 |
| 15 | 26.61 | 3.35 | 10.03 |
| 16 | 31.49 | 2.84 | 5.78 |

In some embodiments of the present invention, the thermogravimetric analysis curve of the above-mentioned crystal form 0 shows a weight loss of 9.32% at 140.0±3° C.

In some embodiments of the present invention, the TGA spectrum of the above-mentioned crystal form 0 is as shown in FIG. 31.

The present invention provides crystal form P of the compound of Formula (VII-1), characterized in that the X-ray powder diffraction pattern of the crystal form P has characteristic diffraction peaks at the following 2θangles: 6.49±0.20°, 11.83±0.20° and 25.14±0.20°.

In some embodiments of the present invention, the X-ray powder diffraction pattern of the above-mentioned crystal form P has characteristic diffraction peaks at the following 2θangles: 6.49±0.20°, 7.79±0.20°, 10.90±0.20°, 11.83±0.20°, 12.87±0.20°, 14.82±0.20°, 18.53±0.20° and 25.14±0.20°.

In some embodiments of the present invention, the XRPD pattern of the above-mentioned crystal form P is as shown in FIG. 32.

In some embodiments of the present invention, the XRPD pattern analysis data of the above-mentioned crystal form P are as shown in Table 16:

TABLE 16

| XRPD pattern analysis data of crystal form P of compound of Formula (VII-1) | | | |
|---|---|---|---|
| No. | 2θ angle (°) | Interplanar spacing (Å) | Relative intensity (%) |
| 1 | 5.38 | 16.44 | 6.27 |
| 2 | 6.49 | 13.62 | 100.00 |
| 3 | 7.79 | 11.35 | 9.67 |
| 4 | 8.99 | 9.84 | 5.87 |
| 5 | 10.90 | 8.12 | 9.69 |
| 6 | 11.83 | 7.48 | 26.45 |
| 7 | 12.87 | 6.88 | 11.91 |
| 8 | 14.82 | 5.98 | 12.44 |
| 9 | 16.44 | 5.39 | 9.13 |
| 10 | 18.53 | 4.79 | 13.51 |
| 11 | 20.16 | 4.41 | 7.56 |
| 12 | 25.14 | 3.54 | 33.44 |

In some embodiments of the present invention, the thermogravimetric analysis curve of the above-mentioned crystal form P shows a weight loss of 4.58% at 90.0±3° C.

In some embodiments of the present invention, the TGA spectrum of the above-mentioned crystal form P is as shown in FIG. 33.

The present invention provides crystal form Q of the compound of Formula (VIII-1), characterized in that the X-ray powder diffraction pattern of the crystal form Q has characteristic diffraction peaks at the following 2θangles: 3.39±0.20°, 6.75±0.20° and 13.73±0.20°.

(VIII-1)

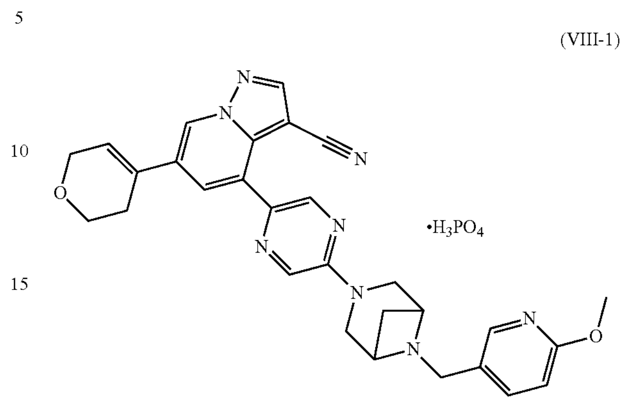

In some embodiments of the present invention, the X-ray powder diffraction pattern of the above-mentioned crystal form Q has characteristic diffraction peaks at the following 2θangles: 3.39±0.20°, 5.88±0.20°, 6.75±0.20°, 7.94±0.20°, 10.72±0.20°, 13.73±0.20°, 16.91±0.20° and 19.15±0.20°.

In some embodiments of the present invention, the X-ray powder diffraction pattern of the above-mentioned crystal form Q has characteristic diffraction peaks at the following 2θangles: 3.39±0.20°, 5.88±0.20°, 6.75±0.20°, 7.94±0.20°, 9.20±0.20°, 10.72±0.20°, 13.73±0.20°, 16.28±0.20°, 16.91±0.20°, 18.51±0.20°, 19.15±0.20° and 21.66±0.20°.

The present invention provides crystal form Q of the compound of Formula (VIII-1), characterized in that the X-ray powder diffraction pattern of the crystal form Q has characteristic diffraction peaks at the following 2θangles: 6.75±0.20°, 10.72±0.20° and 13.73±0.20°.

(VIII-1)

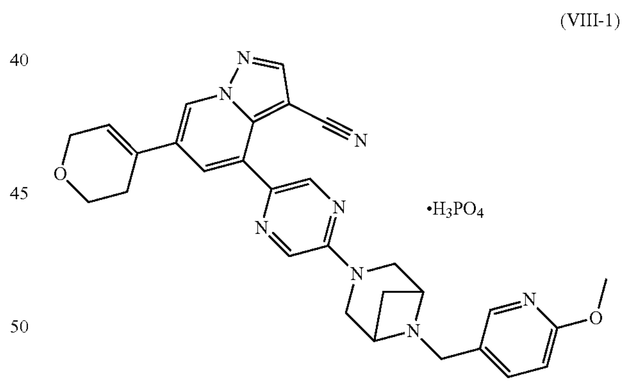

In some embodiments of the present invention, the X-ray powder diffraction pattern of the above-mentioned crystal form Q has characteristic diffraction peaks at the following 2θangles: 5.88±0.20°, 6.75±0.20°, 7.94±0.20°, 10.72±0.20°, 13.73±0.20°, 16.91±0.20°, 19.15±0.20° and 24.60±0.20°.

In some embodiments of the present invention, the X-ray powder diffraction pattern of the above-mentioned crystal form Q has characteristic diffraction peaks at the following 2θangles: 5.88±0.20°, 6.75±0.20°, 7.94±0.20°, 9.20±0.20°, 10.72±0.20°, 13.73±0.20°, 16.28±0.20°, 16.91±0.20°, 18.51±0.20°, 19.15±0.20°, 21.66±0.20° and 24.60±0.20°.

In some embodiments of the present invention, the XRPD pattern of the above-mentioned crystal form Q is as shown in FIG. 34.

In some embodiments of the present invention, the XRPD pattern analysis data of the above-mentioned crystal form Q are as shown in Table 17:

TABLE 17

XRPD pattern analysis data of crystal form Q of compound of Formula (VIII-1)

| No. | 2θ angle (°) | Interplanar spacing (Å) | Relative intensity (%) |
|---|---|---|---|
| 1 | 3.39 | 26.04 | 85.26 |
| 2 | 5.88 | 15.04 | 69.12 |
| 3 | 6.75 | 13.09 | 100.00 |
| 4 | 7.94 | 11.14 | 72.26 |
| 5 | 9.20 | 9.61 | 51.54 |
| 6 | 10.72 | 8.25 | 84.75 |
| 7 | 11.75 | 7.53 | 37.95 |
| 8 | 13.73 | 6.45 | 89.92 |
| 9 | 15.34 | 5.78 | 49.92 |
| 10 | 16.28 | 5.45 | 66.33 |
| 11 | 16.91 | 5.24 | 70.21 |
| 12 | 17.75 | 5.00 | 40.51 |
| 13 | 18.51 | 4.79 | 56.79 |
| 14 | 19.15 | 4.64 | 71.57 |
| 15 | 19.86 | 4.47 | 24.12 |
| 16 | 21.66 | 4.10 | 56.33 |
| 17 | 24.60 | 3.62 | 50.68 |
| 18 | 25.30 | 3.52 | 47.68 |

In some embodiments of the present invention, the thermogravimetric analysis curve of the above-mentioned crystal form Q shows a weight loss of 3.96% at 150.0±3° C.

In some embodiments of the present invention, the TGA spectrum of the above-mentioned crystal form Q is as shown in FIG. 35.

The present invention provides crystal form R of the compound of Formula (VIII-1), characterized in that the X-ray powder diffraction pattern of the crystal form R has characteristic diffraction peaks at the following 2θangles: 16.28±0.20°, 21.67±0.20° and 24.59±0.20°.

In some embodiments of the present invention, the X-ray powder diffraction pattern of the above-mentioned crystal form R has characteristic diffraction peaks at the following 2θangles: 14.85±0.20°, 15.49±0.20°, 16.28±0.20°, 18.48±0.20°, 19.13±0.20°, 19.68±0.20°, 21.67±0.20° and 24.59±0.20°.

In some embodiments of the present invention, the X-ray powder diffraction pattern of the above-mentioned crystal form R has characteristic diffraction peaks at the following 2θangles: 9.56±0.20°, 14.85±0.20°, 15.49±0.20°, 16.28±0.20°, 18.48±0.20°, 19.13±0.20°, 19.68±0.20°, 21.67±0.20°, 22.80±0.20°, 23.35±0.20°, 24.59±0.20° and 25.27±0.20°.

In some embodiments of the present invention, the XRPD pattern of the above-mentioned crystal form R is as shown in FIG. 36.

In some embodiments of the present invention, the XRPD pattern analysis data of the above-mentioned crystal form R are as shown in Table 18:

TABLE 18

XRPD pattern analysis data of crystal form R of compound of Formula (VIII-1)

| No. | 2θ angle (°) | Interplanar spacing (Å) | Relative intensity (%) |
|---|---|---|---|
| 1 | 4.68 | 18.89 | 14.38 |
| 2 | 7.76 | 11.40 | 11.72 |
| 3 | 9.56 | 9.25 | 28.34 |
| 4 | 12.58 | 7.04 | 11.92 |
| 5 | 14.85 | 5.97 | 30.43 |
| 6 | 15.49 | 5.72 | 49.93 |
| 7 | 16.28 | 5.45 | 100.00 |
| 8 | 17.64 | 5.03 | 14.01 |
| 9 | 18.48 | 4.80 | 33.99 |
| 10 | 19.13 | 4.64 | 60.42 |
| 11 | 19.68 | 4.51 | 47.13 |
| 12 | 21.67 | 4.10 | 77.93 |
| 13 | 22.80 | 3.90 | 18.37 |
| 14 | 23.35 | 3.81 | 27.82 |
| 15 | 24.59 | 3.62 | 80.16 |
| 16 | 25.27 | 3.52 | 24.63 |
| 17 | 26.51 | 3.36 | 11.37 |
| 18 | 27.74 | 3.22 | 11.74 |
| 19 | 28.32 | 3.15 | 11.58 |
| 20 | 29.03 | 3.08 | 12.15 |
| 21 | 31.68 | 2.82 | 9.09 |

In some embodiments of the present invention, the thermogravimetric analysis curve of the above-mentioned crystal form R shows a weight loss of 2.14% at 160.0±3° C.

In some embodiments of the present invention, the TGA spectrum of the above-mentioned crystal form R is as shown in FIG. 37.

The present invention provides an application of the compounds of Formulas (II) to (VIII) and crystal forms A, B, C, D, E, F, G, H, I, J, K, L, M, N, O, P, Q and R in the preparation of a drug for treating solid tumor.

In some embodiments of the present invention, the above-mentioned solid tumor refers to an RET kinase-associated solid tumor.

Technical Effects

The compounds of the present invention have RET kinase inhibition effects, excellent PK properties and tumor growth inhibition effects, and the crystal forms of the present invention are stable and have good pharmaceutical prospects.

Definitions and Descriptions

Unless otherwise stated, the following terms and phrases used herein are intended to have the following meanings. A specific phrase or term should not be considered uncertain or unclear where no specific definition is given, and should be understood according to its common meaning. Where a trade name appears herein, it is intended to refer to its corresponding product or an active ingredient thereof.

The intermediate compound of the present invention can be prepared by a variety of synthesis methods familiar to those skilled in the art, including the specific embodiments listed below, embodiments formed by combination with other chemical synthesis methods, and equivalent replacements familiar to those skilled in the art. The preferred embodiments include but are not limited to the examples of the present invention.

The chemical reactions in the specific embodiments of the present invention are carried out in suitable solvents, which must be suitable for chemical changes in the present invention and the required reagents and materials. In order to obtain the compounds of the present invention, it is sometimes necessary for those skilled in the art to modify or select the synthesis steps or reaction processes based on the existing embodiments.

The present invention will be described in detail through examples, and these examples do not mean any restrictions on the present invention. The following abbreviations are used in the present invention. OTf stands for trifluoromethylsulfonyl.

All solvents used in the present invention are commercially available and can be used without further purification.

The structures of the compounds of the present invention can be confirmed by conventional methods well known to those skilled in the art. If the present invention relates to the absolute configuration of a compound, the absolute configuration can be confirmed by conventional technical means in the art. Taking single crystal X-ray diffraction method (SXRD) for example, the diffraction intensity data of the cultivated single crystal is collected by Bruker D8 venture diffractometer, wherein the light source is CuKα radiation, and the scanning mode is (p/w scanning. After relevant data is collected, the absolute configuration can be confirmed by further analyzing the crystal structure using a direct method (Shelxs 97).

Compounds are named according to conventional nomenclature principles in the art or by ChemDraw® software, and commercially available compounds are named by catalogue names from suppliers.

X-Ray Powder Diffractometer (XRPD) Method of the Present Invention

The X-ray powder diffraction patterns in the present invention are collected on X'Pert3 X-ray powder diffractometer from Panalytical company. The method parameters of X-ray powder diffraction of the present invention are as follows:

X-ray light source: Cu, Kα

Kα1 (Å): 1.54060; Kα2 (Å): 1.54443

Kα2/Kα1 intensity ratio: 0.50

Voltage: 45 kilovolts (kV)

Current: 40 milliamperes (mA)

Divergent slit: fixed ⅛ degree

Scanning mode: continuous

Scanning range: from 3.0 to 40.0 degrees (2θ angle)

Scanning time per step: 46.665 seconds

Step size: 0.0263 degrees

The X-ray powder diffraction pattern described in the present invention is also collected on DX-2700BH X-ray powder diffractometer from Dandong Haoyuan Instrument Co., Ltd. The method parameters of X-ray powder diffraction of the present invention are as follows:

X ray: Cu, Kα (λ=1.54184 Å)

Light tube voltage: 40 kilovolts (kV)

Light tube current: 30 milliamperes (mA)

Divergent slit: 1 mm

Primary scattering slit: 28 mm

Secondary slit: 28 mm

Detector slit: 0.3 mm

Anti-scattering slit: 1 mm

Scanning axis: θs-θd

Step size: 0.02 degrees

Scanning time: 0.5 s

Scanning range: 3-40 degrees

Differential Scanning Calorimeter (DSC) Method of the Present Invention

The differential scanning calorimetry (DSC) data described in the present invention are collected from Discovery DSC 2500 differential scanning calorimeter from TA Company, the instrument control software is TRIOS, and the analysis software is Universal Analysis. Generally, 1-5 mg of a sample is taken and placed in a covered aluminum crucible, the sample is heated from room temperature to a set temperature at a heating rate of 10° C./min under protection of 50 mL/min dry $N_2$, and at the same time, the heat change of the sample during the heating process was recorded by TA software.

Thermal Gravimetric Analyzer (TGA) Method of the Present Invention

The thermal gravimetric analysis (TGA) data described in the present invention are collected from TA Instruments Q5000 and Discovery TGA 5500 thermal gravimetric analyzers, the instrument control software is Q Series and TRIOS, respectively, and the analysis software is Universal Analysis. Generally, 1-5 mg of a sample is taken and placed in a platinum crucible, and the sample is heated from room temperature to 350° C. at a heating rate of 10° C./min under protection of 50 mL/min dry $N_2$.

Dynamic Vapor Sorption (DVS) Method of the Present Invention

Instrument model: SMS DVS Intrinsic dynamic vapor sorption instrument

Test conditions: A sample (10-15 mg) is taken and placed in a DVS sample tray for testing.

Detailed DVS Parameters are as Follows:

Temperature: 25° C.

Balance: dm/dt=0.01%/min (shortest: 10 min, longest: 180 min)

Drying: at 0% RH for 120 min

RH (%) test gradient: 10%

RH (%) test gradient range: 0%-90%-0%

Hygroscopicity Assessment is Classified as Follows:

| Classification of hygroscopicity | ΔW % |
|---|---|
| Deliquescent | Absorption of enough water to form liquid |
| Highly hygroscopic | ΔW % ≥ 15% |
| Hygroscopic | 15% > ΔW % ≥ 2% |
| Slightly hygroscopic | 2% > ΔW % ≥ 0.2% |
| Non- or almost non-hygroscopic | ΔW % < 0.2% |

Note:
ΔW % represents the hygroscopic weight gain of a sample at 25 ± 1° C. and 80 ± 2% RH.

DETAILED DESCRIPTION

Figure 1:
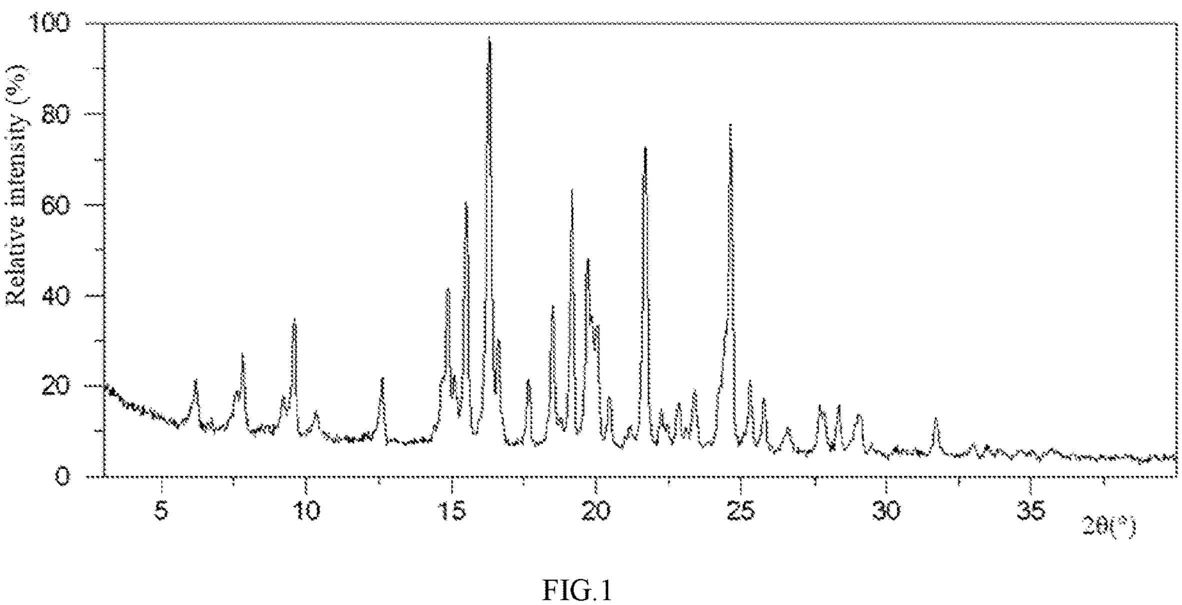
FIG. 1 is a Cu-Kα-radiated XRPD pattern of crystal form A of the compound of formula (I).

In order to better understand the content of the present invention, the present invention will be further illustrated below in conjunction with specific examples, and the specific embodiments are not intended to limit the content of the present invention.

Example 1: Preparation of Compound of Formula (I) and Trifluoroacetate Thereof (I)

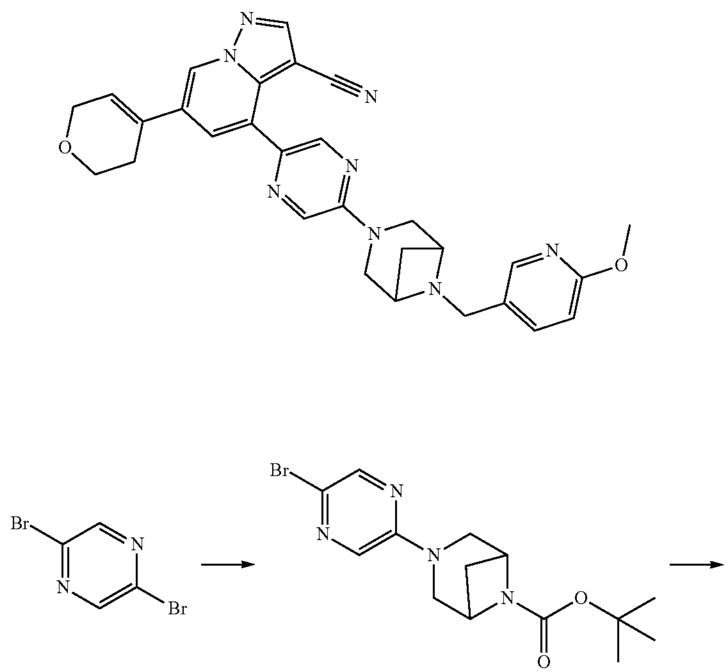

1

-continued

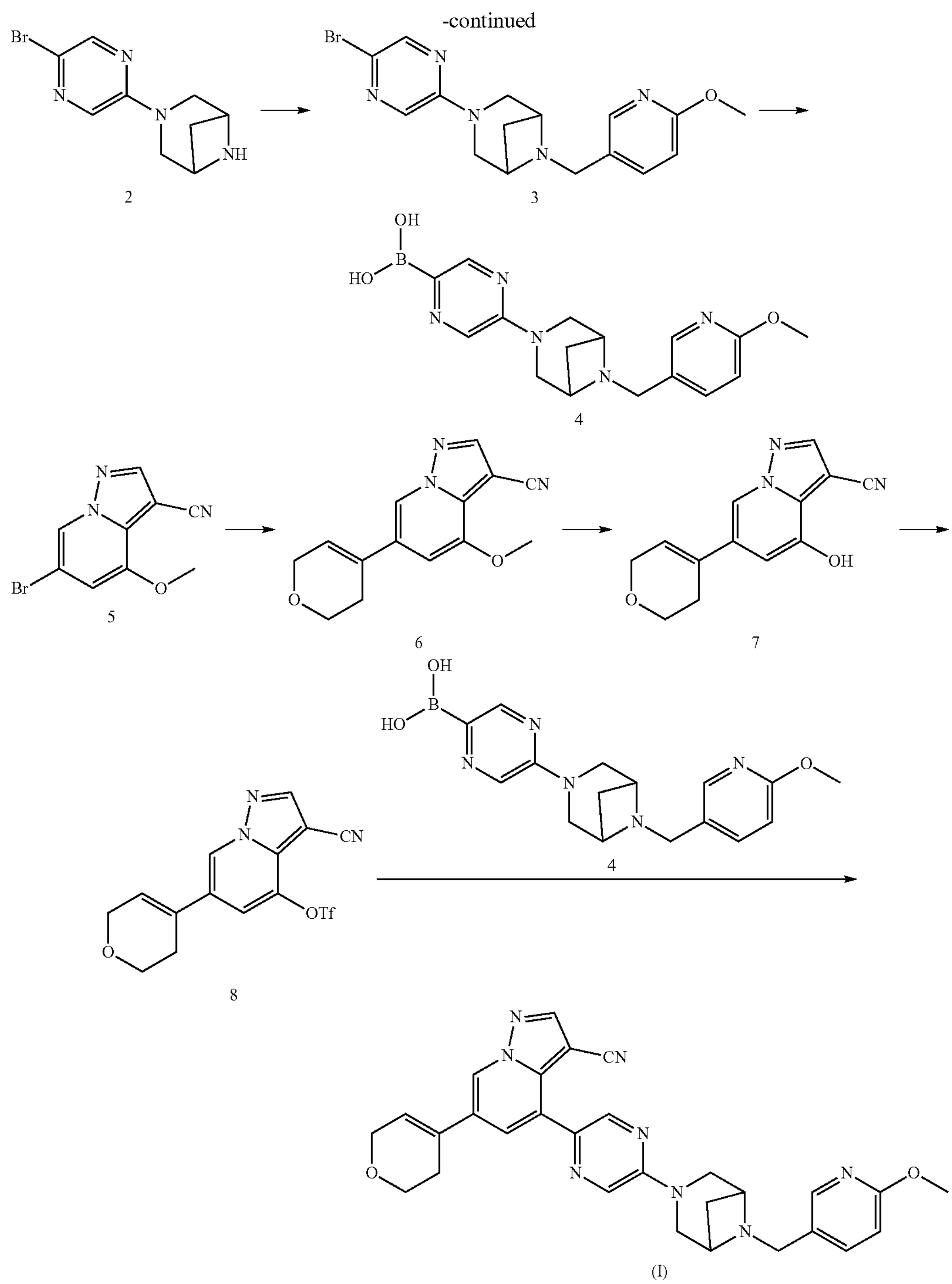

2 3 4 5 6 7 4 8 (I)

Step 1

2,5-dibromopyrazine (4 g, 16.82 mmol) and 6-tert-butyloxycarbonyl-3,6-diazabicyclo[3.1.1]-heptane (4.00 g, 20.18 mmol) were dissolved in N-methylpyrrolidone (50 mL), diisopropylethylamine (6.52 g, 50.45 mmol, 8.79 mL) was added, and the mixture was stirred at 100° C. for 16 hours. 60 mL of water was added, extraction was carried out with ethyl acetate (100 mL×3), the organic phases were combined, washed with water (150 mL×5) and a saturated sodium chloride solution (150 mL×1), and dried over anhydrous sodium sulfate, and finally, the solvent was dried off by spinning to obtain a crude product. The crude product was purified by an automated column chromatography (petroleum ether:ethyl acetate=4:1) to obtain compound 1.

LCMS (ESI) m/z: 354.9 $[M+1]^+$, 356.9 $[M+3]^+$;

$^1$H NMR (400 MHz, $CDCl_3$) δ 8.15 (d, J=1.2 Hz, 1H), 7.77 (s, 1H), 4.28-4.31 (m, 2H), 3.90-4.12 (m, 2H), 3.42 (d, J=12.0 Hz, 2H), 2.64-2.72 (m, 1H), 1.50 (d, J=12.4 Hz, 1H), 1.38 (s, 9H).

Step 2

Compound 1 (3 g, 8.45 mmol) was dissolved in ethyl acetate (15 mL), hydrogen chloride/ethyl acetate (4 M, 20 mL) was added, and the mixture was stirred at 16° C. for 3 hours. The solvent was dried off by spinning to obtain crude product 2, which was directly subjected to the next step of reaction without purification.

LCMS (ESI) m/z: 254.9 $[M+1]^+$, 256.9 $[M+3]^+$.

Step 3

Compound 2 (2.45 g, 8.40 mmol) and 6-methoxy-3-pyridylaldehyde (2.30 g, 16.81 mmol) were added to DCM (50 mL), sodium borohydride acetate (5.34 g, 25.21 mmol) was then added, and the mixture was stirred at 16° C. for 1.5 hours. The reaction liquid became clear. 50 mL of water was added to the reaction liquid, extraction was carried out with dichloromethane (50 mL×3), the organic phases were combined, washed with a saturated sodium chloride solution (100 mL×1), and dried over anhydrous sodium sulfate, and finally, the solvent was dried off by spinning to obtain a crude product. The crude product was purified by an automated column chromatography (petroleum ether:ethyl acetate=1:3 to dichloromethane:methanol=10:1) to obtain compound 3.

LCMS (ESI) m/z: 376.0 $[M+1]^+$, 378.0 $[M+3]^+$.

Step 4

Compound 3 (1.8 g, 4.78 mmol) and bis(pinacolato) diboron (1.82 g, 7.18 mmol) were dissolved in 1,4-dioxane (15 mL), and [1,1'-bis(diphenylphosphino)ferrocene]dichloropalladium(II) (350.05 mg, 478.40 μmol) and potassium acetate (1.41 g, 14.35 mmol) were added, and the mixture was stirred at 80° C. for 16 hours under nitrogen protect ion. Some dehalogenation by-products were obtained in the reaction. The reaction liquid was directly filtered and washed with ethyl acetate twice, and the filtrate was spin-dried to obtain crude product 4, which was directly used for the next step of reaction.

LCMS (ESI) m/z: 342.1 $[M+1]^+$.

Step 5

3,6-Dihydro-2H-pyran-4-boronic acid pinacol ester (1.5 g, 7.14 mmol), compound 5 (1.80 g, 7.14 mmol), [1,1'-bis(diphenylphosphino)ferrocene]dichloropalladium(II) (261.23 mg, 357.01 μmol) and potassium phosphate (4.55 g, 21.42 mmol) were added together to 1,4-dioxane (12 mL) and water (6 mL), then heated to 100° C. by a microwave synthesizer under nitrogen protection and stirred for 30 minutes. 20 mL of water and 20 mL of ethyl acetate were added to the reaction liquid for extraction. After liquid separation, the aqueous phase was then extracted with 20 mL of ethyl acetate, the organic phases were combined and dried over anhydrous sodium sulfate, and the solvent was removed by rotary evaporation to obtain a crude product. The crude product was purified by flash column chromatography on silica gel (petroleum ether/ethyl acetate=1/1) to obtain compound 6.

LCMS (ESI) m/z: 255.9 $[M+1]^+$.

Step 6

Pyridine hydrochloride (4.53 g, 39.17 mmol) was added to compound 6 (1 g, 3.92 mmol), then heated to 180° C. by microwave under nitrogen protection and stirred for 20 minutes. A saturated aqueous sodium bicarbonate solution was added to the reaction liquid until the pH value was 7.50 mL of ethyl acetate was then added for extraction. After liquid separation, the aqueous phase was then extracted with 50 mL of ethyl acetate, the organic phases were combined and dried over anhydrous sodium sulfate, and the solvent was removed by rotary evaporation to obtain crude product 7, which was directly used in the next step without further purification.

Step 7

Compound 7 (460 mg, 1.91 mmol), N-phenyl-bis(trifluoromethanesulfonyl)imide (1.02 g, 2.86 mmol) and diisopropylethylamine (739.31 mg, 5.72 mmol) were added together to N,N-dimethylformamide (10 mL) and then stirred under nitrogen protection at 10-20° C. for 16 hours. The reaction liquid was directly added to 50 mL of water, 20 mL of ethyl acetate was then added for extraction. After liquid separation, the aqueous phase was then extracted with 20 mL of ethyl acetate, the organic phases were combined and dried over anhydrous sodium sulfate, and the solvent was removed by rotary evaporation to obtain crude product 8.

Step 8

Compound 8 (560 mg, 1.50 mmol), compound 4 (511.79 mg, 1.50 mmol), [1,1'-bis(diphenylphosphino)ferrocene]dichloropalladium(II) (54.88 mg, 75.01 μmol) and potassium phosphate (955.27 mg, 4.50 mmol) were added together to 1,4-dioxane (12 mL) and water (6 mL), then heated to 90° C. by a microwave synthesizer under nitrogen protection and reacted with stirred for 0.5 hours. 20 mL of water and 20 mL of ethyl acetate were added to the reaction liquid. After liquid separation, the aqueous phase was then extracted with 20 mL of ethyl acetate, the organic phases were combined and dried over anhydrous sodium sulfate, and rotary evaporation was carried out to obtain crude product of Formula (I). The crude product was purified by a preparative chromatographic column (YMC-Triart Prep C18 150×40 mm×7 μm; mobile phase: [water (0.1% TFA)-ACN]; acetonitrile: 30-40%, 10 min) to obtain a trifluoroacetate of the compound of Formula (I). The trifluoroacetate of the compound of Formula (I) was added to a sodium bicarbonate solution and extracted with ethyl acetate, and the organic phase was dried over anhydrous sodium sulfate and concentrated under reduced pressure to obtain the compound of Formula (I).

LCMS (ESI) m/z: 521.1 [M+1]+;

$^1H$ NMR (400 MHz, $CD_3OD$) δ 8.81-8.80 (m, 1H), 8.71-8.65 (m, 1H), 8.48-8.45 (m, 1H), 8.40-8.30 (m, 2H), 8.00-7.92 (m, 1H), 7.90-7.92 (m, 1H), 6.95-6.92 (m, 2H), 6.53 (s, 1H), 4.74-4.71 (m, 2H), 4.63-4.61 (d, J=8 Hz, 1H), 4.39-4.37 (m, 2H), 4.43-4.30 (m, 3H), 4.10-4.06 (m, 1H), 4.00-3.96 (m, 6H), 3.65-3.62 (m, 1H), 2.62 (s, 2H), 2.25-2.21 (m, 1H).

Example 2: Preparation of Crystal Form a of the Compound of Formula (I)

Figure 2:
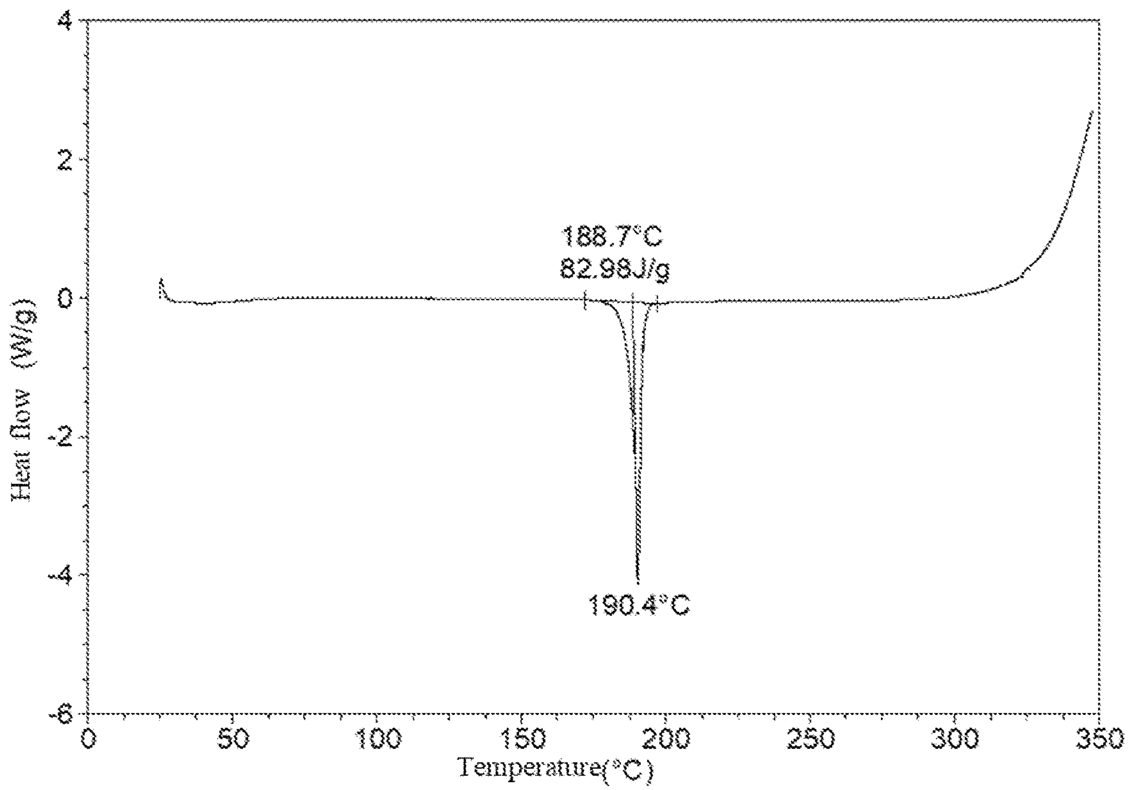
FIG. 2 is a DSC thermogram of crystal form A of the compound of formula (I).
Figure 3:
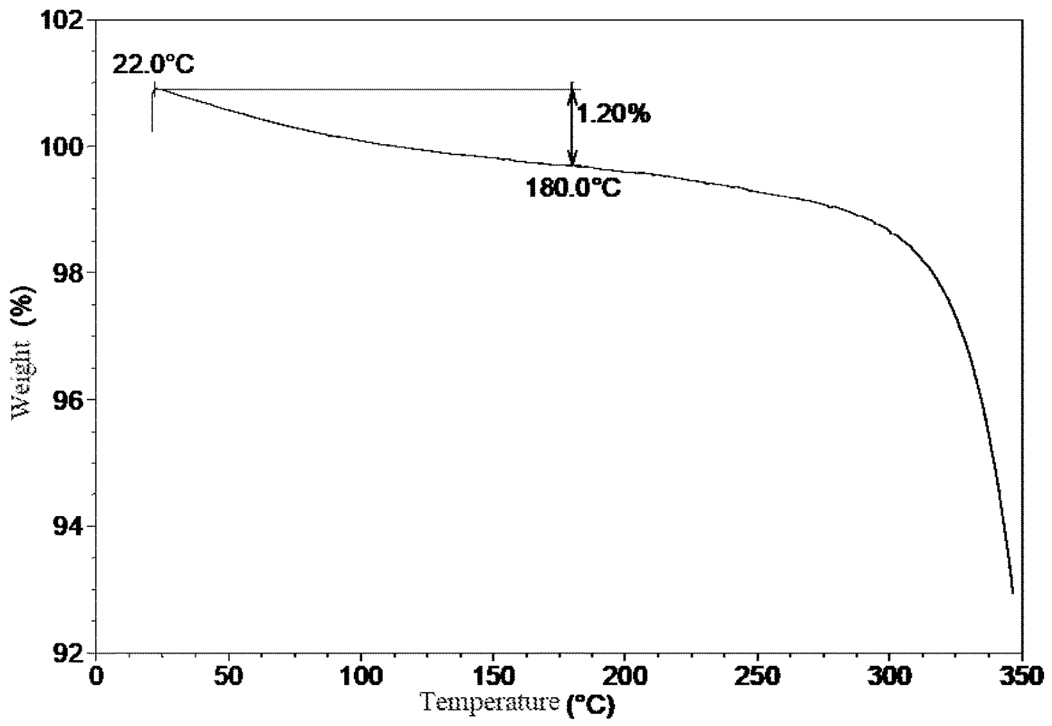
FIG. 3 is a TGA spectrum of crystal form A of the compound of formula (I).

The crude product of Formula (I) was mixed with silica gel and then purified by an automated column chromatography (dichloromethane:methanol=20:1) to obtain the compound of Formula (I), 200 mL of methanol (40 folds) was added to 5 g of the compound of Formula (I) and pulped for 16 hours overnight, and after solid precipitation, filtration was carried out to obtain crystal form A of the compound of Formula (I). The XRPD pattern thereof was as shown in FIG. 1, the DSC thermogram thereof was as shown in FIG. 2, and a TGA spectrum thereof was as shown in FIG. 3.

Figure 39:
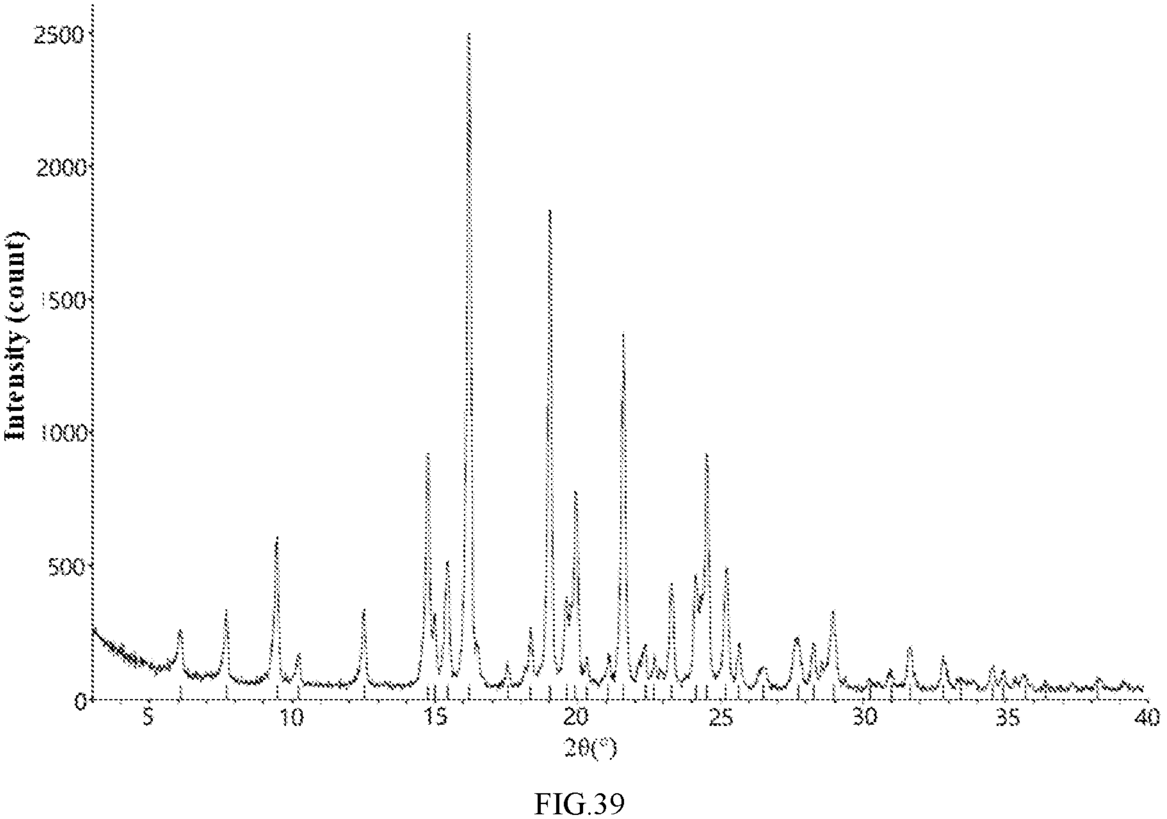
FIG. 39 is a Cu-Kα-radiated XRPD pattern of crystal form A of the compound of formula (I).

About 400 g of the crude product of Formula (I) was added to about 6 L of methanol, stirred at 20-30° C. for 88-96 hours, the reaction liquid was filtered, and the filter cake was rinsed with methanol (0.5 L) and dried in vacuum for 16-24 hours. 5.78 L of purified water was added to the obtained solid, the temperature was controlled at 90-100° C., the mixture was stirred for 24-48 hours and cooled to 20-30° C., and the reaction liquid was filtered and dried in vacuum for 40-96 hours to obtain crystal form A. The XRPD pattern thereof was as shown in FIG. 39.

Example 3: Preparation of Crystal Form B of the Compound of Formula (I)

Figure 4:
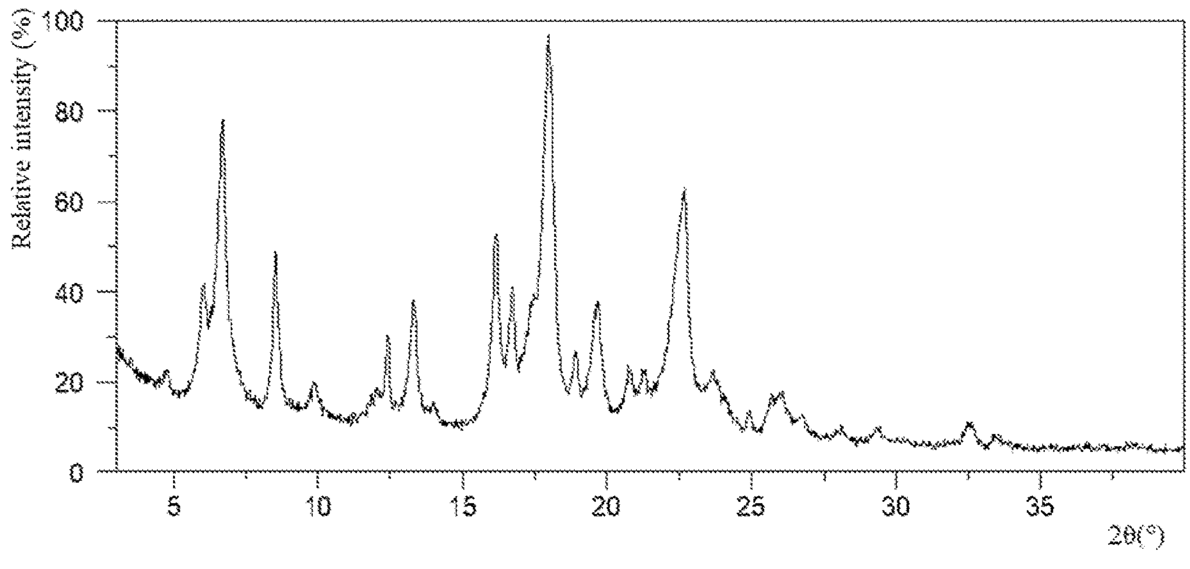
FIG. 4 is a Cu-Kα-radiated XRPD pattern of Cu-Kα radiation of crystal form B of the compound of formula (I).

The compound of Formula (I) (20.9 mg) was added to 1.0 mL of 1,4-dioxane and stirred at room temperature to obtain a suspension, and after centrifugal separation and drying, a solid, i.e., crystal form B of the compound of Formula (I) was obtained. The XRPD pattern thereof was as shown in FIG. 4.

Example 4: Preparation of Crystal Form C of the Compound of Formula (I)

Figure 5:
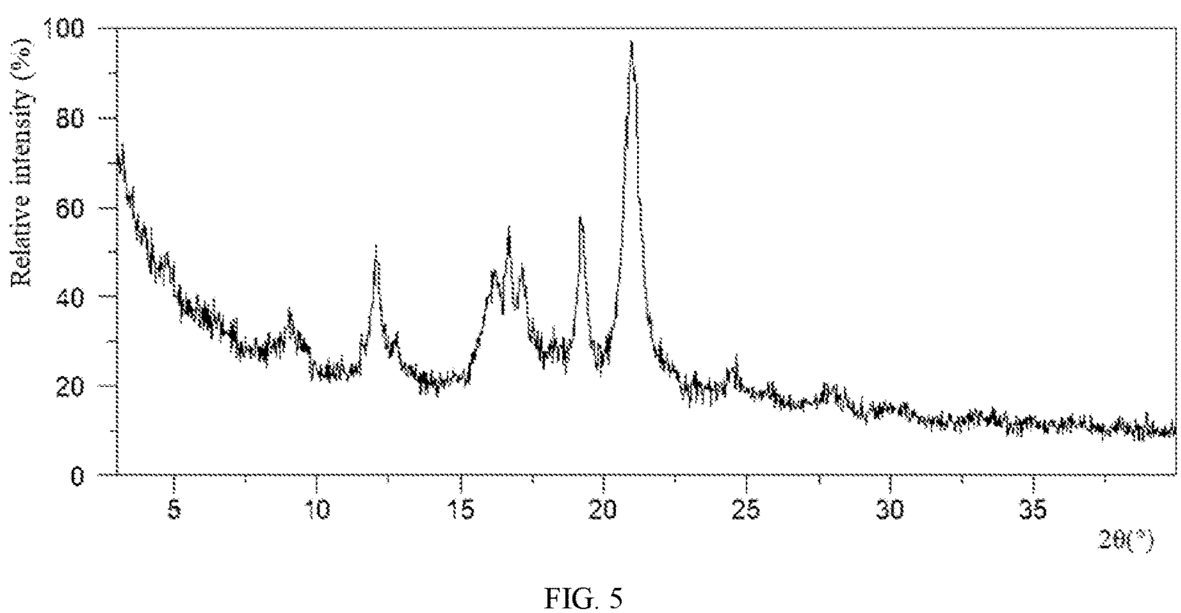
FIG. 5 is a Cu-Kα-radiated XRPD pattern of crystal form C of the compound of formula (I).
Figure 6:
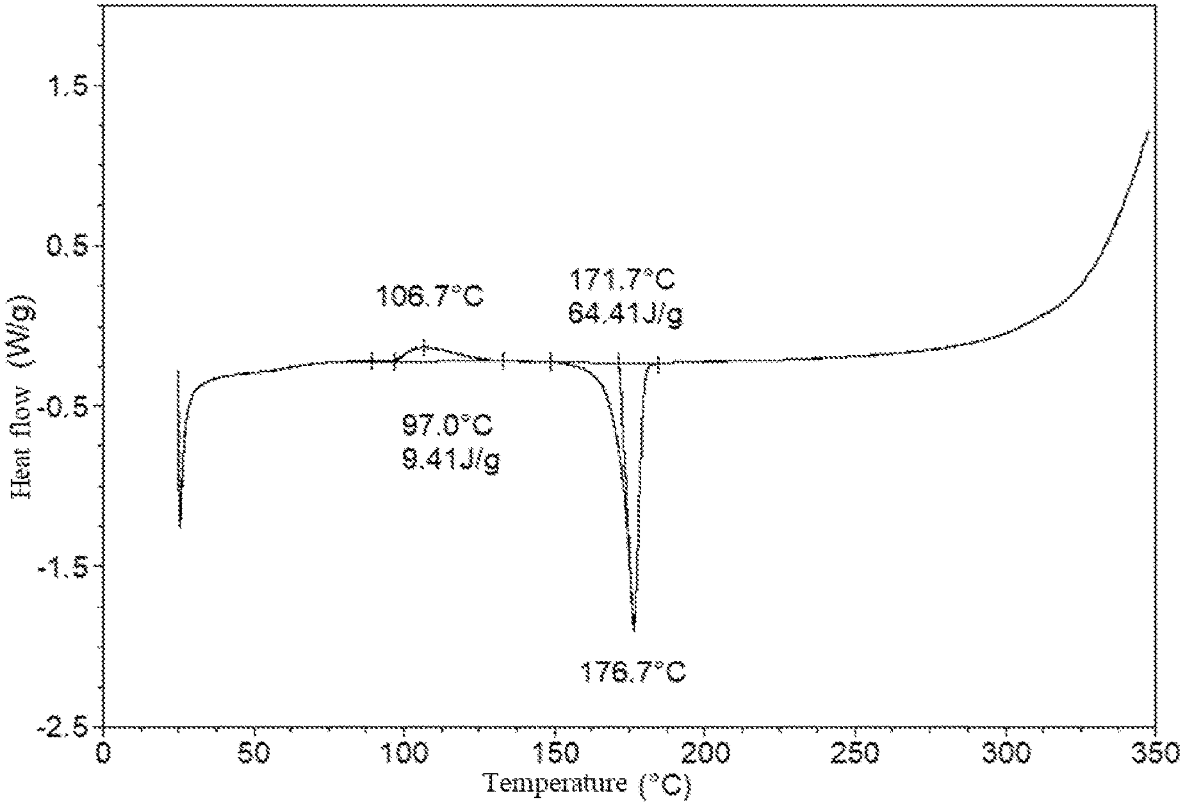
FIG. 6 is a DSC thermogram of crystal form C of the compound of formula (I).
Figure 7:
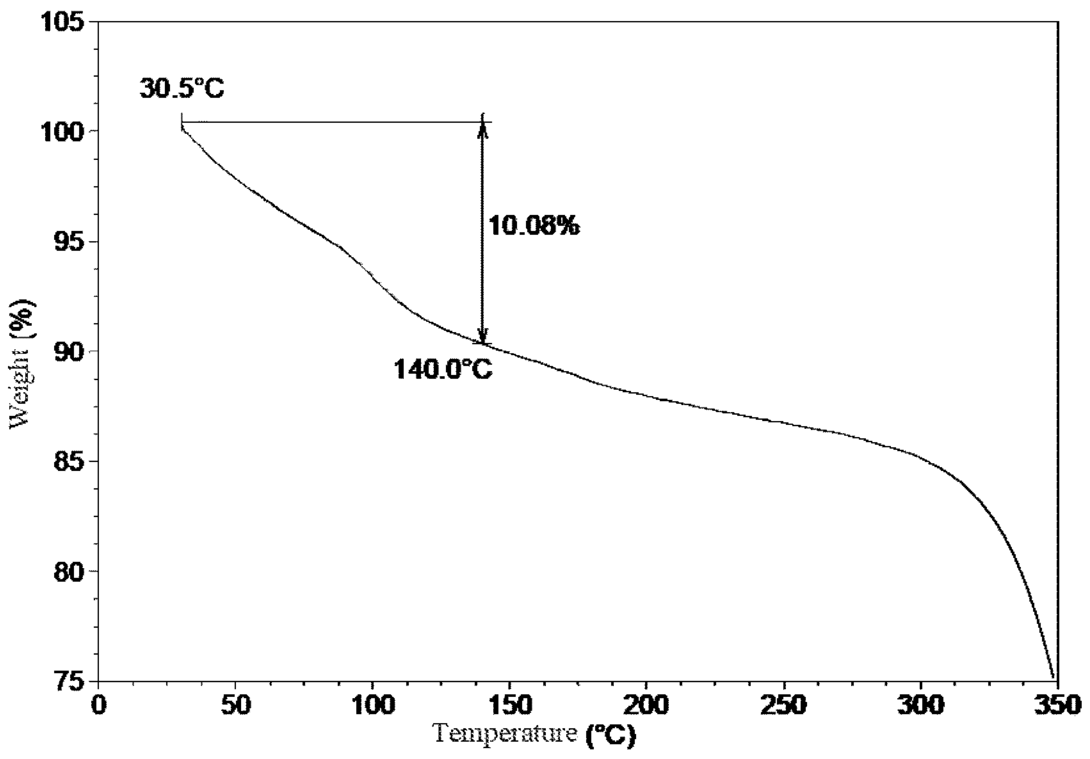
FIG. 7 is a TGA spectrum of crystal form C of the compound of formula (I).

Crystal form B of the compound of Formula (I) was placed in open containers at room temperature overnight to obtain a solid, i.e., crystal form C of the compound of Formula (I). The XRPD pattern thereof was as shown in FIG. 5, the DSC thermogram thereof was as shown in FIG. 6, and the TGA spectrum thereof was as shown in FIG. 7.

Example 5: Preparation of Crystal Form D of the Compound of Formula (I)

Figure 8:
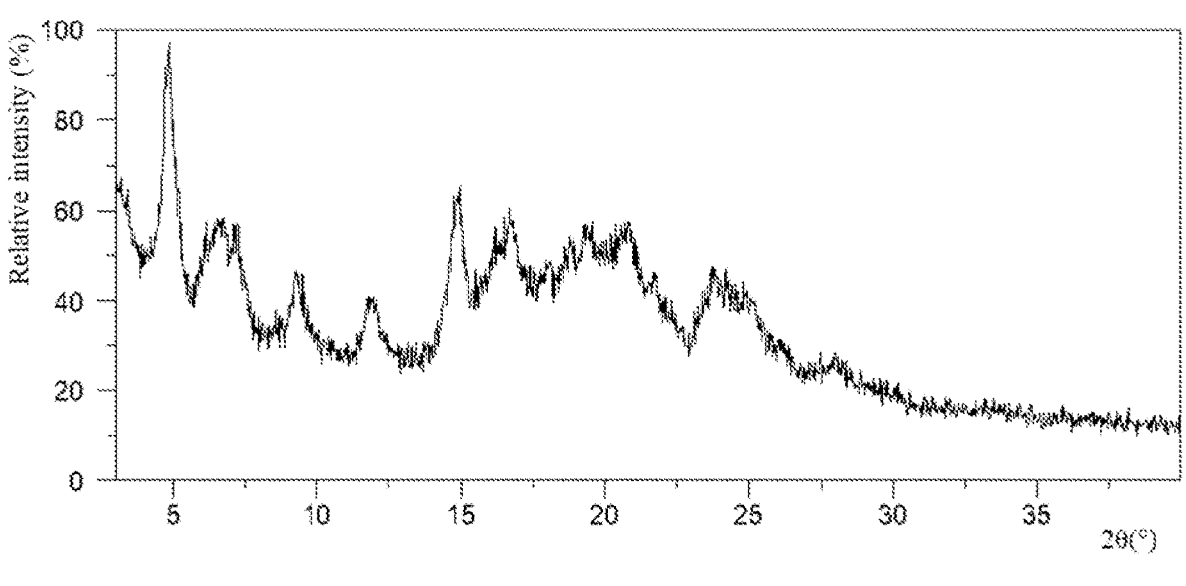
FIG. 8 is a Cu-Kα-radiated XRPD pattern of crystal form D of the compound of formula (I).

Crystal form A of the compound of Formula (I) (20.6 mg) was added to 0.5 mL of 1,4-dioxane/n-butanol (volume ratio 1:1) and stirred at room temperature for 5 days to form a suspension, and after centrifugal separation and drying, a solid, i.e., crystal form D of the compound of Formula (I) was obtained. The XRPD pattern thereof was as shown in FIG. 8.

Example 6: Preparation of Crystal Form E of the Compound of Formula (I)

Figure 9:
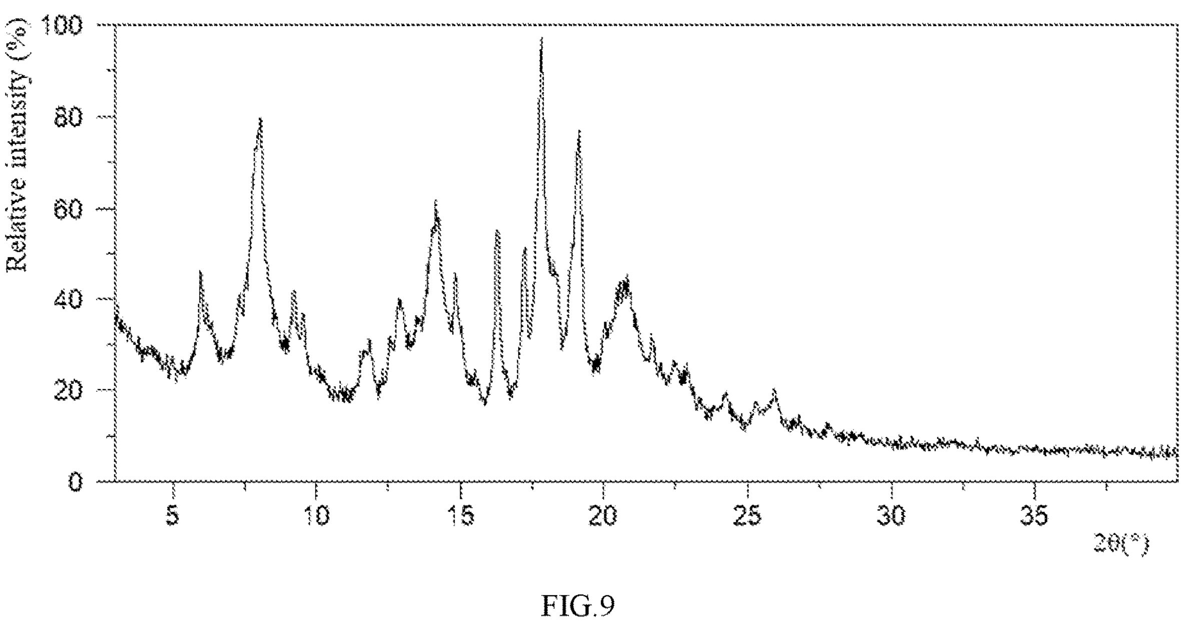
FIG. 9 is a Cu-Kα-radiated XRPD pattern of crystal form E of the compound of formula (I).
Figure 10:
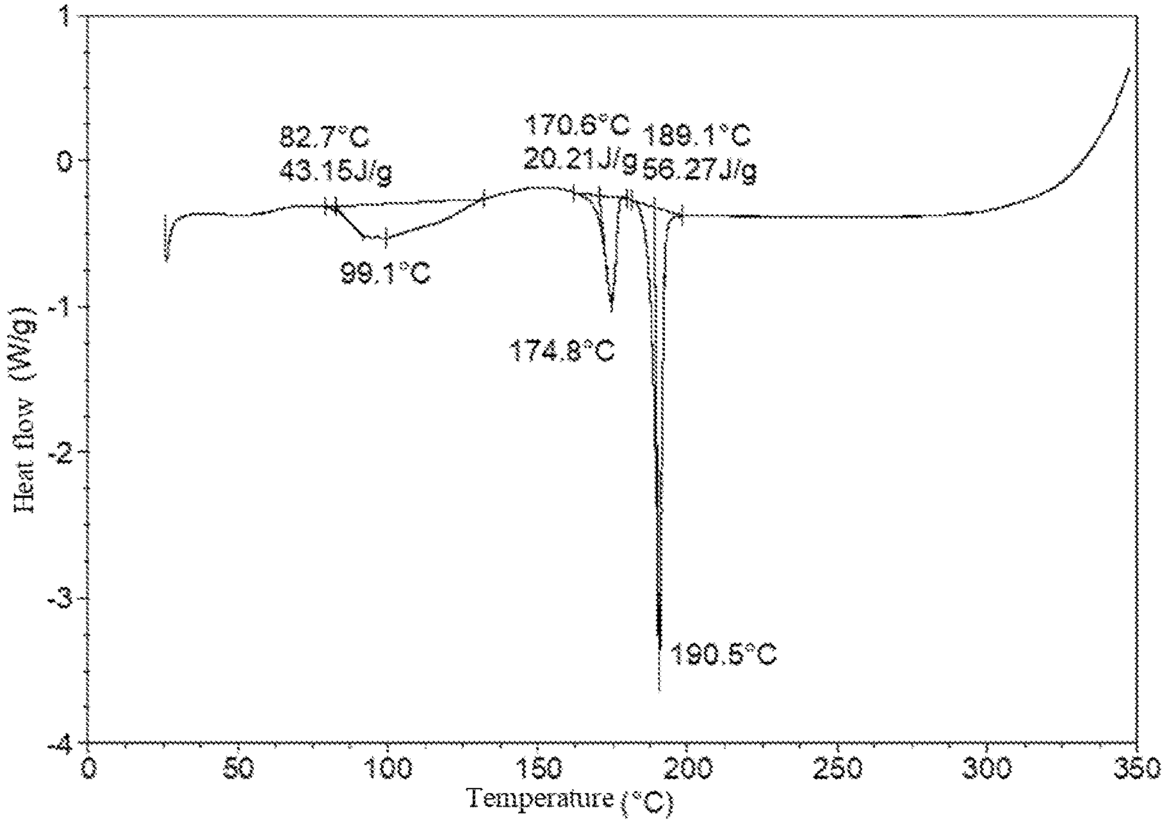
FIG. 10 is a DSC thermogram of crystal form E of the compound of formula (I).
Figure 11:
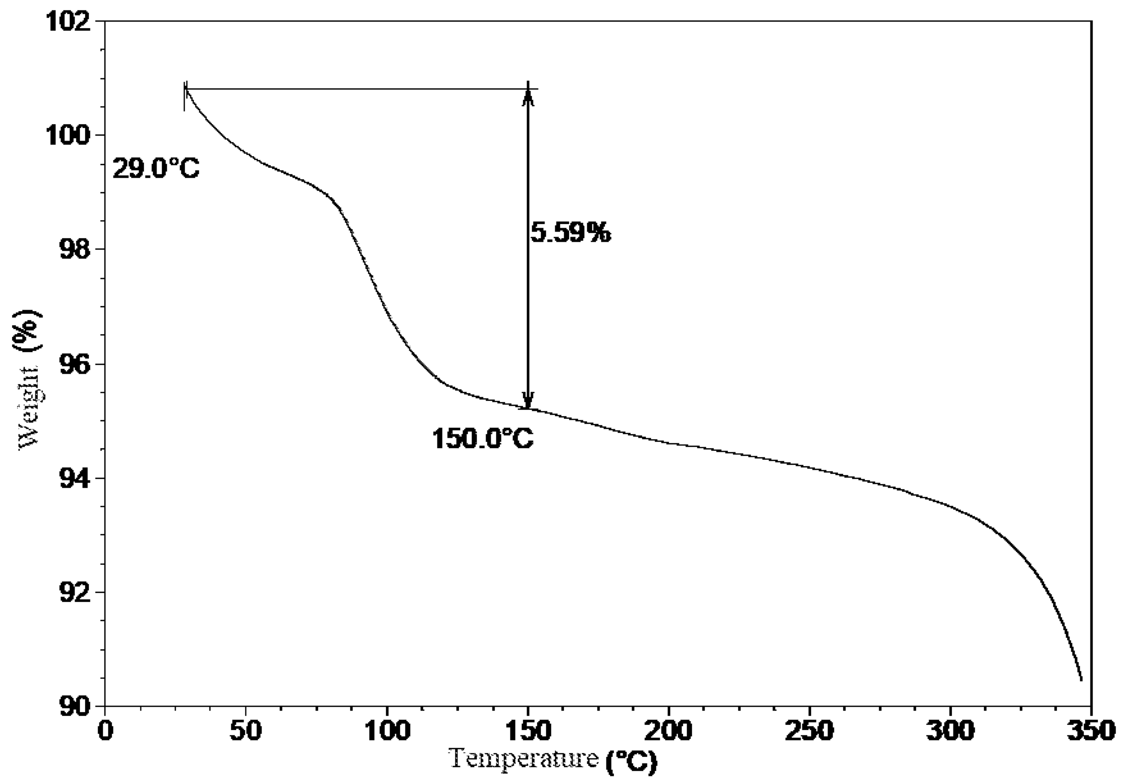
FIG. 11 is a TGA spectrum of crystal form E of the compound of formula (I).

The compound of Formula (I) (20.6 mg) was added to 2.0 mL of acetone and stirred at 50° C. for 1 hour to obtain a suspension, the suspension was filtered to obtain a clear solution, the temperature was reduced from 50° C. to 5° C. within 40 hours to precipitate out a small amount of solid precipitate, the solution was then transferred to −20° C. and a solid was obtained after 6 days, and after centrifugal separation and drying, crystal form E of the compound of Formula (I) was obtained. The XRPD pattern thereof was as shown in FIG. 9, the DSC thermogram thereof was as shown in FIG. 10, and the TGA spectrum thereof was as shown in FIG. 11.

Example 7: Preparation of Crystal Form F of the Compound of Formula (I)

Figure 12:
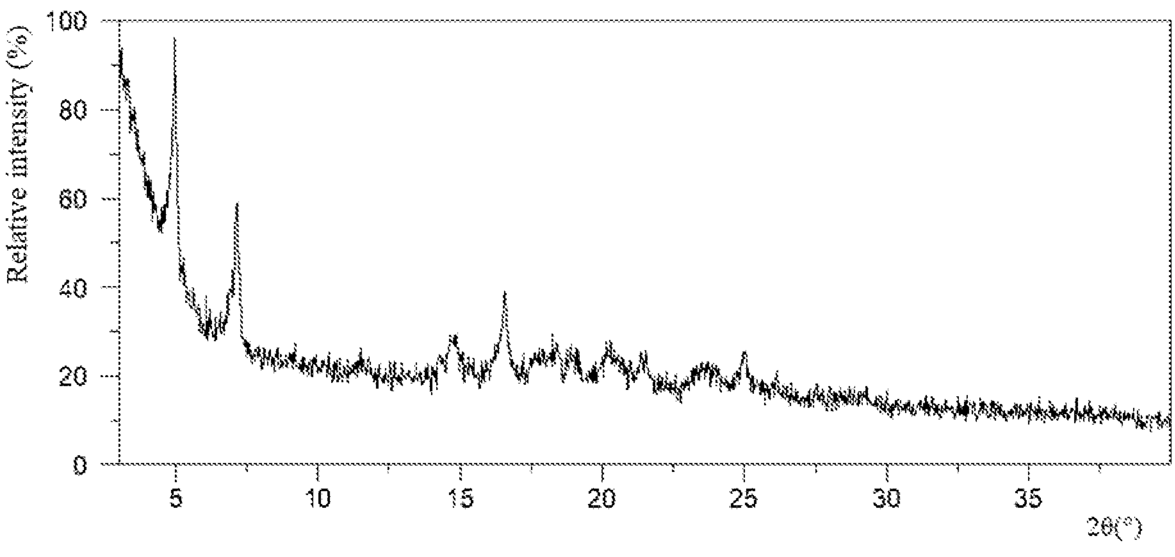
FIG. 12 is a Cu-Kα-radiated XRPD pattern of crystal form F of the compound of formula (I).

The compound of Formula (I) (20.5 mg) was added to 2.0 mL of dimethyl tetrahydrofuran and stirred at 50° C. for 1 hour to obtain a suspension, the suspension was filtered to obtain a clear solution, the temperature was reduced from 50° C. to 5° C. within 40 hours to precipitate out a small amount of solid, the solution was then transferred to −20° C. and a solid was obtained after 6 days, and after centrifugal separation and drying, crystal form F of the compound of Formula (I) was obtained. The XRPD pattern thereof was as shown in FIG. 12.

Example 8: Preparation of Crystal Form G of the Compound of Formula (II-1)

(II-1)

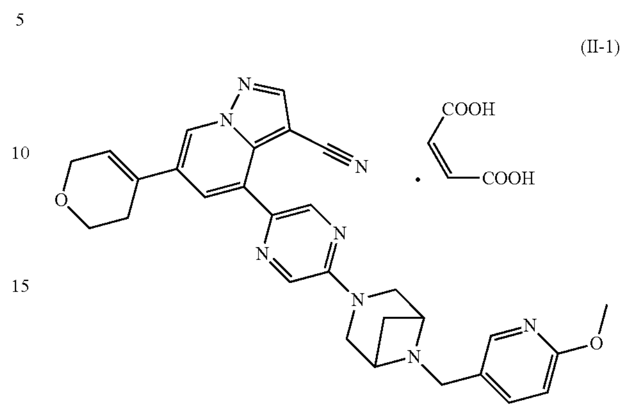

Figure 13:
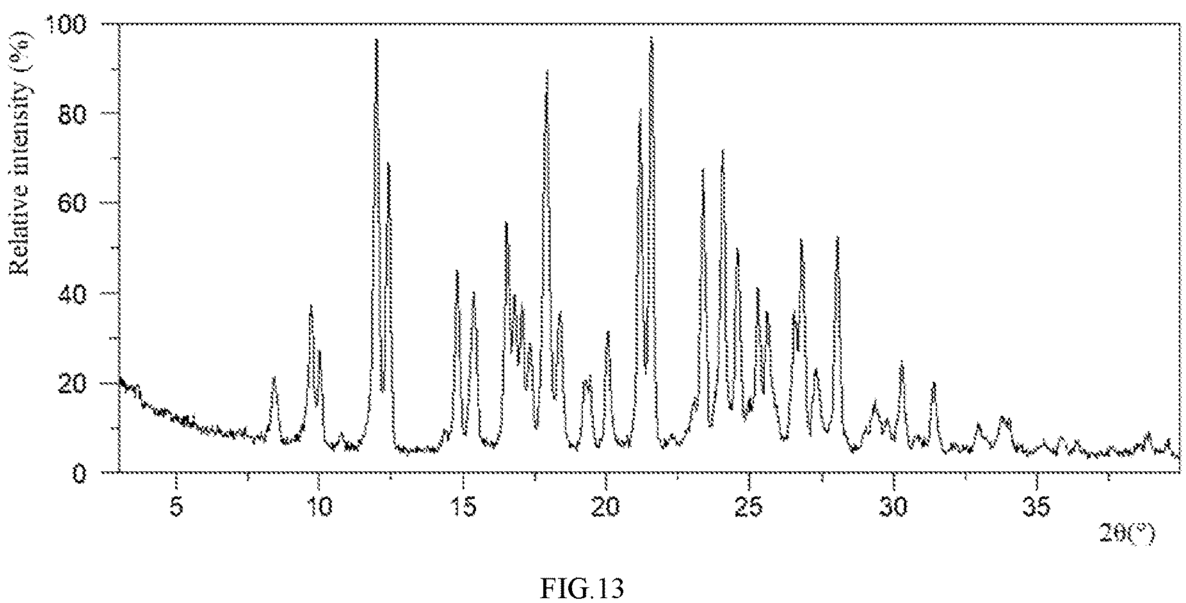
FIG. 13 is a Cu-Kα-radiated XRPD pattern of crystal form G of the compound of formula (II-1).
Figure 14:
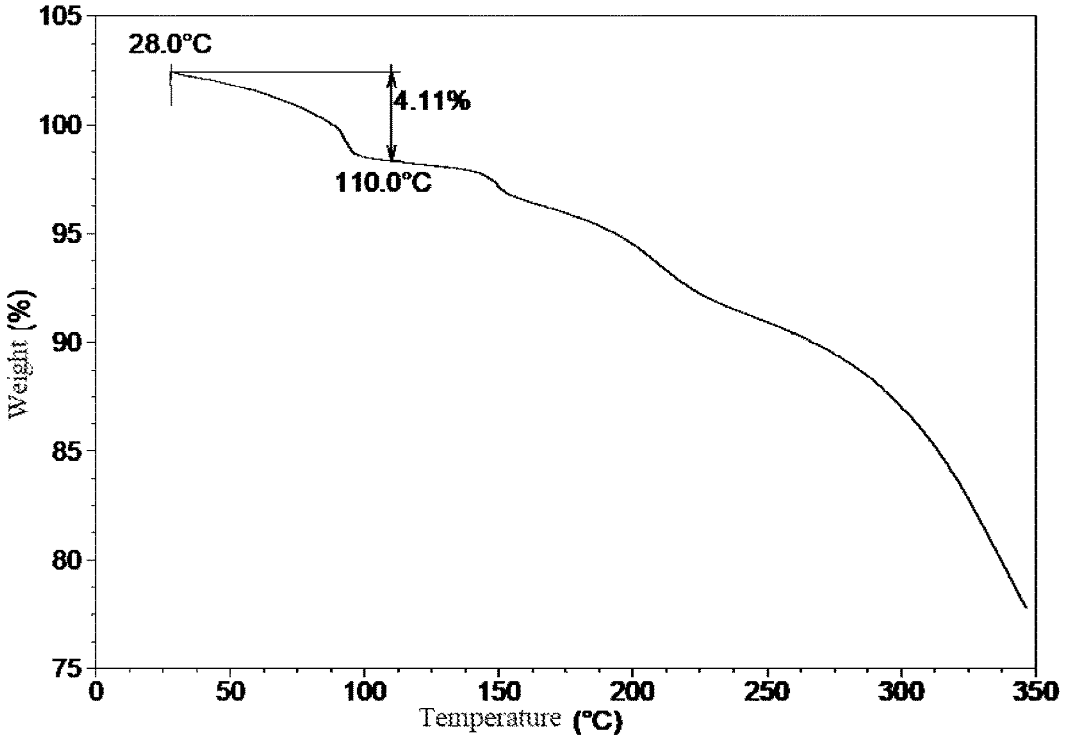
FIG. 14 is a TGA spectrum of crystal form G of the compound of formula (II-1).

The compound of Formula (I) (19.9 mg) was added to 0.5 mL of ethanol/water (volume ratio 9:1) containing 4.8 mg of maleic acid, stirred at room temperature for 2 days to form a suspension, and after centrifugation, evacuation was performed on the solid in vacuum at room temperature for 1 hour to obtain a solid, i.e., crystal form G of the compound of Formula (II-1). The XRPD pattern thereof was as shown in FIG. 13 and the TGA spectrum thereof was as shown in FIG. 14.

Example 9: Preparation of Crystal Form H of the Compound of Formula (II-1)

Figure 15:
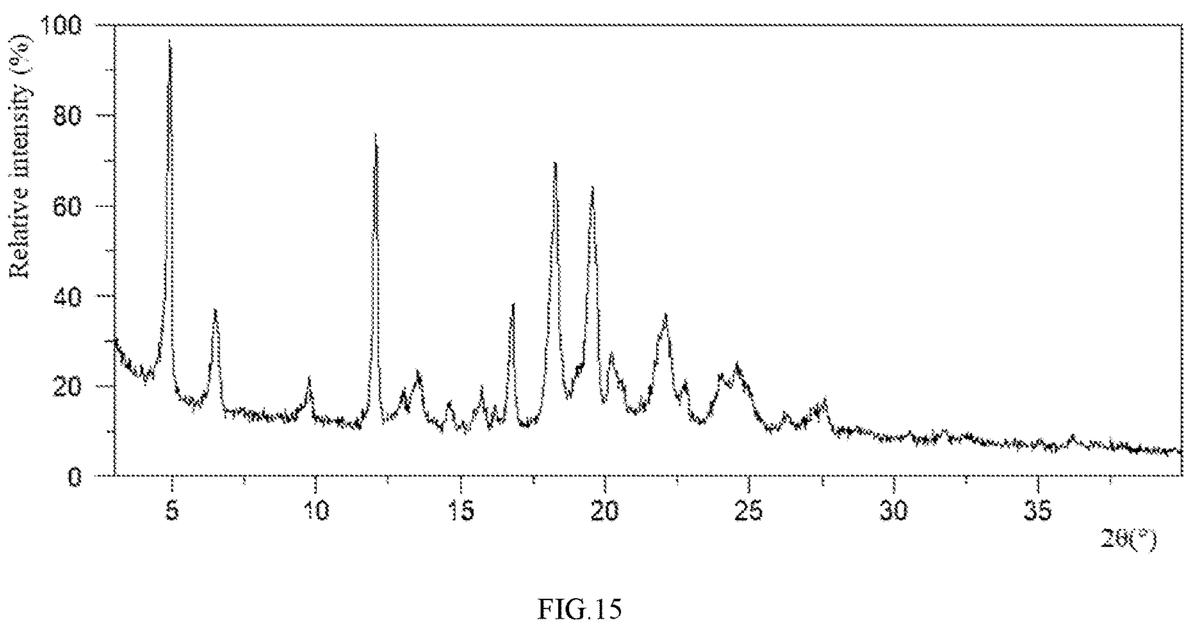
FIG. 15 is a Cu-Kα-radiated XRPD pattern of crystal form H of the compound of formula (II-1).
Figure 16:
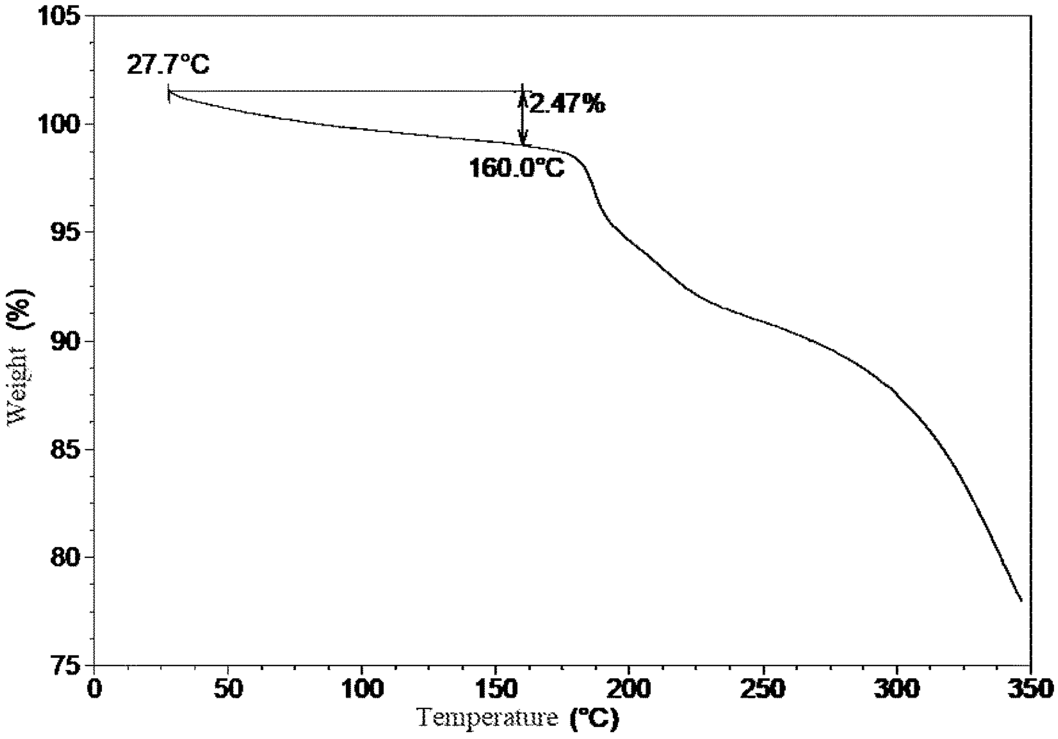
FIG. 16 is a TGA spectrum of crystal form H of the compound of formula (II-1).

The compound of Formula (I) (20.7 mg) was added to 0.5 mL of acetone containing 4.8 mg of maleic acid, stirred at room temperature for 2 days to form a suspension, and after centrifugation, evacuation was performed on the solid in vacuum at room temperature for 1 hour to obtain a solid, i.e., crystal form H of the compound of Formula (II-1). The XRPD pattern thereof was as shown in FIG. 15 and the TGA spectrum thereof was as shown in FIG. 16.

Example 10: Preparation of Crystal Form I of the Compound of Formula (III-1)

(III-1)

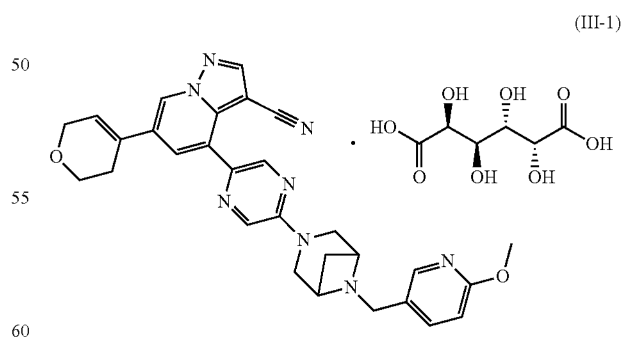

Figure 17:
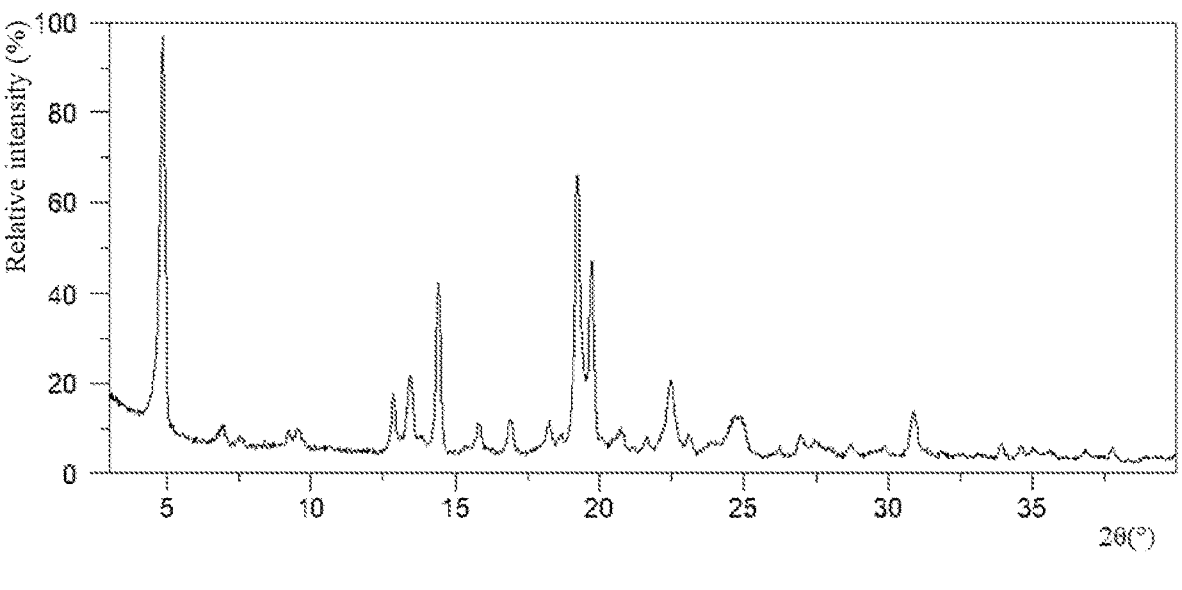
FIG. 17 is a Cu-Kα-radiated XRPD pattern of crystal form I of the compound of formula (III-1).
Figure 18:
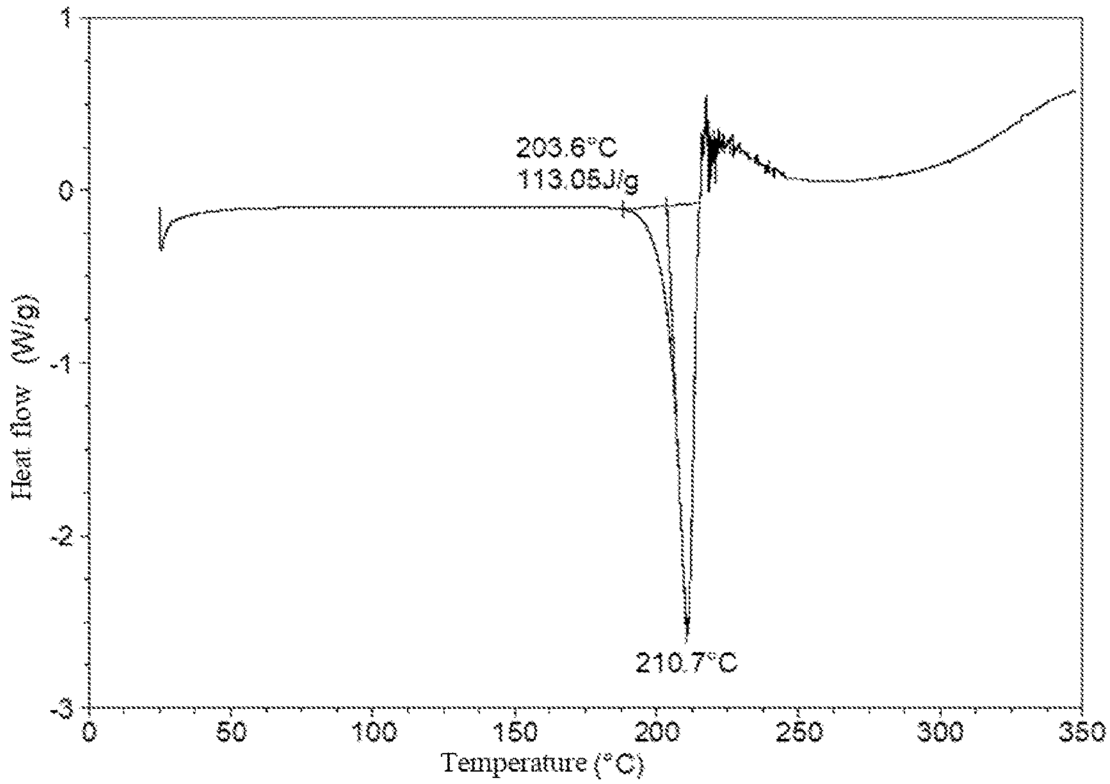
FIG. 18 is a DSC thermogram of crystal form I of the compound of formula (III-1).
Figure 19:
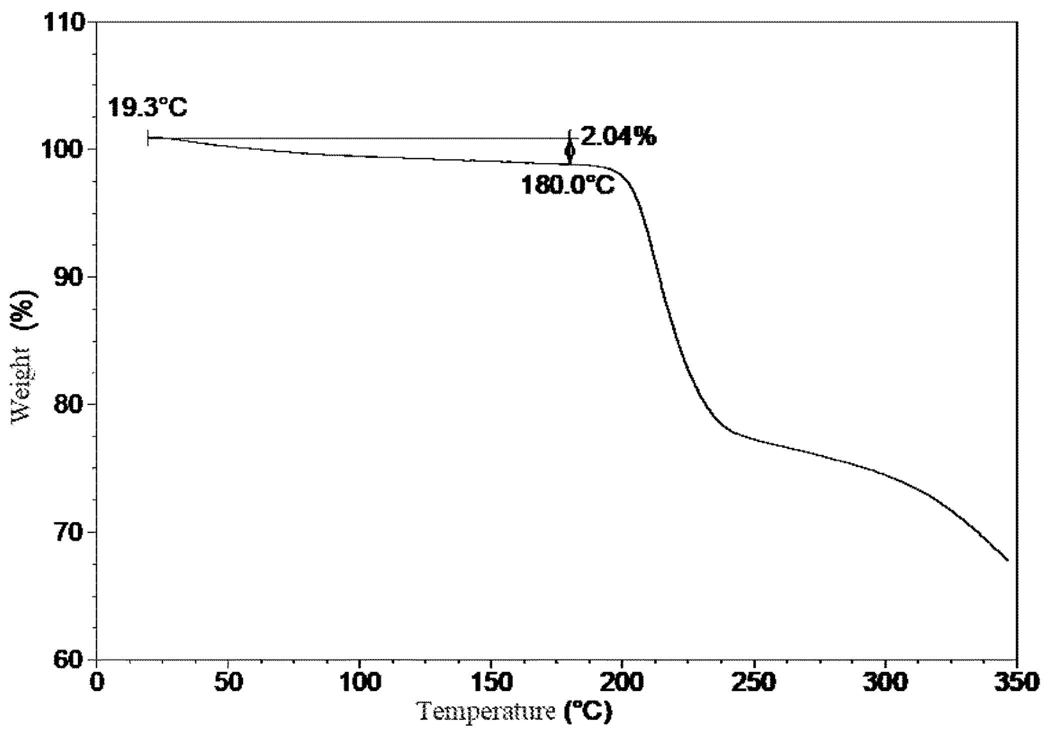
FIG. 19 is a TGA spectrum of crystal form I of the compound of formula (III-1).

The compound of Formula (I) (20.5 mg) was added to 0.5 mL of ethanol/water (volume ratio 9:1) containing 8.6 mg of mucic acid, stirred at room temperature for 2 days to form a suspension, and after centrifugation, evacuation was performed on the solid in vacuum at room temperature for 1 hour to obtain a solid, i.e., crystal form I of the compound of Formula (III-1). The XRPD pattern thereof was as shown in FIG. 17, the DSC thermogram thereof was as shown in FIG. 18, and the TGA spectrum thereof was as shown in FIG. 19.

Example 11: Preparation of Crystal Form J of the Compound of Formula (IV-1)

(IV-1)

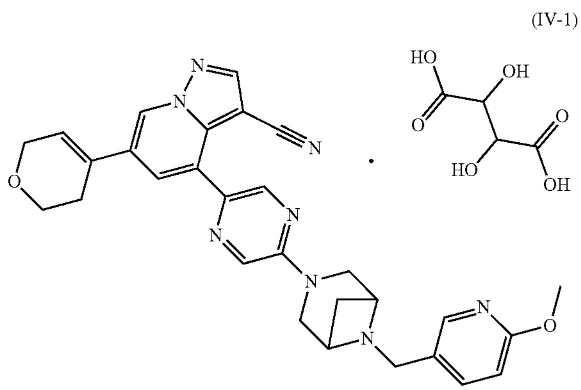 [SMILES: COc1ccc(CN2C3CC2CN(c2cnc(-c4cc(C5=CCOCC5)cn5ncc(C#N)c45)cn2)C3)cn1 ; O=C(O)C(O)C(O)C(=O)O]

Figure 20:
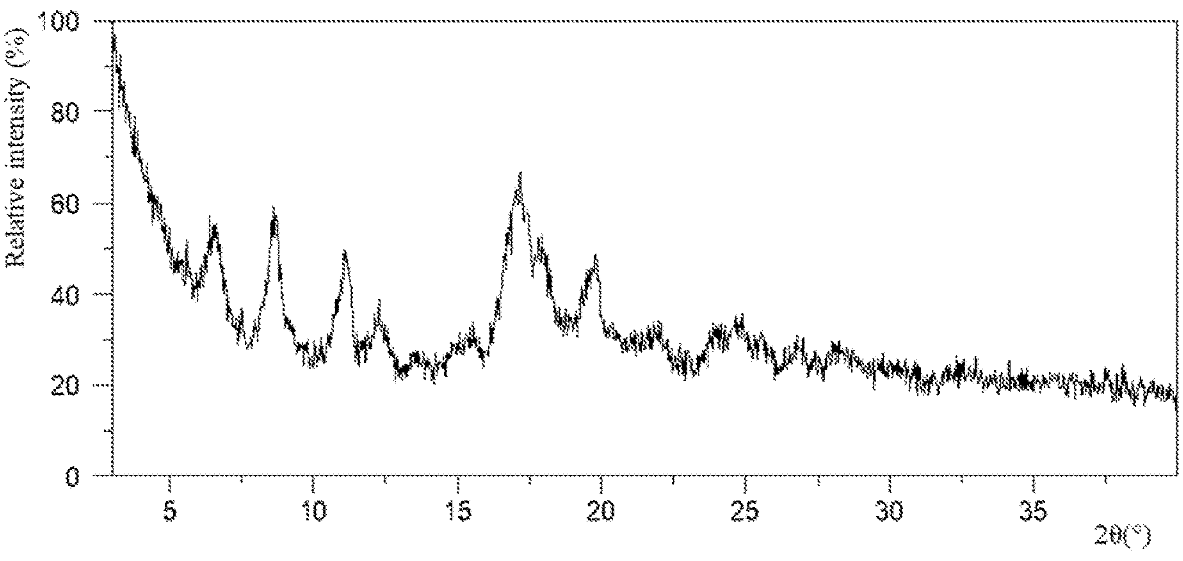
FIG. 20 is a Cu-Kα-radiated XRPD pattern of crystal form J of the compound of formula (IV-1).
Figure 21:
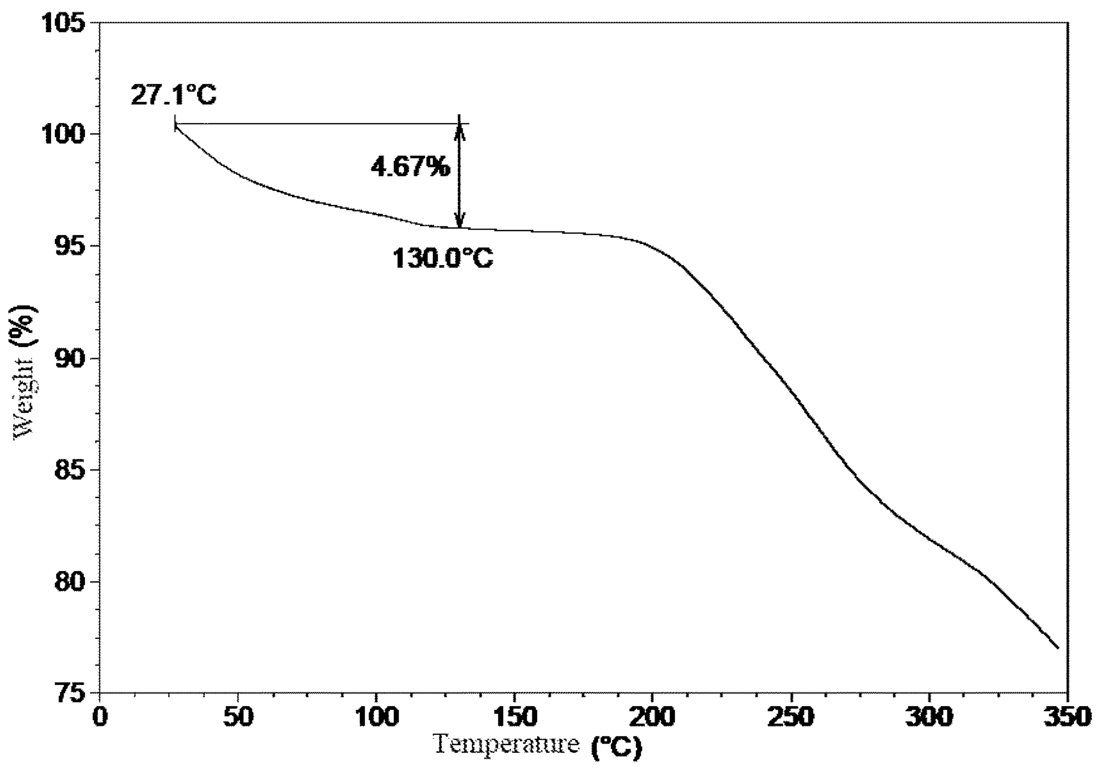
FIG. 21 is a TGA spectrum of crystal form J of the compound of formula (IV-1).

The compound of Formula (I) (19.1 mg) was added to 0.5 mL of ethanol/water (volume ratio 9:1) containing 5.8 mg of tartaric acid, stirred at room temperature for 2 days to form a suspension, and after centrifugation, evacuation was performed on the solid in vacuum at room temperature for 1 hour to obtain a solid, i.e., crystal form J of the compound of Formula (IV-1). The XRPD pattern thereof was as shown in FIG. 20 and the TGA spectrum thereof was as shown in FIG. 21.

Example 12: Preparation of Crystal Form K of the Compound of Formula (V-1)

(V-1)

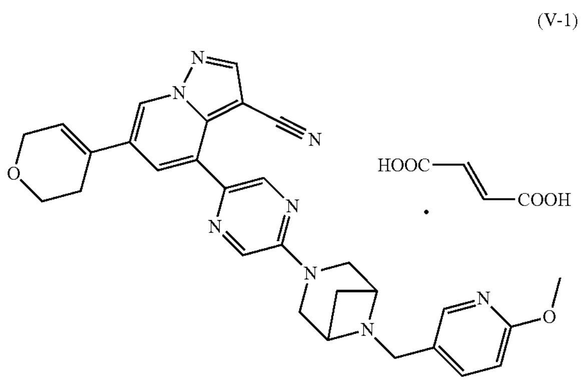 [SMILES: COc1ccc(CN2C3CC2CN(c2cnc(-c4cc(C5=CCOCC5)cn5ncc(C#N)c45)cn2)C3)cn1 ; O=C(O)/C=C/C(=O)O]

Figure 22:
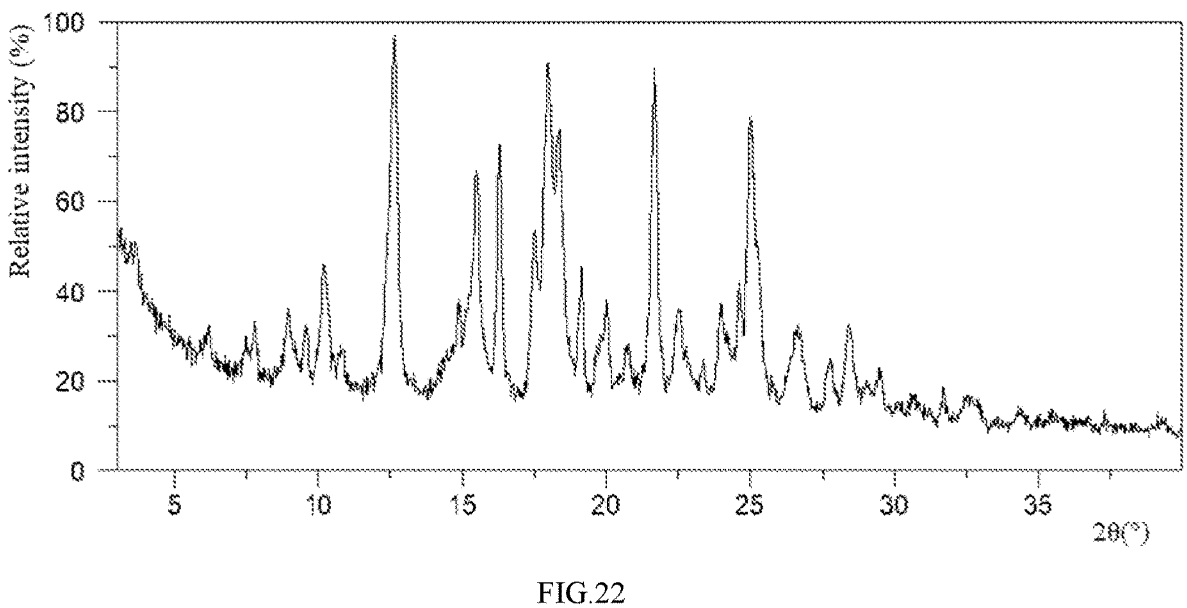
FIG. 22 is a Cu-Kα-radiated XRPD pattern of crystal form K of the compound of formula (V-1).
Figure 23:
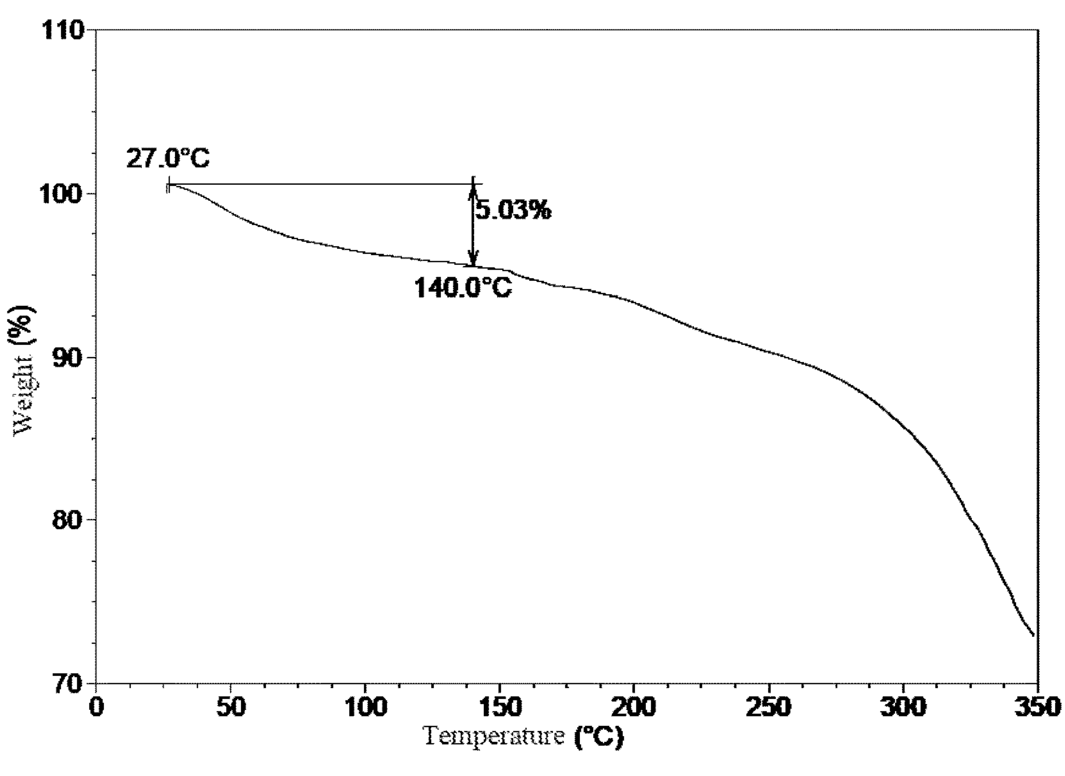
FIG. 23 is a TGA spectrum of crystal form K of the compound of formula (V-1).

The compound of Formula (I) (20.4 mg) was added to 0.5 mL of ethanol/water (volume ratio 9:1) containing 4.4 mg of fumaric acid, stirred at room temperature for 2 days to form a suspension, and after centrifugation, evacuation was performed on the solid in vacuum at room temperature for 1 hour to obtain a solid, i.e., crystal form K of the compound of Formula (V-1). The XRPD pattern thereof was as shown in FIG. 22 and the TGA spectrum thereof was as shown in FIG. 23.

Example 13: Preparation of Crystal Form L of the Compound of Formula (V-1)

Figure 24:
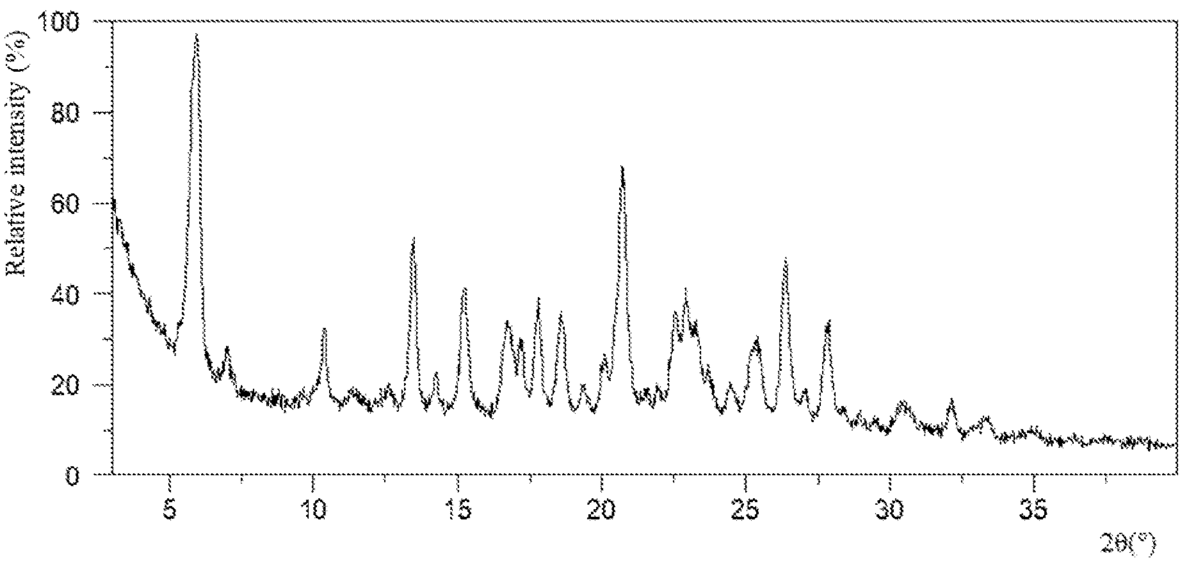
FIG. 24 is a Cu-Kα-radiated XRPD pattern of crystal form L of the compound of formula (V-1).
Figure 25:
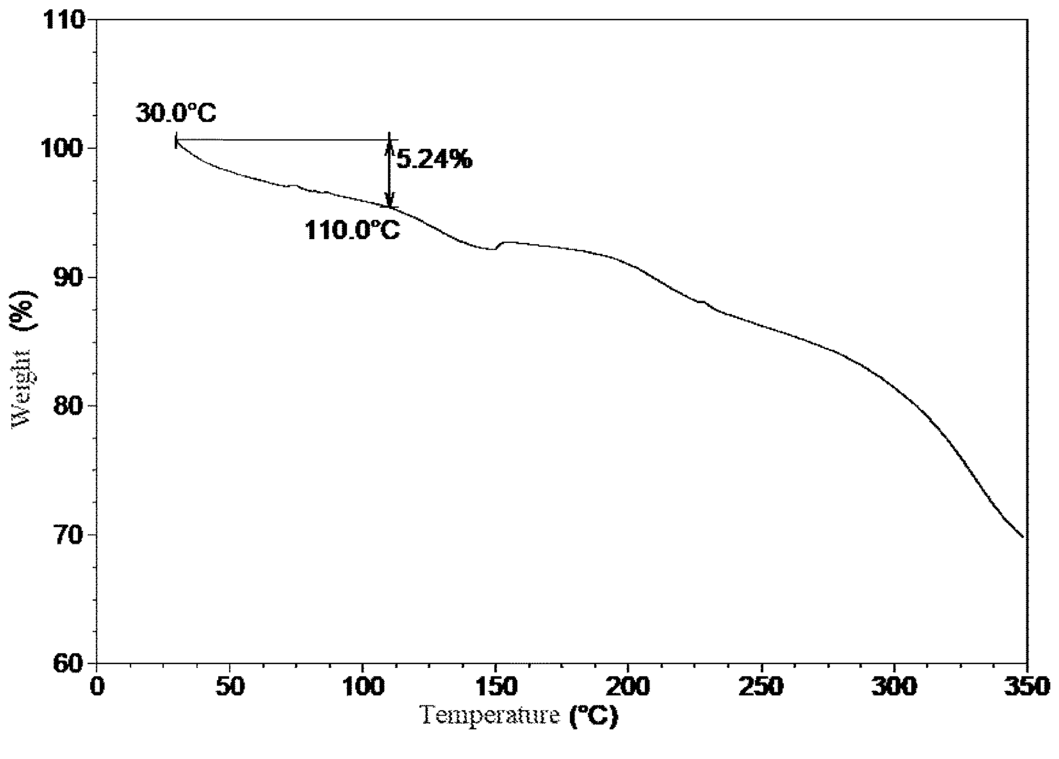
FIG. 25 is a TGA spectrum of crystal form L of the compound of formula (V-1).

The compound of Formula (I) (20.7 mg) was added to 0.5 mL of acetone containing 4.6 mg of fumaric acid, stirred at room temperature for 2 days to form a suspension, and after centrifugation, evacuation was performed on the solid in vacuum at room temperature for 1 hour to obtain a solid, i.e., crystal form L of the compound of Formula (V-1). The XRPD pattern thereof was as shown in FIG. 24 and the TGA spectrum thereof was as shown in FIG. 25.

Example 14: Preparation of Crystal Form M of the Compound of Formula (VI-1)

(VI-1)

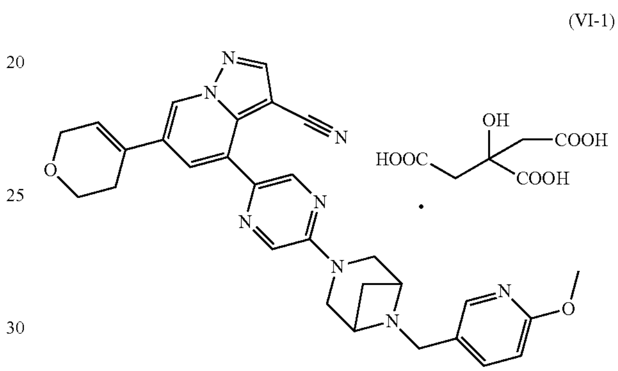

Figure 26:
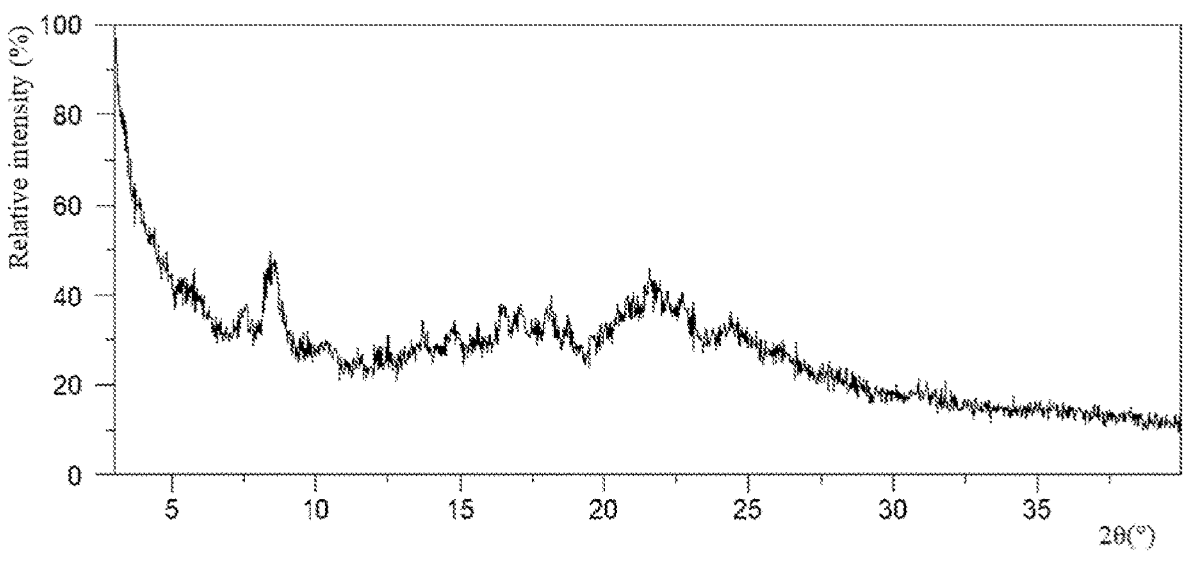
FIG. 26 is a Cu-Kα-radiated XRPD pattern of crystal form M of the compound of formula (VI-1).
Figure 27:
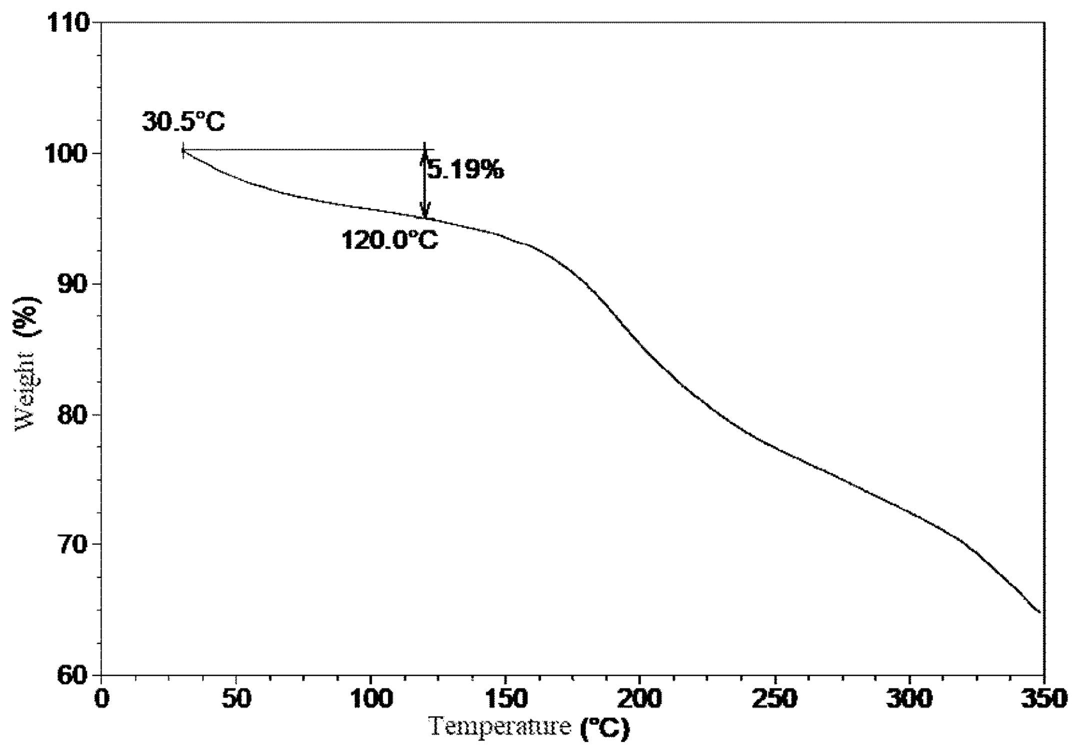
FIG. 27 is a TGA spectrum of crystal form M of the compound of formula (VI-1).

The compound of Formula (I) (19.4 mg) was added to 0.5 mL of acetone containing 7.4 mg of citric acid, stirred at room temperature for 2 days to form a suspension, and after centrifugation, evacuation was performed on the solid in vacuum at room temperature for 1 hour to obtain a solid, i.e., crystal form M of the compound of Formula (VI-1). The XRPD pattern thereof was as shown in FIG. 26 and the TGA spectrum thereof was as shown in FIG. 27.

Example 15: Preparation of Crystal Form N of the Compound of Formula (VII-1)

(VII-1)

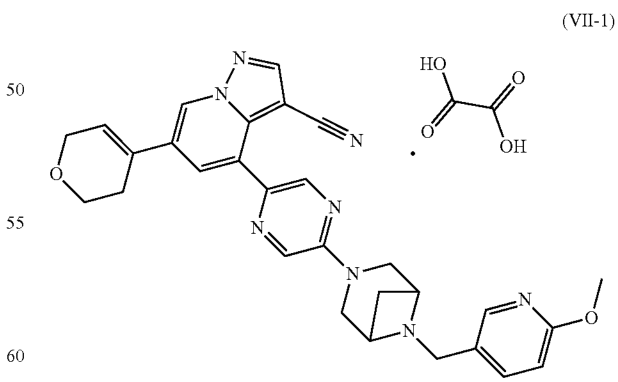

Figure 28:
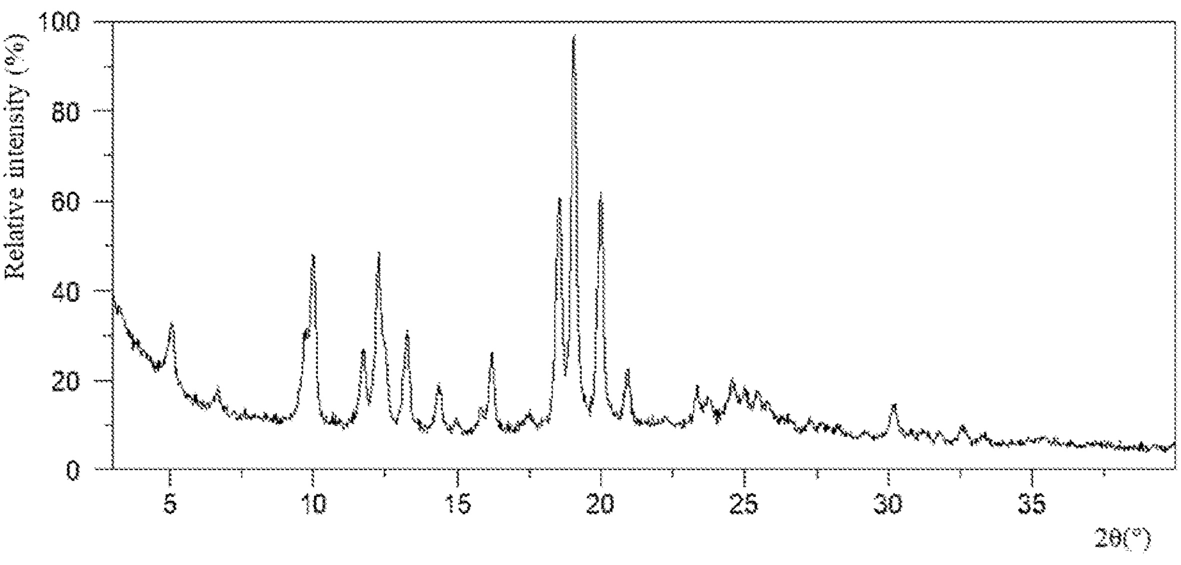
FIG. 28 is a Cu-Kα-radiated XRPD pattern of crystal form N of the compound of formula (VII-1).
Figure 29:
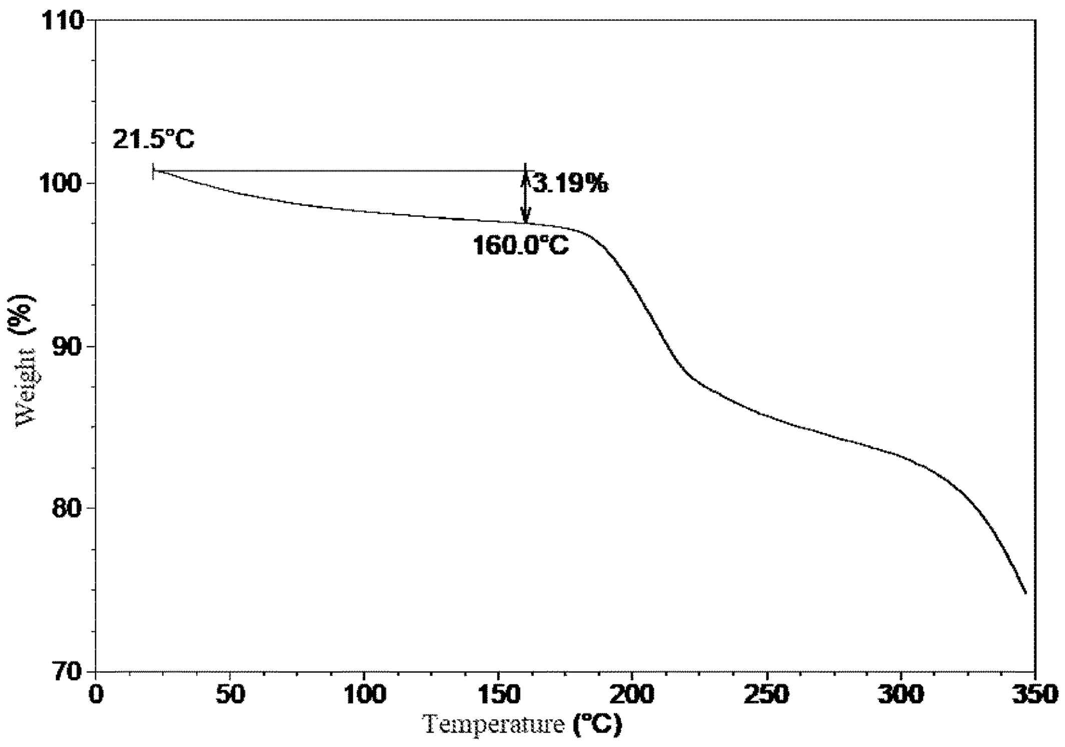
FIG. 29 is a TGA spectrum of crystal form N of the compound of formula (VII-1).

The compound of Formula (I) (19.9 mg) was added to 0.5 mL of ethanol/water (volume ratio 9:1) containing 5.0 mg of oxalic acid, stirred at room temperature for 2 days to form a suspension, and after centrifugation, evacuation was performed on the solid in vacuum at room temperature for 1 hour to obtain a solid, i.e., crystal form N of compound of Formula (VII-1). The XRPD pattern thereof was as shown in FIG. 28 and the TGA spectrum thereof was as shown in FIG. 29.

Example 16: Preparation of Crystal Form O of the Compound of Formula (VII-1)

Figure 30:
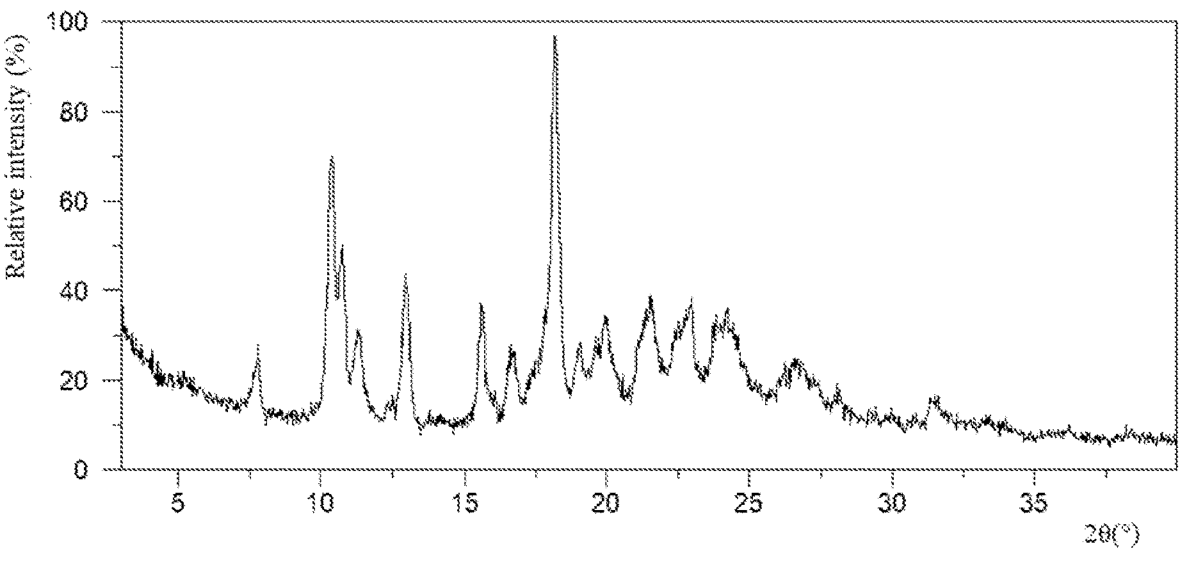
FIG. 30 is a Cu-Kα-radiated XRPD pattern of crystal form 0 of the compound of formula (VII-1).
Figure 31:
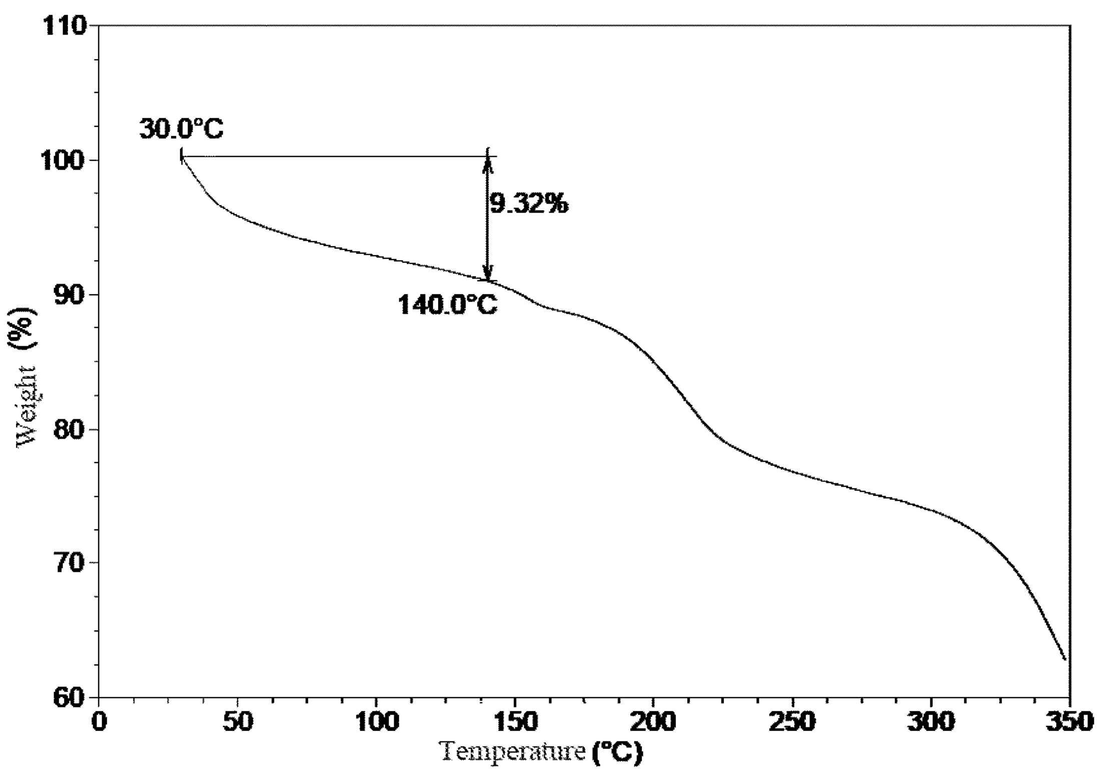
FIG. 31 is a TGA spectrum of crystal form 0 of the compound of formula (VII-1).

The compound of Formula (I) (19.8 mg) was added to 0.5 mL of acetone containing 5.5 mg of oxalic acid, stirred at room temperature for 2 days to form a suspension, and after centrifugation, evacuation was performed on the solid in vacuum at room temperature for 1 hour to obtain a solid, i.e., crystal form O of the compound of Formula (VII-1). The XRPD pattern thereof was as shown in FIG. 30 and the TGA spectrum thereof was as shown in FIG. 31.

Example 17: Preparation of Crystal Form P of the Compound of Formula (VII-1)

Figure 32:
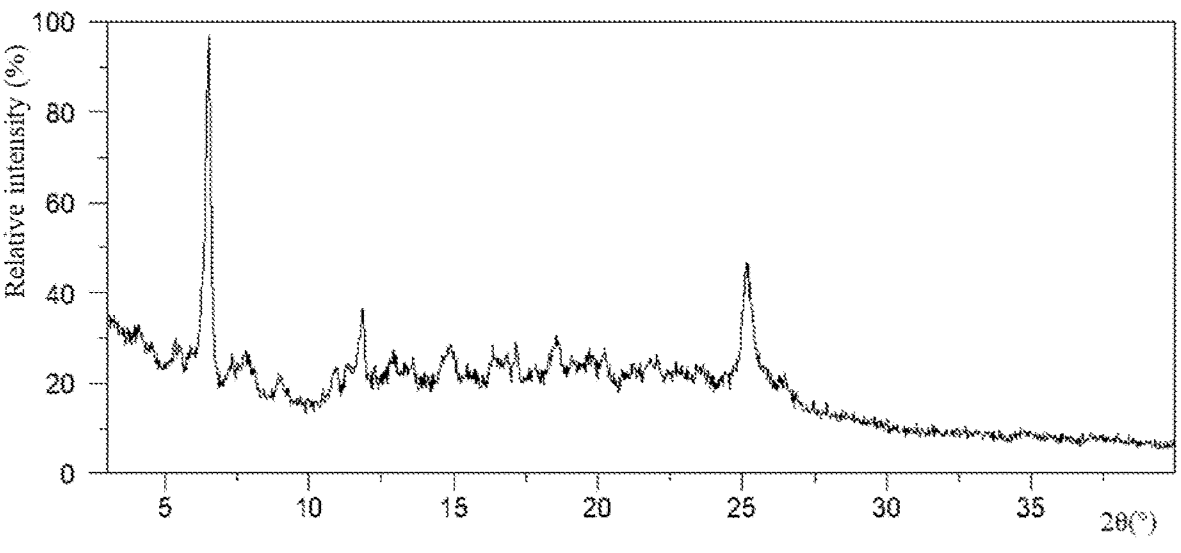
FIG. 32 is a Cu-Kα-radiated XRPD pattern of crystal form P of the compound of formula (VII-1).
Figure 33:
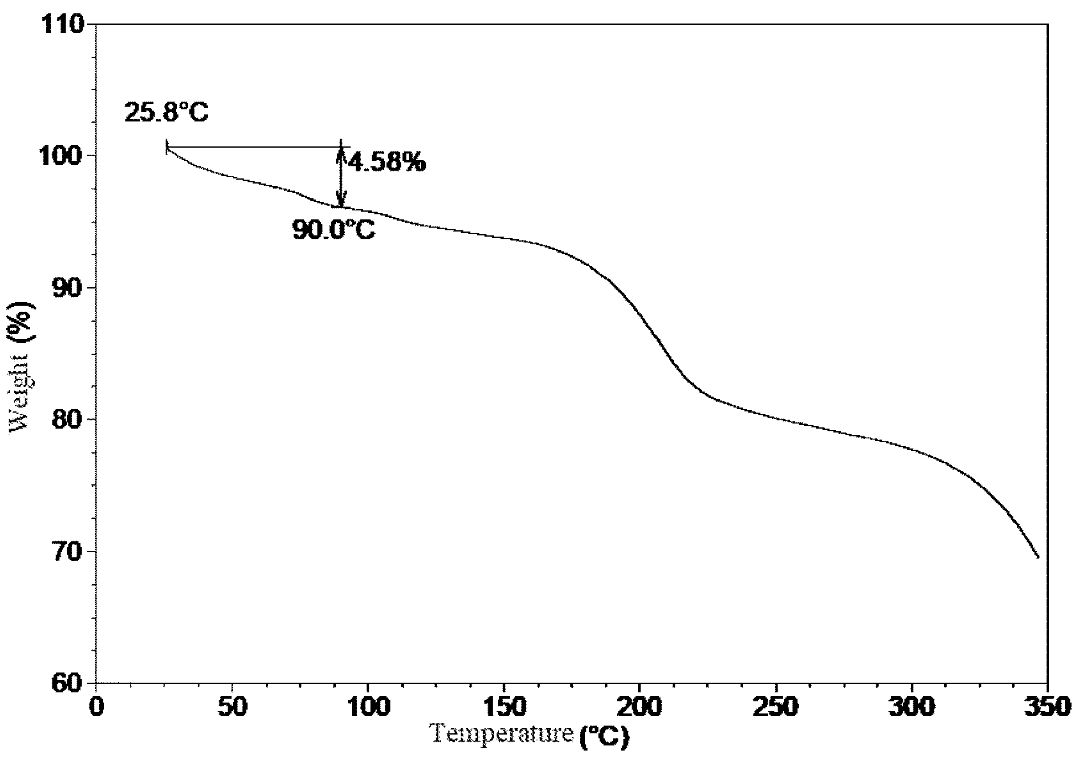
FIG. 33 is a TGA spectrum of crystal form P of the compound of formula (VII-1).

The compound of Formula (I) (19.3 mg) was added to 0.5 mL of ethyl acetate containing 5.1 mg of oxalic acid, stirred at room temperature for 2 days to form a suspension, and after centrifugation, evacuation was performed on the solid in vacuum at room temperature for 1 hour to obtain a solid, i.e., crystal form P of the compound of Formula (VII-1). The XRPD pattern thereof was as shown in FIG. 32 and the TGA spectrum thereof was as shown in FIG. 33.

Example 18: Preparation of Crystal Form Q of the Compound of Formula (VIII-1)

(VIII-1)

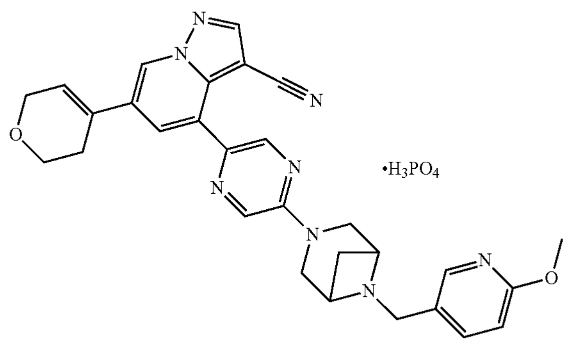

Figure 34:
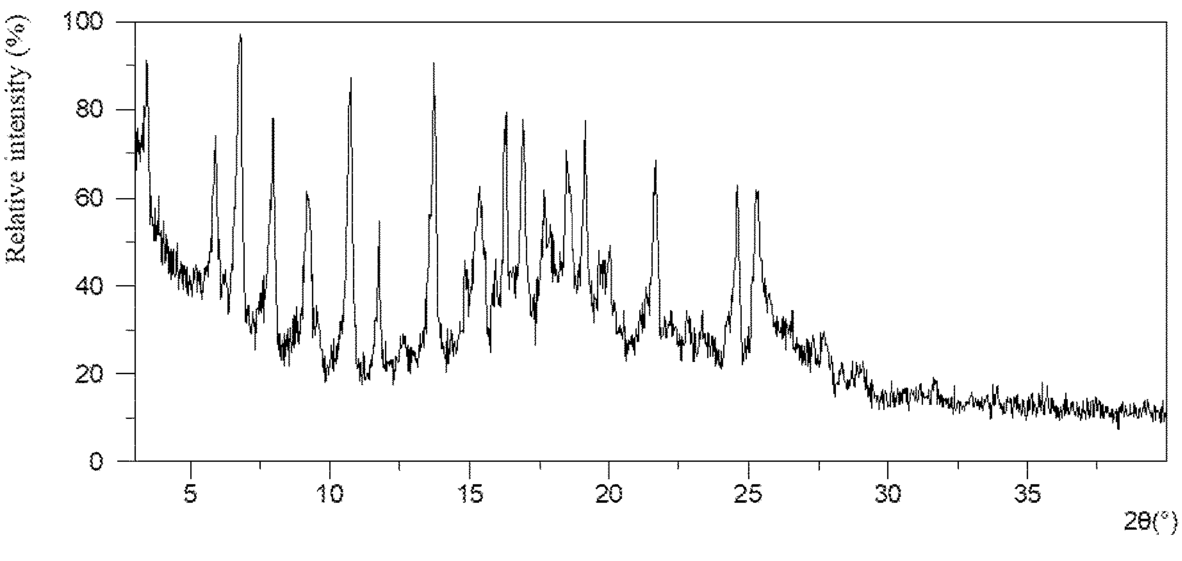
FIG. 34 is a Cu-Kα-radiated XRPD pattern of crystal form Q of the compound of formula (VIII-1).
Figure 35:
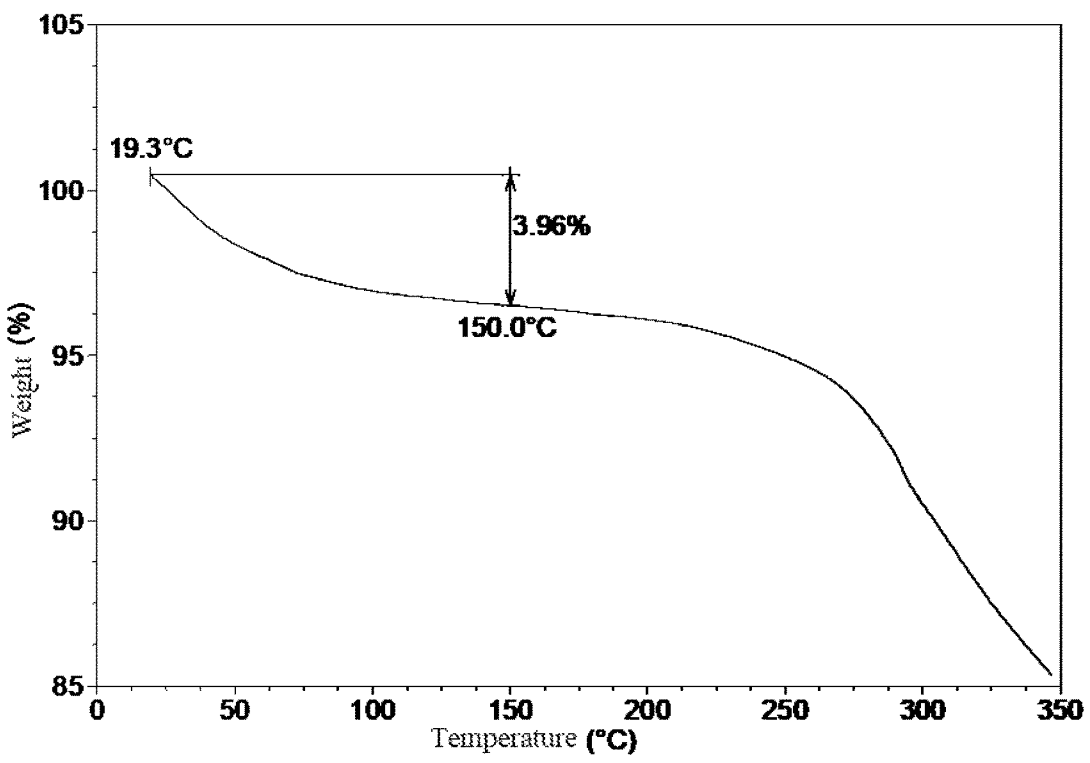
FIG. 35 is a TGA spectrum of crystal form Q of the compound of formula (VIII-1).

The compound of Formula (I) (19.3 mg) was added to 0.5 mL of ethanol/water (volume ratio 9:1) containing 3.9 mg of phosphoric acid, stirred at room temperature for 2 days to form a suspension, and after centrifugation, evacuation was performed on the solid in vacuum at room temperature for 1 hour to obtain a solid, i.e., crystal form Q of compound of Formula (VIII-1). The XRPD pattern thereof was as shown in FIG. 34 and the TGA spectrum thereof was as shown in FIG. 35.

Example 19: Preparation of Crystal Form R of the Compound of Formula (VIII-1)

Figure 36:
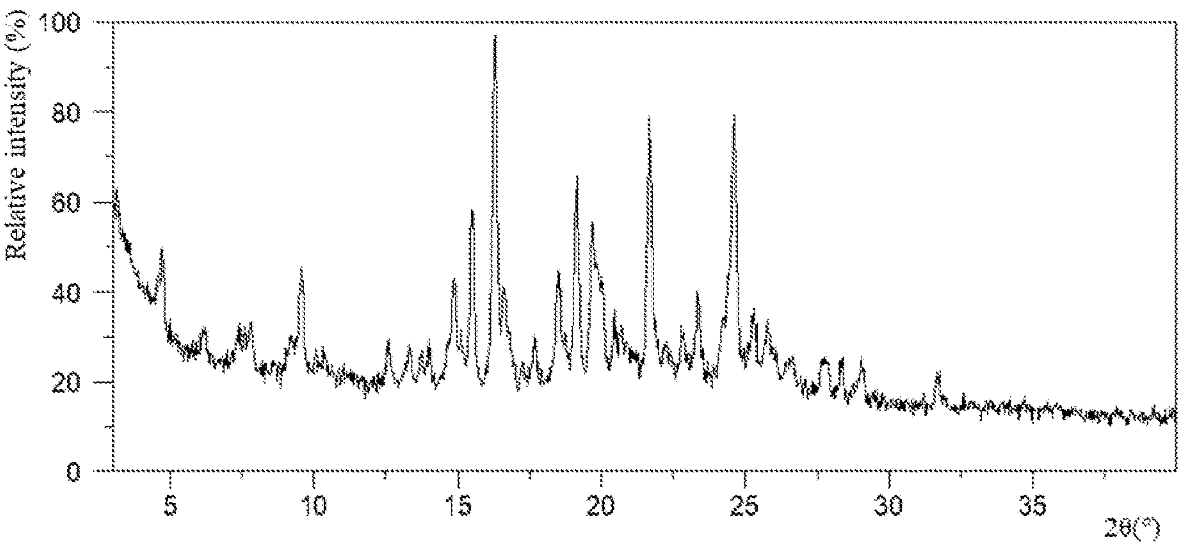
FIG. 36 is a Cu-Kα-radiated XRPD pattern of crystal form R of the compound of formula (VIII-1).
Figure 37:
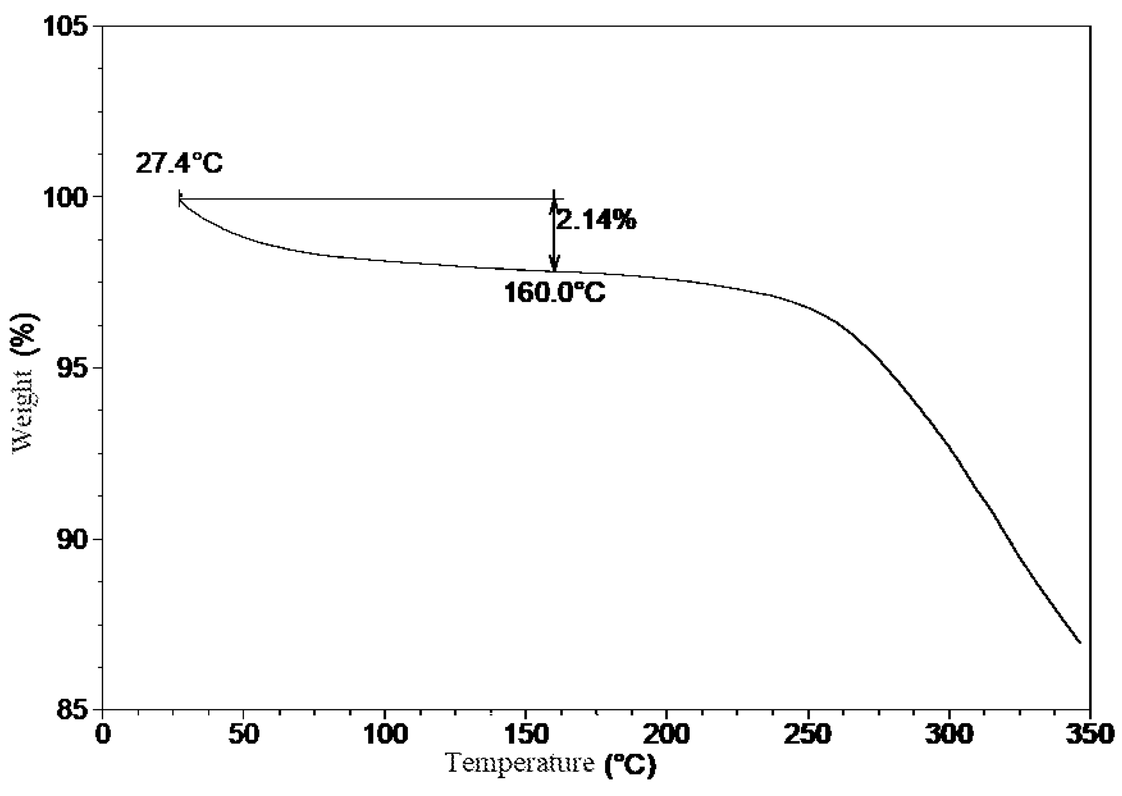
FIG. 37 is a TGA spectrum of crystal form R of the compound of formula (VIII-1).

The compound of Formula (I) (19.7 mg) was added to 0.5 mL of acetone containing 4.4 mg of phosphoric acid, stirred at room temperature for 2 days to form a suspension, and after centrifugation, evacuation was performed on the solid in vacuum at room temperature for 1 hour to obtain a solid, i.e., crystal form R of the compound of Formula (VIII-1). The XRPD pattern thereof was as shown in FIG. 36 and the TGA spectrum thereof was as shown in FIG. 37.

Example 20: Hygroscopicity Study on Crystal Form a of the Compound of Formula (I)

Experimental Material:

SMS DVS Intrinsic Dynamic Vapor Sorption Instrument

Experimental Method:

10-15 mg of crystal form A of the compound of Formula (I) was taken and placed in a DVS sample tray for testing.

Figure 38:
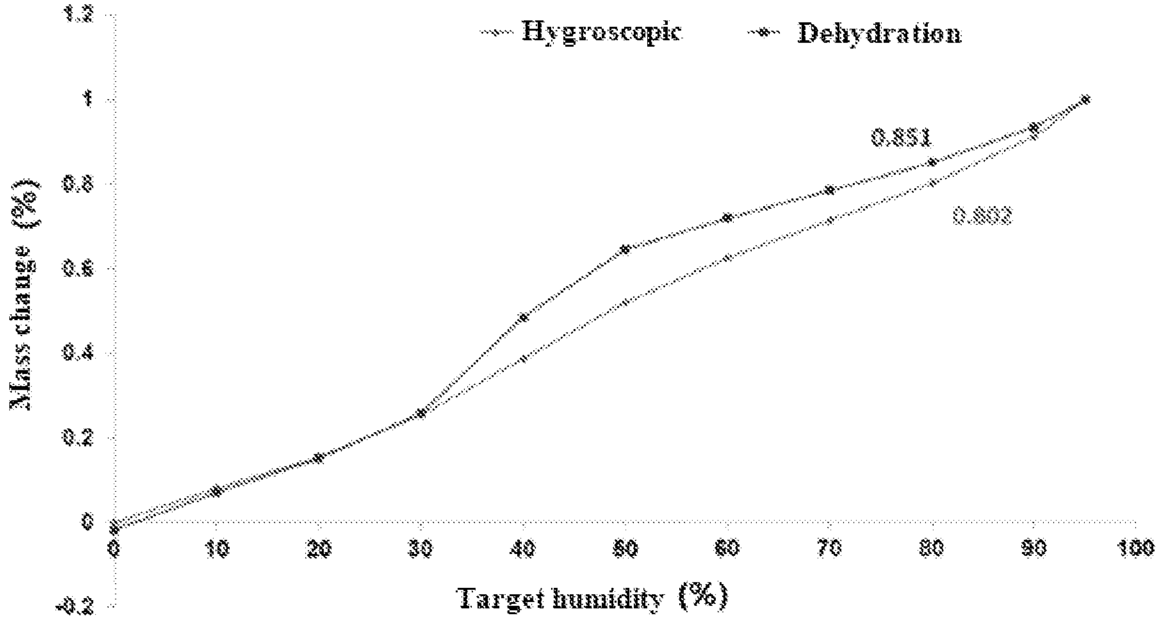
FIG. 38 is a DVS plot of crystal form A of the compound of formula (I).

Experimental Results:

A DVS plot of crystal form A of the compound of Formula (I) was as shown in FIG. 38, $\Delta W$=0.8%.

Experimental Conclusion:

The hygroscopic weight gain of crystal form A of the compound of Formula (I) was 0.8% at 25° C. and 80% RH, i.e., being slightly hygroscopic.

Example 21: Solid Stability Experiment of Crystal Form a of the Compound of Formula (I)

According to the Guidelines for the Stability Testing of Raw Materials and Preparations (General Chapter No. 9001 part of Volume IV of Chinese Pharmacopoeia 2015 Edition), the stability of crystal form A of the compound of Formula (I) was investigated under conditions of high temperature (60° C., open) and high humidity (room temperature/relative humidity 92.5%, open).

15 mg of crystal form A of the compound of Formula (I) was weighed out, placed at the bottom of a glass sample flask, spread out into a thin layer. For samples placed under high temperature and high humidity, use aluminum foil to seal the bottle, and prick some holes on the aluminum foil to ensure that the sample can fully contact with the ambient air. The samples placed under different conditions were sampled for XRPD detection on Days 5 and 10, and the test results were compared with the initial test results on Day 0. The test results were shown in Table 19 below:

TABLE 19

Solid stability experiment results of crystal form A of the compound of Formula (I)

| Test conditions | Time point | Crystal form |
|---|---|---|
| — | Day 0 | Crystal form A |
| High temperature (60° C., open) | Day 5 | Crystal form A |
| | Day 10 | Crystal form A |
| High humidity (room temperature/ relative humidity 92.5%, open) | Day 5 | Crystal form A |
| | Day 10 | Crystal form A |

Conclusion: The crystal form A of the compound of Formula (I) had good stability under conditions of high temperature and high humidity.

Example 22: Solid Stability Study on Crystal Form a of the Compound of Formula (I)

According to the Guidelines for the Stability Testing of Raw Materials and Preparations (General Chapter No. 9001 of Volume IV of Chinese Pharmacopoeia 2015 Edition), the stability of crystal form A of the compound of Formula (I) was investigated under long-term experimental conditions. Approximately 10 mg of crystal form A of the compound of Formula (I) was weighed out, placed at the bottom of a glass sample flask, spread into a thin layer and sealed with an aluminum foil, the aluminum foil was pierced with small holes. The flasks were placed under 40° C./75% RH conditions for 3 months or under 25° C./60% RH conditions for 3 months, then sampled for XRPD detection, and the detection results were compared with the initial test results of Day 0. The results were as shown in Table 20. The crystal form A of the compound of Formula (I) had no crystal form change under all stability conditions.

The experimental results were shown in Table 20 below:

TABLE 20

Solid stability experiment results of crystal form A of the compound of Formula (I)

| Test conditions | Condition of taking points | Crystal form |
|---|---|---|
| Initial crystal form A | / | Crystal form A |
| 40° C./75% RH | 3 months | Crystal form A |
| 25° C./60% RH | 3 months | Crystal form A |

Experimental conclusion: The crystal form A of the compound of Formula (I) had good stability.

Biological Test Data:

Experiment 1: In Vitro Enzyme Activity Test of the Compound of the Present Invention

Experimental Purpose

The enzyme activity was experimentally detected by Z'-LYTE™ kinase test, and the inhibitory effect of the compound on RET and RET (V804M) kinase was evaluated with the $IC_{50}$ value of the compound as an indicator.

Experimental Method

The concentration of the compound used for the RET and RET (V804M) kinase test was diluted by a factor of 3, giving 10 concentrations from 3 μM to 0.152 nM. The content of DMSO in the detection reaction was 1%.

Reagents:

Basic reaction buffer, 20 mM hydroxyethyl piperazine-ethanesulfonic acid (Hepes) (pH 7.5) buffer, 10 mM $MgCl_2$, 1 mM ethylene glycol bis(aminoethyl ether)tetraacetic acid (EGTA), 0.02% polyoxyethylene dodecyl ether (Brij35), 0.02 mg/mL bovine serum protein, 0.1 mM $Na_3VO_4$, 2 mM dithiothreitol (DTT) and 1% DMSO.

Compound:

The compound to be tested was dissolved in 100% DMSO system and diluted to 10 mM for use. Integra Viaflo Assist was used for solution dilution.

Reaction Process of Generic Enzyme:

Test conditions: The concentration of RET enzyme was 3 μM, the concentration of the peptide substrate CHKtide was 1000 μM, and the concentration of ATP was 20 μM; and the concentration of RET (V804M) enzyme was 80 μM, the concentration of substrate peptide was 1000 μM, and the concentration of ATP was 30 μM.

Reaction process: A kinase/polypeptide solution was prepared according to the test conditions. Compound solutions of different concentrations were added, incubation was carried out at room temperature for 20 minutes, 33P-ATP at the corresponding concentration was added, and incubation was carried out at room temperature for 120 minutes. Radioactivity was detected by filter-binding method.

Reaction Detection:

Phosphoric acid with a concentration of 0.5% was added to the kinase reaction solution to stop the reaction, and Envision instrument was used for plate reading.

Data Analysis

The data were converted into phosphorylation rate and inhibition rate, and the $IC_{50}$ data of the compound was obtained by parameter curve fitting (GraphPad Software).

The Experimental Results were Shown in Table 21:

TABLE 21

$IC_{50}$ test results of kinase activity of the compound of the present invention

| Test article | RET enzyme $IC_{50}$ (nM) | RET V804M $IC_{50}$ (nM) |
|---|---|---|
| Trifluoroacetate of the compound of Formula (I) | 0.72 | 5.86 |

Experimental conclusion: The compound of the present invention had excellent inhibitory activity on RET and its mutant RET V804M and would have excellent therapeutic effects on patients with abnormal RET tumors.

Experiment 2: Pharmacokinetic Evaluation of the Compound of the Present Invention Experimental procedure: A 0.1 mg/mL clear solution of the test compound in the corresponding solvent medium (see Table 22) was injected into female Balb/c mice (fasting overnight, 7-9 weeks old) via tail vein at a dose of 0.2 mg/kg. About 30 μL of blood was collected from jugular vein or tail vein at 0.0833, 0.25, 0.5, 1.0, 2.0, 4.0, 8.0 and 24 h after intravenous administration. 0.2 mg/mL of the test compound suspended in the corresponding solvent medium (see Table 22) was given to female Balb/c mice (fasting overnight, 7-9 weeks old) by gavage at a dose of 2 mg/kg. The experimental conditions were detailed in Table 22. At 0.0833, 0.25, 0.5, 1.0, 2.0, 4.0, 6.0, 8.0 and 24 h after oral administration, about 30 μL of blood was collected from the jugular vein or tail vein of the female Balb/c mice. The blood was placed in an anticoagulant tube in which EDTA-K2 had been added, and plasma was separated by centrifugation. The plasma concentration was determined by LC-MS/MS method, and the relative pharmacokinetic parameters were calculated using WinNonlin™ Version 6.3 (Pharsight, Mountain View, CA) pharmacokinetic software by non-compartment model linear logarithmic trapezoidal method. The experimental results were as shown in Table 23.

TABLE 22

| Experimental conditions for pharmacokinetics in mice | | | | |
|---|---|---|---|---|
| | IV (injection) | | PO (oral) | |
| | Dose | Solvent medium | Dose | Solvent medium |
| Trifluoroacetate of the compound of Formula (I) | 0.2 mg/kg | 0.1 mg/mL 5% DMSO + 10% polyethylene glycol-15 hydroxystearate (Solutol) + 85% $H_2O$ clear solution | 2 mg/kg | 0.2 mg/mL 5% DMSO + 10% polyethylene glycol-15 hydroxystearate (Solutol) + 85% $H_2O$ clear solution |

TABLE 23

| Experimental results of pharmacokinetics in mice | | | | | | | | |
|---|---|---|---|---|---|---|---|---|
| | IV 0.2 mg/kg | | | | PO | | | |
| | Cl | | | | 2 mg/kg | | | |
| Dose | (mL/min/kg) | $V_{dss}$ (L/kg) | $T_{1/2}$ (h) | $AUC_{0-last}$ (nM · h) | $C_{max}$ (nM) | $T_{max}$ (h) | $AUC_{0-last}$ (nM · h) | F (%) |
| Trifluoro-acetate of the compound of Formula (I) | 2.3 | 0.5 | 2.6 | 2794 | 5340 | 2 | 26926 | 96.4 |

Note:
Plasma clearance (Cl), apparent steady-state distribution volume ($V_{dss}$), elimination half-life ($T_{1/2}$), area under plasma concentration curve from 0 to the last quantifiable time point ($AUC_{0-last}$), bioavailability (F), peak concentration ($C_{max}$) and peak time $T_{max}$.

Conclusion: From the experimental results, the compounds of the present invention all exhibited a low clearance, a low distribution volume, a relatively long half-life and excellent drug exposure after intravenous administration. For oral administration, the compounds of the present invention all exhibited relatively a short $T_{max}$, excellent oral absorption exposure and overall showed excellent oral absorption bioavailability.

Experiment 3: Analysis of Tumor Growth Inhibition (TGI)

Ba/F3-CCDC6-RET cell strain was cultured using 1640 medium (Biological Industries)+10% fetal bovine serum (BI)+1% double antibody (Penicillin Streptomycin solution, Coring, USA) at 37° C. with 5% $CO_2$ and subcultured twice a week. When the cell saturation is 80-90%, cells were collected, counted, and inoculated subcutaneously into the right axillary of BALB/c nude female mice (6-8 weeks). After the inoculation was completed, the tumor growth status was observed day by day. When the average tumor volume reached about 165.77 $mm^3$, the mice were randomly divided into groups, with 6 mice per group, and administration was started.

The health status and death of the animals were detected daily. Routine examinations included tumor growth, activity, diet, weight, eyes, hair and other abnormal behaviors of the animals, and the tumor volume and weight were measured twice a week (Tuesday and Friday).

The inhibitory effect of the compound on tumor growth was evaluated by the relationship between tumor volume and time. The tumor volume was measured by vernier caliper, with the formula being TV=0.5 a×$b^2$, wherein, "a" was the long diameter of the tumor and "b" was the short diameter of the tumor. TGI was calculated by the difference between the median tumor volume of the mice in the solvent group and the median tumor volume of the mice in the drug group, expressed as the percentage of the median tumor volume in the solvent control group, it was calculated by the following formula:

$$TGI(TGI(\%) = [1 - (T_{23} - T_0)/(V_{23} - V_0)] \times 100)$$

Unless otherwise specified, the data were expressed as mean±standard error (Mean±SE), and one way ANOVA test method was used to determine whether there was significant difference between the tumor volume in the treatment group and the tumor volume in the control group. $P<0.05$ referred to significant difference. 5% DMSO+10% polyethylene glycol-15 hydroxystearate (Solutol)+85% $H_2O$ was used as negative control. The experimental results were as shown in Table 24.

TABLE 24

| Experimental results of antitumor activity in mice | | | |
|---|---|---|---|
| Test article | Ba/F3-CCDC6-RET cell xenograft tumor model | TGI % (tumor volume on Day 23 after administration) | P value |
| Trifluoroacetate of the compound of Formula (I) | 10 mg/kg$^{(D0-D13)}$/ 5 mg/kg$^{(D14-D17)}$/ 2.5 mg/kg$^{(D18-D28)}$ (BID) | 98 | <0.001 |

Note:
BID: twice a day; QD: once a day; and TGI %: tumor growth inhibition rate.

Conclusion: The compound of the present invention exhibited excellent tumor growth inhibition effect in the tumor model Ba/F3-CCDC6-RET.

The invention claimed is:

1. A crystal form A of the compound of Formula (I), (I)

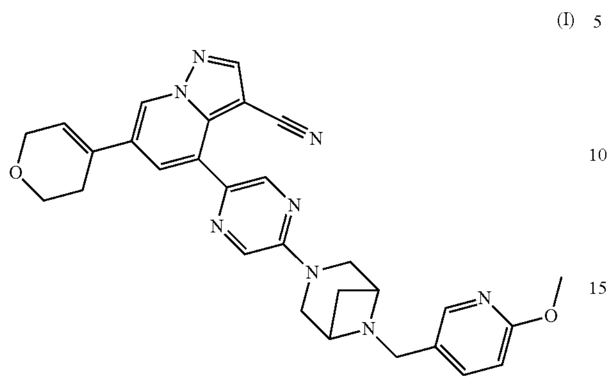

wherein the X-ray powder diffraction pattern of the crystal form A has characteristic diffraction peaks at the 2θ angles comprising: 15.51±0.20°, 16.30±0.20°, 19.16±0.20°, 21.69±0.20° and 24.63±0.20°.

2. The crystal form A according to claim 1, wherein the X-ray powder diffraction pattern of the crystal form A has characteristic diffraction peaks at the 20 angles of: 14.88 t 0.20°, 15.51±0.20°, 16.30±0.20°, 18.49±0.20°, 19.16±0.20°, 19.70±0.20°, 21.69±0.20° and 24.63±0.20°.

3. The crystal form A according to claim 2, wherein the X-ray powder diffraction pattern of the crystal form A has characteristic diffraction peaks at the 20 angles of: 7.79±0.20°, 9.58±0.20°, 12.61±0.20°, 14.88±0.20°, 15.51±0.20°, 16.30±0.20°, 18.49±0.20°, 19.16±0.20°, 19.70±0.20°, 21.69 t 0.20° and 24.63±0.20°.

4. The crystal form A according to claim 1, wherein the XRPD pattern of the crystal form A has characteristic diffraction peaks at the 2θ angles of:

| No. | 2θ angle (°) |
|---|---|
| 1 | 3.29 |
| 2 | 6.19 |
| 3 | 7.79 |
| 4 | 9.21 |
| 5 | 9.58 |
| 6 | 10.32 |
| 7 | 12.61 |
| 8 | 14.88 |
| 9 | 15.10 |
| 10 | 15.51 |
| 11 | 16.30 |
| 12 | 16.60 |
| 13 | 17.65 |
| 14 | 18.49 |
| 15 | 19.16 |
| 16 | 19.70 |
| 17 | 20.03 |
| 18 | 20.45 |
| 19 | 21.69 |
| 20 | 22.24 |
| 21 | 22.83 |
| 22 | 23.38 |
| 23 | 24.63 |
| 24 | 25.29 |
| 25 | 25.76 |
| 26 | 26.58 |
| 27 | 27.70 |
| 28 | 28.34 |
| 29 | 29.06 |
| 30 | 31.71 |
| 31 | 32.97 |
| 32 | 33.49. |

5. The crystal form A according to claim 1, wherein the differential scanning calorimetry curve of the crystal form A has a starting point of an endothermic peak at 188.7±2° C.

6. The crystal form A according to claim 1, wherein the thermogravimetric analysis curve of the crystal form A shows a weight loss of 1.20% at 180.0±3° C.

7. The crystal form A according to claim 2, wherein the differential scanning calorimetry curve of the crystal form A has a starting point of an endothermic peak at 188.7±2° C.

8. The crystal form A according to claim 3, wherein the differential scanning calorimetry curve of the crystal form A has a starting point of an endothermic peak at 188.7±2° C.

9. The crystal form A according to claim 2, wherein the thermogravimetric analysis curve of the crystal form A shows a weight loss of 1.20% at 180.0±3° C.

10. The crystal form A according to claim 3, wherein the thermogravimetric analysis curve of the crystal form A shows a weight loss of 1.20% at 180.0±3° C.

11. A method of treating solid tumor in a subject in need thereof, comprising administering an effective amount of the crystal form A of the compound of Formula (I) according to claim 1 to the subject.

12. The method according to claim 11, wherein the solid tumor is an RET kinase-associated solid tumor.

* * * * *